US008147872B2

(12) United States Patent
Crew et al.

(10) Patent No.: US 8,147,872 B2
(45) Date of Patent: Apr. 3, 2012

(54) PHARMACEUTICAL COMPOSITIONS OF DRUGS AND NEUTRALIZED ACIDIC POLYMERS

(75) Inventors: Marshall Crew, Bend, OR (US);
Dwayne T. Friesen, Bend, OR (US);
Rodney J. Ketner, Bend, OR (US);
Ravi M. Shanker, Groton, CT (US);
James B. West, Bend, OR (US)

(73) Assignee: Bend Reseach, Inc., Bend, OR (US)

( * ) Notice: Subject to any disclaimer, the term of this patent is extended or adjusted under 35 U.S.C. 154(b) by 1764 days.

(21) Appl. No.: 11/213,118

(22) Filed: Aug. 26, 2005

(65) Prior Publication Data
US 2006/0003011 A1 Jan. 5, 2006

Related U.S. Application Data

(63) Continuation of application No. 10/175,566, filed on Jun. 17, 2002, now abandoned.

(60) Provisional application No. 60/300,256, filed on Jun. 22, 2001.

(51) Int. Cl.
A61K 9/14 (2006.01)
A61K 9/00 (2006.01)
A61K 31/716 (2006.01)

(52) U.S. Cl. .......... 424/489; 424/488; 424/400; 514/57
(58) Field of Classification Search .................. 424/488, 424/400, 489
See application file for complete search history.

(56) References Cited

U.S. PATENT DOCUMENTS

| 2,784,185 | A | | 3/1957 | Schuler ........................ 260/243 |
|---|---|---|---|---|
| 2,830,987 | A | | 4/1958 | Gaillot et al. ................. 260/243 |
| 2,901,478 | A | | 8/1959 | Schuler ........................ 260/243 |
| 4,540,602 | A | | 9/1985 | Motoyama et al. ...... 427/213.31 |
| 4,753,800 | A | | 6/1988 | Mozda .......................... 424/440 |
| 4,835,186 | A | | 5/1989 | Reuter et al. ................. 514/570 |
| 4,894,235 | A | | 1/1990 | Kohne et al. ................. 424/452 |
| 4,985,419 | A | | 1/1991 | Garret et al. ................. 514/211 |
| 5,225,202 | A | | 7/1993 | Hodges et al. ................ 424/480 |
| 5,346,542 | A | * | 9/1994 | Yosuke et al. ............. 106/198.1 |
| 5,456,923 | A | | 10/1995 | Nakamichi et al. ........... 424/489 |
| 5,508,276 | A | | 4/1996 | Anderson et al. ............. 514/183 |
| 5,593,690 | A | | 1/1997 | Akiyama et al. ............. 424/457 |
| 5,656,297 | A | | 8/1997 | Bernstein et al. ............. 424/484 |
| 5,684,040 | A | | 11/1997 | Grabowski et al. ........... 514/457 |
| 5,955,475 | A | | 9/1999 | Krape et al. .................. 514/321 |
| 5,968,251 | A | | 10/1999 | Auweter et al. .............. 106/498 |
| 6,068,856 | A | | 5/2000 | Sachs et al. .................. 424/474 |
| 6,306,434 | B1 | | 10/2001 | Hong et al. ................... 424/455 |
| 6,468,559 | B1 | | 10/2002 | Chen et al. ................... 424/451 |
| 6,706,283 | B1 | * | 3/2004 | Appel et al. .................. 424/473 |
| 2002/0103225 | A1 | | 8/2002 | Curatolo et al. .............. 514/313 |

FOREIGN PATENT DOCUMENTS

| EP | 0291838 | | 11/1988 |
|---|---|---|---|
| EP | 0462066 | | 12/1991 |
| EP | 0232155 | | 10/1994 |
| EP | 0580860 | | 10/1997 |
| EP | 0 901 786 A2 | * | 3/1999 |
| EP | 0901786 | | 3/1999 |
| EP | 0988863 | | 3/2000 |
| EP | 1027886 | | 8/2000 |
| EP | 1027887 A2 | | 8/2000 |
| EP | 1027888 A2 | | 8/2000 |
| JP | 59193832 | | 11/1984 |
| WO | WO 9311749 | | 6/1993 |
| WO | WO 0064414 | | 11/2000 |
| WO | WO 0130768 | | 5/2001 |
| WO | WO 0198278 | | 12/2001 |
| WO | WO 0211710 | | 2/2002 |
| WO | WO 02057244 | | 7/2002 |

OTHER PUBLICATIONS

Hackh's Chemical Dictinary, fourth edition, edited by Grant, 1969, p. 452.*
Schmidt, et al., Incorporation of Polymeric Nanoparticles into Solid Dosage Forms, Journal of Controlled Release, 57, pp. 115125 (1999).
Takenaka, et al., Preparation of Enteric-Coated Microcapsules for Tableting by Spray-Drying Technique and in Vitro Simulation of Drug Release from the Tablet in GI Tract, Journal of Pharmaceutical Sciences, vol. 69, No. 12, pp. 1388-1392 (1980).
Takeuchi, et al., Spherical Solid Dispersion Containing Amorphous Tolbutamide Embedded in Enteric Coating Polymers or Colloidal Silica Prepared by Spray-Drying Technique, Chem. Pharm. Bull. vol. 35, pp. 3800-3806, (1987).

* cited by examiner

Primary Examiner — Blessing Fubara
(74) Attorney, Agent, or Firm — Chernoff, Vilhauer, McClung & Stenzel

(57) ABSTRACT

Pharmaceutical compositions comprised of low-solubility and/or acid-sensitive drugs and neutralized acidic polymers are disclosed.

15 Claims, No Drawings

PHARMACEUTICAL COMPOSITIONS OF DRUGS AND NEUTRALIZED ACIDIC POLYMERS

CROSS REFERENCE TO RELATED APPLICATION

This application is a Continuation of U.S. application Ser. No. 10/175,566 filed Jun. 17, 2002, which claims the benefit of U.S. Provisional Application No. 60/300,256 filed Jun. 22, 2001.

BACKGROUND OF THE INVENTION

This invention relates to pharmaceutical compositions of drugs and neutralized acidic polymers that provide improved chemical and physical properties.

It is often desired to improve the aqueous concentration and bioavailability of a poorly soluble drug. Improving either the dissolution rate of the drug or the maximum concentration of drug achieved in an aqueous use environment can enhance the absorption and hence bioavailability of the drug. Further, decreasing the rate at which the concentration of drug falls from the maximum concentration to the equilibrium concentration may also improve bioavailability.

Forming a dispersion of a drug and polymer may enhance drug concentration in a use environment. For example, Curatolo, et al., EP 0 901 786 A2 disclose forming pharmaceutical spray dried amorphous dispersions of sparingly soluble drugs and the polymer hydroxypropyl methyl cellulose acetate succinate. The spray dried dispersions disclosed in Curatolo et al. provide superior aqueous concentration relative to dispersions formed from other methods and relative to the crystalline drug alone.

Similarly, others have recognized the enhancement in aqueous concentration afforded by dispersing a drug in a polymer. Nakamichi, et al., U.S. Pat. No. 5,456,923 disclose solid dispersions formed by twin-screw extrusion of low solubility drugs and various polymers, including hydroxypropyl methyl cellulose acetate succinate and hydroxypropyl methyl cellulose phalthalate, among others.

Nevertheless, dispersing a low-solubility drug in a polymer continues to present challenges. One problem encountered is that the drug and/or dispersion may not be physically stable. The amorphous drug may separate from the dispersion polymer, either as a drug-enriched amorphous phase or as a crystalline phase, thereby decreasing the concentration enhancement provided by the dispersion.

The inventors have also found that for some drugs, the drugs are not chemically stable within some dispersion polymers. In particular, the inventors have observed that for dispersions containing certain drugs and acidic polymers, the drug chemically degrades in the dispersion over time, resulting in a loss of potency and an increase in unwanted impurities.

Anderson et al., U.S. Pat. No. 5,508,276 disclose an enteric duloxetine pellet comprising a core consisting of duloxetine, an optional separating layer, and an enteric layer comprising hydroxypropyl methyl cellulose acetate succinate (HPMCAS). The HPMCAS may be partially neutralized to form a smooth, coherent enteric layer.

Hodges et al., U.S. Pat. No. 5,225,202 disclose an enteric coated composition which includes a medicament which is sensitive to a low pH environment of less than 3. The composition has an enteric coating formed of neutralized hydroxypropylmethyl cellulose acetate phthalate, plasticizer and anti-adherent.

Takeuchi, et al. *Spherical Solid Dispersion Containing Amorphous Tolbutamide Embedded in Enteric Coating Polymers or Colloidal Silica Prepared* by *Spray-Drying Technique*, Chem. Pharm. Bull. Vol. 35, pp. 3800-3806 (1987), disclose solid amorphous dispersions of tolbutamide and an enteric polymer. The drug and polymer are initially dissolved in a 2 wt % ammonia solution forming ammonium salts, but reverted to their original forms during the spray-drying process.

Nevertheless, there is still a need for pharmaceutical compositions of low-solubility drugs and polymers that have improved physical stability, chemical stability, and/or improved concentration enhancement and bioavailability.

BRIEF SUMMARY OF INVENTION

The present invention provides, in one aspect, pharmaceutical compositions comprising a mixture of a low-solubility drug in a solubility-improved form and a neutralized acidic enteric polymer, wherein said composition provides enhanced concentration of said low-solubility drug in a use environment relative to a control composition, wherein said control composition comprises an equivalent quantity of said low-solubility drug and is free from a concentration-enhancing polymer.

In a preferred embodiment, the mixture is a solid amorphous dispersion of said low-solubility drug and said neutralized acidic enteric polymer.

In another preferred embodiment, the degree of neutralization of said neutralized acidic enteric polymer is at least 0.1, preferably at least 0.5, more preferably at least 0.9, more preferably about 1.

In another preferred embodiment, the neutralized acidic enteric polymer comprises a counterion selected from the group consisting of sodium, potassium, calcium, magnesium, aluminum, ammonium, iron, and amine.

In another preferred embodiment, the neutralized acidic enteric polymer comprises a blend of polymers.

In another preferred embodiment, the neutralized acidic enteric polymer is cellulosic, preferably selected from the group consisting of hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, and carboxymethyl ethyl cellulose. More preferably, the neutralized acidic enteric polymer is selected from the group consisting of hydroxypropyl methyl cellulose acetate succinate, cellulose acetate phthalate, cellulose acetate trimellitate, hydroxypropyl methyl cellulose phthalate, and carboxymethyl ethyl cellulose.

In another preferred embodiment, the neutralized acidic enteric polymer is a neutralized form of a polymer selected from the group consisting of carboxylic acid functionalized vinyl polymers, carboxylic acid functionalized polymethacrylates, and carboxylic acid functionalized polyacrylates.

In another preferred embodiment, the neutralized acidic enteric polymer has a glass transition temperature of at least 40° C.

In another preferred embodiment, the neutralized acidic enteric polymer is ionically crosslinked, preferably the neutralized acidic enteric polymer is ionically crosslinked with a multivalent cationic species. Preferably, the multivalent cationic species is selected from the group consisting of calcium, magnesium, aluminum, iron (II), iron (III), and a diamine.

In another preferred embodiment, the composition further comprises a base. Preferably, the base is selected from the group consisting of sodium hydroxide, potassium hydroxide, calcium hydroxide, magnesium hydroxide, aluminum hydroxide, ammonia, ammonium hydroxide, ammonium acetate, sodium acetate, potassium acetate, calcium acetate, magnesium acetate, sodium citrate, trisodium phosphate, disodium phosphate, ethylene diamine, monoethanol amine, diethanol amine, triethanolamine, potassium citrate, sodium carbonate, sodium bicarbonate, sodium acetate, amine-functional polyacrylates, and sodium polyacrylic acid. Preferably, the base comprises at least 5 wt % of said composition.

In another preferred embodiment, the drug has a solubility in aqueous solution in the absence of said polymer of less than 1 mg/ml, preferably less than 0.1 mg/ml, at any pH of from about 1 to about 8.

In another preferred embodiment, the drug has a dose-to-aqueous-solubility ratio of at least 10 ml.

In another preferred embodiment, the low-solubility drug is acid-sensitive. Preferably, the acid-sensitive drug has at least one functional group selected from the group consisting of sulfonyl ureas, hydroxamic acids, hydroxy amides, carbamates, acetals, hydroxy ureas, esters, and amides. Preferably, the acid-sensitive drug is selected from the group consisting of quinoxaline-2-carboxylic acid [4(R)-carbamoyl-1 (S)-3-fluorobenzyl-2(S), 7-dihydroxy-7-methyl-octyl] amide; quinoxaline-2-carboxylic acid [1-benzyl-4-(4,4-difluoro-1-hydroxy-cyclohexyl)-2-hydroxy-4-hydroxycarbamoyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide.

In another preferred embodiment, the composition provides improved chemical stability of said drug relative to a second control composition, wherein said second control composition comprises a dispersion of an equivalent quantity of said low-solubility drug and an unneutralized form of said neutralized acidic enteric polymer. Preferably, the composition provides a relative degree of improvement in stability for said drug of at least 1.25, preferably at least 3, more preferably at least 10, when stored at 40° C. and 75% relative humidity.

In another preferred embodiment, the maximum concentration of said drug in said use environment is at least 1.25-fold that of said control composition.

In another preferred embodiment, the neutralized acidic enteric polymer is present in a sufficient amount so that said composition provides in said use environment an area under the concentration versus time curve for any period of at least 90 minutes between the time of introduction into the use environment and about 270 minutes following introduction to said use environment that is at least 1.25-fold, preferably at least 2-fold, that of said control composition.

In another preferred embodiment, the neutralized acidic enteric polymer is present in a sufficient amount so that said composition provides a relative bioavailability that is at least 1.25 relative to said control composition.

In another preferred embodiment, the composition further comprises a second concentration-enhancing polymer.

In a second aspect, the present invention relates to pharmaceutical compositions comprising a solid amorphous dispersion of an acid-sensitive drug and a neutralized acidic dispersion polymer, wherein said composition provides improved chemical stability of said drug relative to a control composition comprised of a dispersion of an equivalent quantity of said drug and an unneutralized form of said acidic polymer. Preferably, the degree of neutralization of said neutralized acidic polymer is at least 0.1, more preferably at least 0.5, more preferably at least 0.9, more preferably at least 1.

In another preferred embodiment, the neutralized acidic dispersion polymer has a counterion selected from the group consisting of sodium, potassium, calcium, magnesium, aluminum, ammonium, iron, and amine.

In another preferred embodiment, the neutralized acidic dispersion polymer comprises a blend of polymers.

In another preferred embodiment, the neutralized acidic dispersion polymer is cellulosic. Preferably, neutralized acidic dispersion polymer is a neutralized form of a polymer selected from the group consisting of hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, ethyl picolinic acid cellulose acetate, carboxymethyl ethyl cellulose, carboxy methyl cellulose, and carboxy ethyl cellulose. More preferably, the neutralized acidic polymer is a neutralized form of a polymer selected from the group consisting of hydroxy propyl methyl cellulose acetate succinate, cellulose acetate phthalate, cellulose acetate trimellitate, hydroxypropyl methyl cellulose phthalate, carboxymethyl cellulose, carboxymethyl ethyl cellulose.

In another preferred embodiment, the neutralized acidic dispersion polymer is a neutralized form of a polymer selected from the group consisting of carboxylic acid functionalized vinyl polymers, carboxylic acid functionalized polymethacrylates, and carboxylic acid functionalized polyacrylates.

In another preferred embodiment, the neutralized acidic dispersion polymer has a glass transition temperature of at least 40° C.

In another preferred embodiment, the composition further comprises a base. Preferably, the composition comprises a physical mixture of said dispersion and said base. Preferably, the base is selected from the group consisting of sodium hydroxide, potassium hydroxide, calcium hydroxide, magnesium hydroxide, aluminum hydroxide, ammonia, ammonium hydroxide, ammonium acetate, sodium acetate, potassium acetate, calcium acetate, magnesium acetate, sodium citrate, trisodium phosphate, disodium phosphate, ethylene diamine, monoethanol amine, diethanol amine, triethanolamine, potassium citrate, sodium carbonate, sodium bicarbonate, sodium acetate, amine-functional polyacrylates, and sodium polyacrylic acid.

In another preferred embodiment, the dispersion has a pH greater than 5.

In another preferred embodiment, the acid-sensitive drug has a solubility in aqueous solution in the absence of said neutralized acidic polymer of less than 1 mg/ml, preferably less than 0.1 mg/ml, at any pH of from about 1 to about 8.

In another preferred embodiment, the acid-sensitive drug has a dose-to-aqueous-solubility ratio of at least 10 ml.

In another preferred embodiment, the acid-sensitive drug has at least one functional group selected from the group consisting of sulfonyl ureas, hydroxamic acids, hydroxy amides, carbamates, acetals, hydroxy ureas, esters, and amides.

In another preferred embodiment, the acid-sensitive drug is selected from the group consisting of quinoxaline-2-carboxylic acid [4(R)-carbamoyl-1(S)-3-fluorobenzyl-2(S), 7-dihydroxy-7-methyl-octyl]amide; quinoxaline-2-carboxylic acid [1-benzyl-4-(4,4-difluoro-1-hydroxy-cyclohexyl)-2-hydroxy-4-hydroxycarbamoyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide.

In another preferred embodiment, the composition provides a relative degree of improvement for said drug of at least 1.25, preferably at least 3, more preferably at least 10, when stored at 40° C. and 75% relative humidity.

In another preferred embodiment, the neutralized acidic polymer is concentration-enhancing and present in a sufficient amount to provide a maximum concentration of said acid-sensitive drug in a use environment that is at least 1.25-fold that of a second control composition, said second control composition comprising an equivalent quantity of said acid-sensitive drug but free from a concentration-enhancing polymer.

In another preferred embodiment, the neutralized acidic polymer is concentration-enhancing and is present in a sufficient amount so that said composition provides in a use environment an area under the concentration versus time curve for any period of at least 90 minutes between the time of introduction into the use environment and about 270 minutes following introduction to the use environment that is at least 1.25-fold, preferably at least 2-fold, that of a control composition, said second control composition comprising an equivalent quantity of said acid-sensitive drug and free from a concentration-enhancing polymer.

In another preferred embodiment, the neutralized acidic polymer is concentration-enhancing and is present in an amount so that said dispersion provides a relative bioavailability that is at least 1.25 relative to a second control composition, said second control composition comprising an equivalent quantity of said acid-sensitive drug and free from a concentration-enhancing polymer.

In another preferred embodiment, the composition further comprises a second polymer, said second polymer being concentration-enhancing.

In a third aspect, the present invention relates to methods for treating a condition in an animal comprising administering to an animal in need of such treatment a therapeutic amount of the above-described compositions.

In a fourth aspect, the present invention relates to methods for forming a solid pharmaceutical composition, comprising the steps of: (a) neutralizing an acidic enteric polymer to form a neutralized acidic enteric polymer; and (b) combining a low-solubility drug with said neutralized acidic enteric polymer, said neutralized acidic enteric polymer being present in a sufficient amount in said composition so as to be concentration-enhancing.

In a preferred embodiment, step (a) further comprises the steps of (1) dissolving said acidic enteric polymer in a solvent to form a solution and (2) adding a base to said solution.

In another preferred embodiment, the low-solubility drug and said acidic enteric polymer are both dissolved in a common solvent to form a solution. Preferably, the method further comprises the step of adding a base to said solution. Preferably, the solvent is removed from said solution forming a solid amorphous dispersion.

In another preferred embodiment, the acidic enteric polymer is neutralized prior to being combined with said drug. Alternatively, the acidic enteric polymer is combined with said drug prior to neutralizing said acidic enteric polymer.

In another preferred embodiment, the drug and said neutralized acidic enteric polymer are combined to form a solid amorphous dispersion.

In another preferred embodiment, the drug at least partially neutralizes said polymer.

The fifth aspect of the present invention relates to methods for forming a pharmaceutical composition, comprising the steps of: (a) neutralizing an acidic polymer to form a neutralized acidic polymer; and (b) forming a solid amorphous dispersion of an acid-sensitive drug and said neutralized acidic polymer, said dispersion providing improved chemical stability relative to a control composition comprised of an equivalent quantity of said acid-sensitive drug and the unneutralized form of said neutralized acidic polymer.

In a preferred embodiment, the acidic polymer is neutralized prior to being combined with said acid-sensitive drug. Alternatively, the acidic polymer and said drug are combined prior to neutralizing said acidic polymer.

In a sixth aspect, the present invention relates to methods for forming a pharmaceutical composition, comprising the steps of: (a) forming a solid amorphous dispersion of an acid-sensitive drug and an acidic polymer; and (b) neutralizing said acidic polymer after forming said dispersion.

In a preferred embodiment, the acidic polymer is neutralized by combining said dispersion with a base.

The present inventors have found that neutralized acidic enteric polymers provide several advantages over conventional unneutralized acidic enteric polymers. Compositions of neutralized acidic enteric polymers and drugs tend to be more physically and chemically stable than unneutralized polymers. Thus, the compositions may provide improved uniformity of drug potency and concentration enhancement when administered to a use environment after being stored under typical ambient storage conditions. In addition, neutralized acidic enteric polymers also may provide greater concentration enhancement and faster dissolution. This may lead to improved bioavailability of the low-solubility drug.

Often, acidic dispersion polymers are preferred for use with low-solubility drugs because such polymers often provide greater concentration enhancement than that provided by non-acidic polymers. However, the inventors have recognized that a problem with forming dispersions of acid-sensitive drugs is that for some dispersions, the drug does not remain chemically stable in the dispersion over time. The inventors have found that acid-sensitive drugs dispersed in an acidic polymer, such as hydroxypropyl methyl cellulose acetate succinate or cellulose acetate phthalate, both of which have carboxylic acid functional groups, have a tendency to chemically degrade over time. It is believed that the presence of acidic ionic groups on the acidic polymer either catalyze degradation of the drug or react directly with the drug. Such reactions may occur due to the acidic environment induced by the presence of the carboxylic acid groups (for example, a high hydrogen ion activity) or by direct interaction of the drug and the carboxylic acid groups.

In any event, regardless of the particular degradation mechanism, the inventors have substantially reduced, if not eliminated the problem, by forming dispersions using neutralized forms of the otherwise acidic dispersion polymer. Thus, the present invention is able to realize the advantages of forming dispersions of low-solubility, acid-sensitive drugs by improving the chemical stability of the acid-sensitive drug in the dispersion, while retaining the superior concentration enhancement provided by the use of acidic dispersion polymers.

As described more fully below, the term "use environment" may refer to either the in vivo environment of the gastrointestinal (GI) tract of an animal, particularly a human, or the in vitro environment of a test solution, such as phosphate buffered saline (PBS) or model fasted duodenal (MFD) solution.

The compositions of the present invention may be dosed in a variety of dosage forms, including both immediate release and controlled release dosage forms, the latter including both delayed and sustained release forms. The composition may include blends of polymers.

The foregoing and other objectives, features, and advantages of the invention will be more readily understood upon consideration of the following detailed description of the invention.

DETAILED DESCRIPTION OF THE INVENTION

The pharmaceutical compositions of the present invention comprise mixtures of a drug and a neutralized acidic polymer. The present invention finds utility anytime it is desired to improve the aqueous concentration of a low-solubility drug, and finds particular utility when the drug is acid-sensitive.

In a first embodiment of the invention, the composition comprises a mixture of a low-solubility drug and a neutralized acidic enteric polymer. Compositions formed from neutralized acidic enteric polymers provide improved physical and/or chemical drug stability, concentration-enhancement and dissolution properties relative to the unneutralized form of the acidic enteric polymer. Thus, the invention will find utility for any low-solubility drug and/or composition which may benefit from improved physical or chemical stability, improved concentration enhancement, and/or improved dissolution.

In the first embodiment of the invention the drug and neutralized acidic enteric polymer may be mixed in any conventional fashion so as to achieve a relatively uniform mixture. The drug and polymer may exist in drug-rich and polymer-rich domains, may exist together as a homogeneous solid solution or in some state in between. The mixture may be formed by any conventional method, such as by blending, milling, or granulating. A preferred mixture is a molecular dispersion.

In a second embodiment, a composition comprises a dispersion of an acid-sensitive drug and a neutralized acidic polymer. Dispersions of the present invention formed from neutralized acidic polymers improve the chemical stability of acid-sensitive drugs relative to dispersions of the same drug in the unneutralized acidic form of the polymer. The dispersions of the second embodiment simultaneously provide enhanced chemical stability and enhanced drug concentration in a use environment and, in turn, enhanced bioavailability. The dispersions may be used to prevent degradation of the drug due to interactions with dispersion polymers, other acidic dispersion species, or other acidic excipients present in the composition.

Suitable drugs, particularly acid-sensitive drugs, acidic polymers and methods for making the various compositions of low-solubility drug and acidic polymer are discussed in more detail below.

The Drug

The term "drug" is conventional, denoting a compound having beneficial prophylactic and/or therapeutic properties when administered to an animal, especially humans. The drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and the dose is in mg. The dose-to-aqueous-solubility-ratio may be determined by simply dividing the dose (in mg) by the aqueous solubility (in mg/mL).

The drug must be formulated in a manner so as to be capable of providing an initially enhanced drug concentration that is greater than the equilibrium concentration of the drug in the use environment (i.e., a super-saturated drug concentration). It is believed that the polymers of the present invention do not have the ability to enhance the solubility of the drug in the use environment. Instead, the polymers inhibit or retard the rate at which the initially enhanced concentration of drug decreases to the equilibrium concentration of drug. The drug may be formulated as a solid amorphous dispersion of drug and polymer such that the dispersion provides an initial concentration of drug in the use environment that is greater than the equilibrium concentration of drug in the use environment.

Alternatively, the drug may be formulated in a solubility-improved form. Solubility-improved forms include crystal and highly soluble salt forms of the drug, high-energy crystalline forms of the drug (such as polymorphs), amorphous drug, a mixture of the drug and a solubilizing agent, and drug predissolved in a solution. Examples of such solubility-improved forms are more fully described in commonly assigned pending patent application titled Pharmaceutical Compositions Providing Enhanced Drug Concentrations, Ser. No.

09/742,785, filed Dec. 20, 2000, which claims priority to provisional patent application Ser. No. 60/171,841, filed Dec. 23, 1999, the disclosure of which is incorporated by reference.

As yet another alternative, the drug may be a basic drug which dissolves readily in gastric solution. Upon entering intestinal solution, a drug concentration that exceeds the equilibrium concentration of drug in the intestinal solution may be temporarily achieved. Such basic drugs are disclosed in commonly assigned pending patent application Ser. No. 09/495,438, filed Jan. 31, 2000, which claims priority to provisional patent application Ser. No. 60/119,283, filed Feb. 9, 1999, the relevant disclosure of which is herein incorporated by reference.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, anti-artheriosclerotic agents, glycogen phosphorylase inhibitors, and cholesterol ester transfer protein inhibitors.

Specific examples of the above and other classes of drugs and therapeutic agents deliverable by the invention are set forth below, by way of example only. Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4'-trimethylphenoxy)pyridine, pyroxidine, fluoxetine, paroxetine, venlafaxine and sertraline; specific examples of antibiotics include carbenicillin indanyl-sodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein (CETP) inhibitors include [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S]4-[(3,5-Bis-trifluoromethyl-benzyl)-methoxycarbonyl-amino]-2-ethyl-6-trifluoromethyl-3,4-dihydro-2H-quinoline-1-carboxylic acid isopropyl ester.

The invention is not limited by any particular structure or group of CETP inhibitors. Rather, the invention has general applicability to CETP inhibitors as a class, the class tending to be composed of compounds having low solubility. Compounds which may be the subject of the invention may be found in a number of patents and published applications, including DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

The invention is useful for CETP inhibitors that have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 µg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 µg/mL, and even more preferred for CETP inhibitors with solubilities less than about 0.5 µg/mL. Many CETP inhibitors have even lower solubilities (some even less than 0.1 µg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 µg/ml, often being less than 0.1 µg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestsinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobocity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 µg/ml and preferably less than about 1 µg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailibility of drugs in this subclass when dosed orally in their undispersed state is less than about 10% and more often less than about 5%.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

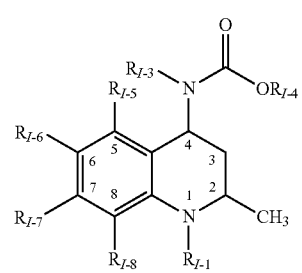

Formula I and pharmaceutically acceptable salts, enantiomers, or stereoisomers of said compounds;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—$Y_I$ or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; $R_{I-3}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo carbamoyl, mono-N— or di-N,N—$(C_1-C_6)$alkylcarbamoyl, carboxyl, $(C_1-C_6)$alkyloxycarbonyl, mono-N— or di-N,N,—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxyl, $(C_1-C_6)$alkyloxycarbonyl, mono-N— or di-N,N— $(C_1-C_6)$alkylamino, said $(C_1-C_6)$alkyl or $(C_2-C_6)$alkenyl substituents are also optionally substituted with from one to nine fluorines; $R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines.

Compounds of Formula I and their methods of manufacture are disclosed in commonly assigned U.S. Pat. No. 6,140,342, U.S. Pat. No. 6,362,198, and European Patent publication 987251, all of which are incorporated herein by reference in their entireties for all purposes.

In a preferred embodiment, the CETP inhibitor is selected from one of the following compounds of Formula I:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;
[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;
[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester,
[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;
[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;
[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;
[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid propyl ester;
[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;
[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,
[2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester;
[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester; and
[2R,4S](3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride.

Another class of CETP inhibitors that finds utility with the present invention consists of 4-carboxyamino-2-methyl-1,2,3,4,-tetrahydroquinolines, having the Formula II

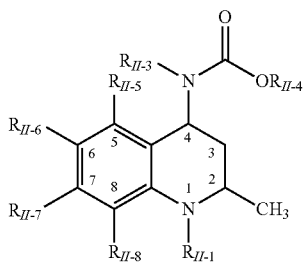

Formula II and pharmaceutically acceptable salts, enantiomers, or stereoisomers of said compounds;
wherein $R_{II-1}$ is hydrogen, $Y_{II}$, $W_{II}-X_{II}$, $W_{II}-Y_{II}$;
wherein $W_{II}$ is a carbonyl, thiocarbonyl, sulfinyl or sulfonyl;
$X_{II}$ is $-O-Y_{II}$, $-S-Y_{II}$, $-N(H)-Y_{II}$ or $-N-(Y_{II})_2$;
wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl is also optionally substituted with from one to nine fluorines;

$R_{II-3}$ is hydrogen or $Q_{II}$;
wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said V, substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl substituents are optionally substituted with from one to nine fluorines;

$R_{II-4}$ is $Q_{II-1}$ or $V_{II-1}$
wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II and their methods of manufacture are disclosed in commonly assigned U.S. Pat. No. 6,147,090, U.S. patent application Ser. No. 09/671,400 filed Sep. 27, 2000, and PCT Publication No. WO00/17166, all of which are incorporated herein by reference in their entireties for all purposes.

In a preferred embodiment, the CETP inhibitor is selected from one of the following compounds of Formula II:

[2R,4S]4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S]4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2,6,7-trimethyl-3,4-dihydro-2H-quinoline-1-carboxylic acid ethyl ester;

[2R,4S]4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester; and

[2R,4S]4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

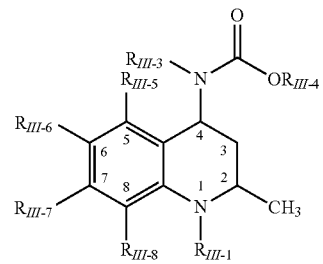

Formula III and pharmaceutically acceptable salts, enantiomers, or stereoisomers of said compounds;

wherein $R_{III-1}$ is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—(C$_1$-C$_6$)alkylamino, said (C$_1$-C$_6$)alkyl optionally substituted with from one to nine fluorines;

R$_{III-3}$ is hydrogen or Q$_{III}$;

wherein Q$_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with V$_{III}$;

wherein V$_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said V$_{III}$ substituent is optionally mono-, di-, tri-, or tetra-substituted independently with halo, (C$_1$-C$_6$)alkyl, (C$_2$-C$_6$)alkenyl, hydroxy, (C$_1$-C$_6$)alkoxy, (C$_1$-C$_4$)alkylthio, amino, nitro, cyano, oxo, carboxamoyl, mono-N— or di-N,N—(C$_1$-C$_6$)alkylcarboxamoyl, carboxy, (C$_1$-C$_6$)alkyloxycarbonyl, mono-N— or di-N,N—(C$_1$-C$_6$)alkylamino wherein said (C$_1$-C$_6$)alkyl or (C$_2$-C$_6$)alkenyl substituent is optionally mono-, di- or tri-substituted independently with hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$)alkylamino or said (C$_1$-C$_6$)alkyl or (C$_2$-C$_6$)alkenyl are optionally substituted with from one to nine fluorines;

R$_{III-4}$ is Q$_{III-1}$ V$_{III-1}$;

wherein Q$_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with V$_{III-1}$;

wherein V$_{III-1}$ is a partially saturated, fully saturated or fully unsaturated three to six membered ring optionally having one to two heteroatoms selected independently from oxygen, sulfur and nitrogen;

wherein said V$_{III-1}$ substituent is optionally mono-, di-, tri-, or tetra-substituted independently with halo, (C$_1$-C$_6$)alkyl, (C$_1$-C$_6$)alkoxy, amino, nitro, cyano, (C$_1$-C$_6$)alkyloxycarbonyl, mono-N— or di-N,N—(C$_1$-C$_6$)alkylamino wherein said (C$_1$-C$_6$)alkyl substituent is optionally mono-substituted with oxo, said (C$_1$-C$_6$)alkyl substituent optionally having from one to nine fluorines;

wherein either R$_{III-3}$ must contain V$_{III}$ or R$_{III-4}$ must contain V$_{III-1}$; and R$_{III-5}$ and R$_{III-6}$ or R$_{III-6}$ and R$_{III-7}$, and/or R$_{III-7}$ and R$_{III-8}$ are taken together and form at least one four to eight membered ring that is partially saturated or fully unsaturated optionally having one to three heteroatoms independently selected from nitrogen, sulfur and oxygen;

wherein said ring or rings formed by R$_{III-5}$ and R$_{III-6}$, or R$_{III-6}$ and R$_{III-7}$, and/or R$_{III-7}$ and R$_{III-8}$ are optionally mono-, di- or tri-substituted independently with halo, (C$_1$-C$_6$)alkyl, (C$_1$-C$_4$)alkylsulfonyl, (C$_2$-C$_6$)alkenyl, hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$)alkylamino wherein said (C$_1$-C$_6$)alkyl substituent is optionally mono-, di- or tri-substituted independently with hydroxy, (C$_1$-C$_6$)alkoxy, (C$_1$-C$_4$)alkylthio, amino, nitro, cyano, oxo, carboxy, (C$_1$-C$_6$)alkyloxycarbonyl, mono-N— or di-N,N—(C$_1$-C$_6$)alkylamino, said (C$_1$-C$_6$)alkyl substituent optionally having from one to nine fluorines;

provided that the R$_{III-5}$, R$_{III-6}$, R$_{III-7}$ and/or R$_{III-8}$, as the case may be, that do not form at least one ring are each independently hydrogen, halo, (C$_1$-C$_6$)alkoxy or (C$_1$-C$_6$)alkyl, said (C$_1$-C$_6$)alkyl optionally having from one to nine fluorines.

Compounds of Formula III and their methods of manufacture are disclosed in commonly assigned U.S. Pat. No. 6,147,089, U.S. Pat. No. 6,310,075, and European Patent Application No. 99307240.4 filed Sep. 14, 1999, all of which are incorporated herein by reference in their entireties for all purposes.

In a preferred embodiment, the CETP inhibitor is selected from one of the following compounds of Formula III:

[2R, 4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R, 8S]8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethyl ester;

[6R, 8S]8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S]4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S]4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S]9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R]6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

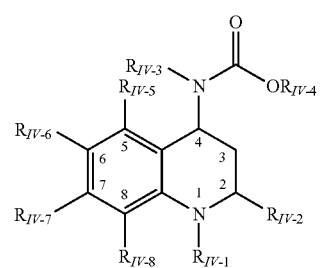

Formula IV and pharmaceutically acceptable salts, enantiomers, or stereoisomers of said compounds;

wherein $R_{IV-1}$ is hydrogen, $Y_{IV}$, $W_{IV}—X_{IV}$ or $W_{IV}—Y_{IV}$;

wherein $W_{IV}$ is a carbonyl, thiocarbonyl, sulfinyl or sulfonyl;

$X_{IV}$ is $—O—Y_{IV}$, $—S—Y_{IV}$, $—N(H)—Y_{IV}$ or $—N—(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$alkyl;

wherein said $R_{IV-2}$ ring is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, oxo or $(C_1-C_6)$alkyloxycarbonyl; with the proviso that $R_{IV-2}$ is not methyl; $R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$alkenyl substituents are also optionally substituted with from one to nine fluorines;

$R_{IV-4}$ is $Q_{I-1}$ or $V_{IV-1}$;

wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$ alkoxy, $(C_1-C_4)$alkylthio, amino, nitro, cyano, oxo, carboxy, $(C_1-C_6)$alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; with the proviso that when $R_{IV-2}$ is carboxyl or $(C_1-C_4)$alkylcarboxyl, then $R_{IV-2}$ is not hydrogen.

Compounds of Formula IV and their methods of manufacture are disclosed in commonly assigned U.S. Pat. No. 6,197,786, U.S. application Ser. No. 09/685,300 filed Oct. 10, 2200, and PCT Publication No. WO 00/17164, all of which are incorporated herein by reference in their entireties for all purposes.

In a preferred embodiment, the CETP inhibitor is selected from one of the following compounds of Formula IV:

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R]4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

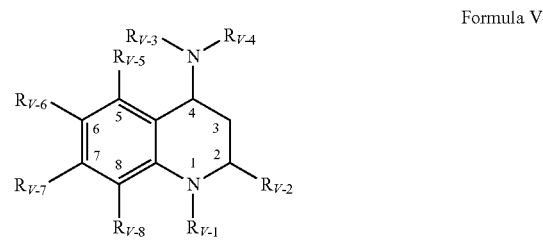

Formula V and pharmaceutically acceptable salts, enantiomers, or stereoisomers of said compounds;

wherein $R_{V-1}$ is $Y_V$, $W_V—X_V$ or $W_V—Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—$(Y_V)_2$;

wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-2}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, oxo or $(C_1-C_6)$alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo carboxamoyl, mono-N— or di-N,N—$(C_1-C_6)$alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{V-4}$ is cyano, formyl, $W_{V-1}Q_{V-1}$, $W_{V-1}V_{V-1}$, $(C_1-C_4)$alkyleneV$_{V-1}$ or V$_{V-2}$;

wherein $W_{V-1}$ is carbonyl, thiocarbonyl, SO or $SO_2$, wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{V-1}$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$ alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C^4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_v$;

wherein $T_v$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_v$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1$-

$C_6$)alkyl substituent is optionally mono-, di- or tri-substituted independently with hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N— or di-N,N—($C_1$-$C_6$)alkylamino, said ($C_1$-$C_6$)alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, ($C_1$-$C_6$)alkyl, ($C_1$-$C_4$) alkylsulfonyl, ($C_2$-$C_6$)alkenyl, hydroxy, ($C_1$-$C_6$)alkoxy, ($C_1$-$C_4$)alkylthio, amino, nitro, cyano, oxo, carboxy, ($C_1$-$C_6$) alkyloxycarbonyl, mono-N— or di-N,N—($C_1$-$C_6$) alkylamino wherein said ($C_1$-$C_6$)alkyl substituent is optionally mono-, di- or tri-substituted independently with hydroxy, ($C_1$-$C_6$)alkoxy, ($C_1$-$C_4$)alkylthio, amino, nitro, cyano, oxo, carboxy, ($C_1$-$C_6$)alkyloxycarbonyl, mono-N— or di-N,N—($C_1$-$C_6$)alkylamino, said ($C_1$-$C_6$)alkyl substituent also optionally has from one to nine fluorines.

Compounds of Formula V and their methods of manufacture are disclosed in commonly assigned U.S. Pat. No. 6,140,343, U.S. patent application Ser. No. 09/671,221 filed Sep. 27, 2000, and PCT Publication No. WO 00/17165, all of which are incorporated herein by reference in their entireties for all purposes.

In a preferred embodiment, the CETP inhibitor is selected from one of the following compounds of Formula V:

[2S,4S]4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethy-3,4-dihydro-2H-quinoline-1-carboxylic acid tert-butyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-methyl-6-trifluoromethyl-3,4-dihydro-2H-quinoline-1-carboxylic acid ethyl ester;

[2S,4S]4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S]4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

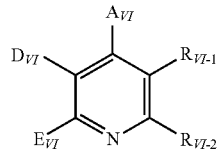

Formula VI and pharmaceutically acceptable salts, enantiomers, or stereoisomers of said compounds;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$BNR_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$,

or $R_{VI-9}$-$T_{VI}$-$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxy, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteoatoms from the series of S, N and/or O, and/or in the form of a group according to the formula $BOR_{VI-10}$, $-SR_{VI-11}$, $-SO_2R_{VI-12}$ or $BNR_{VI-13}R_{VI-14}$, wherein $R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI-13}$ and $R_{VI-14}$ are identical or different and have the meaning of $R_{VI-3}$ and $R_{VI-4}$ given above, or $R_{VI-5}$ and/or $R_{VI-6}$ denote a radical according to the formula

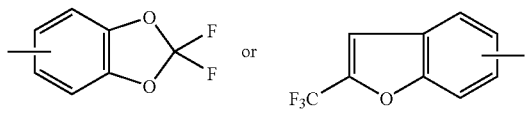

$R_{VI-7}$ denotes a hydrogen or halogen, and $R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

wherein $R_{VI-15}$ and $R_{VI-16}$ are identical or different and have the meaning of $R_{VI-3}$ and $R_{VI-4}$ given above, or $R_{VI-7}$ and $R_{VI-8}$ together form a radical according to the formula $=O$ or $=NR_{VI-17}$, wherein $R_{VI-17}$ denotes a hydrogen or a straight-chain or branched alkyl, alkoxy or acyl containing up to 6 carbon atoms each, $L_{VI}$ denotes a straight-chain or branched alkylene or alkenylene chain containing up to 8 carbon atoms each, which are optionally substituted with up to two hydroxyl groups, $T_{VI}$ and $X_{VI}$ are identical or different and denote a straight-chain or branched alkylene chain containing up to 8 carbon atoms, or $T_{VI}$ or $X_{VI}$ denotes a bond, $V_{VI}$ denotes an oxygen or sulfur atom or an $BNR_{VI-18}$, group, wherein $R_{VI-18}$ denotes a hydrogen or a straight-chain or branched alkyl containing up to 6 carbon atoms or a phenyl, $E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, $R_{VI-1}$ and $R_{VI-2}$ together form a straight-chain or branched alkylene chain containing up to 7 carbon atoms, which must be substituted with a carbonyl group and/or a radical according to the formula

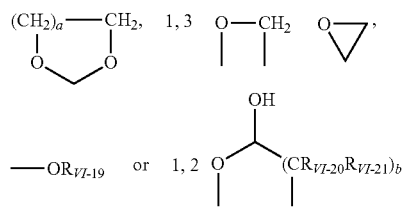

wherein a and b are identical or different and denote a number equaling 1, 2 or 3, $R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula $BOR_{VI-22}$, wherein $R_{VI-22}$ denotes a straight-chain or branched acyl containing up to 4 carbon atoms or benzyl, or $R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, $R_{VI-20}$ and $R_{VI-21}$ are identical or different and denote a hydrogen, phenyl or a straight-chain or branched alkyl containing up to 6 carbon atoms, or $R_{VI-20}$ and $R_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

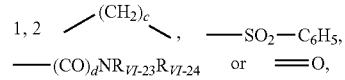

wherein c is a number equaling 1, 2, 3 or 4, d is a number equaling 0 or 1, $R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

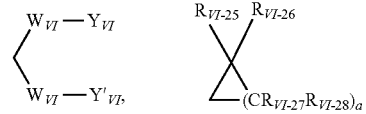

-continued $R_{VI\text{-}31}$ $(CR_{VI\text{-}27}R_{VI\text{-}28})_f$

,

=O or $R_{VI\text{-}32}$
$R_{VI\text{-}33}$ wherein $W_{VI}$ denotes either an oxygen atom or a sulfur atom, $Y_{VI}$ and $Y=_{VI}$ together form a 2- to 6-membered straight-chain or branched alkylene chain, e is a number equaling 1, 2, 3, 4, 5, 6 or 7, f is a number equaling 1 or 2, $R_{VI\text{-}25}$, $R_{VI\text{-}26}$, $R_{VI\text{-}27}$, $R_{VI\text{-}28}$, $R_{VI\text{-}29}$, $R_{VI\text{-}30}$ and $R_{VI\text{-}31}$ are identical or different and trifluoromethyl, phenyl, halogen or a straight-chain or branched alkyl or alkoxy containing up to 6 carbon atoms each, or $R_{VI\text{-}25}$ and $R_{VI\text{-}26}$ or $R_{VI\text{-}27}$ and $R_{VI\text{-}28}$ each together denote a straight-chain or branched alkyl chain containing up to 6 carbon atoms or $R_{VI\text{-}25}$ and $R_{VI\text{-}26}$ or $R_{VI\text{-}27}$ and $R_{VI\text{-}28}$ each together form a radical according to the formula $W_{VI}$ —— $CH_2$
$W_{VI}$ —— $(CH_2)_g$ wherein $W_{VI}$ has the meaning given above, g is a number equaling 1, 2, 3, 4, 5, 6 or 7, $R_{VI\text{-}32}$ and $R_{VI\text{-}33}$ together form a 3- to 7-membered heterocycle, which contains an oxygen or sulfur atom or a group according to the formula SO, $SO_2$ or $BNR_{VI\text{-}34}$, wherein $R_{VI\text{-}34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI and their methods of manufacture are disclosed in European Patent Application No. EP 818448 A1, U.S. Pat. No. 6,207,671 and U.S. Pat. No. 6,069,148, all of which are incorporated herein by reference in their entireties for all purposes.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinoline-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)methanone;

[5-(t-butyldimethylsilanyloxy)-2-cyclopentyl-4-(4-fuorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline; and 2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII Formula VII $R_{VII\text{-}4}$
$R_{VII\text{-}5}$    $R_{VII\text{-}3}$
$R_{VII\text{-}6}$  N  $R_{VII\text{-}2}$ or a pharmaceutically acceptable salt or tautomer thereof, wherein $R_{VII\text{-}2}$ and $R_{VII\text{-}6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII\text{-}2}$ and $R_{VII\text{-}6}$ is fluorinated alkyl, chlorofluorinated alkyl or alkoxyalkyl;

$R_{VII\text{-}3}$ is selected from the group consisting of hydroxy, amido, arylcarbonyl, heteroarylcarbonyl, hydroxymethyl —CHO, —$CO_2R_{VII\text{-}7}$, wherein $R_{VII\text{-}7}$ is selected from the group consisting of hydrogen, alkyl and cyanoalkyl; and $R_{VII\text{-}15a}$
|
——C——$R_{VII\text{-}16a}$
|
H wherein $R_{VII\text{-}15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII\text{-}16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII\text{-}4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, hetereoarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, aryiheteroarylamino, trialkylsilyl, trialkenylsilyt, triarylsilyl, —CO(O)N($R_{VII\text{-}8a}R_{VII\text{-}8b}$), wherein $R_{VII\text{-}8a}$ and $R_{VII\text{-}8b}$ are independently selected from the group consisting of alkyl, alkenyl, alkynyl, aryl, heteroaryl and heterocyclyl, —SO$_2$R$_{VII-9}$, wherein R$_{VII-9}$ is selected from the group consisting of hydroxy, alkyl, alkenyl, alkynyl, aryl, heteroaryl and heterocyclyl, —OP(O)(OR$_{VII-10a}$)(OR$_{VII-10b}$), wherein R$_{VII-10a}$ and R$_{VII-10b}$ are independently selected from the group consisting of hydrogen, hydroxy, alkyl, alkenyl, alkynyl, aryl, heteroaryl and heterocyclyl, and —OP(S)(OR$_{VII-11a}$)(OR$_{VII-11b}$), wherein R$_{VII-11a}$ and R$_{VII-11b}$ are independently selected from the group consisting of alkyl, alkenyl, alkynyl, aryl, heteroaryl and heterocyclyl;

R$_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —CO$_2$R$_{VII-14}$, wherein R$_{VII-14}$ is selected from the group consisting of alkyl, alkenyl, alkynyl, aryl, heteroaryl and heterocyclyl;

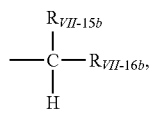

wherein R$_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and R$_{VII-16b}$ is selected form the group consisting of alkyl, alkenyl, alkynyl, aryl, heteroaryl, heterocyclyl, arylalkoxy, and trialkylsilyloxy;

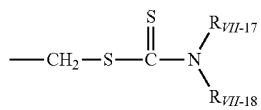

wherein R$_{VII-17}$ and R$_{VII-18}$ are independently selected from the group consisting of alkyl, cycloalkyl, alkenyl, alkynyl, aryl, heteroaryl and heterocyclyl;

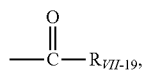

wherein R$_{VII-19}$ is selected from the group consisting of alkyl, cycloalkyl, alkenyl, alkynyl, aryl, heteroaryl, heterocyclyl, —SR$_{VII-20}$, —OR$_{VII-21}$, and BR$_{VII-22}$CO$_2$R$_{VII-23}$, wherein R$_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, R$_{VII-21}$ is selected from the group consisting of alkyl, alkenyl, alkynyl, aryl, heteroaryl, and heterocyclyl, R$_{VII-22}$ is selected from the group consisting of alkylene or arylene, and R$_{VII-23}$ is selected from the group consisting of alkyl, alkenyl, alkynyl, aryl, heteroaryl, and heterocyclyl;

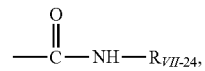

wherein R$_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

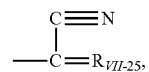

wherein R$_{VII-25}$ is heterocyclylidenyl;

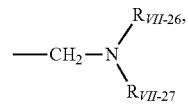

wherein R$_{VII-26}$ and R$_{VII-27}$ are independently selected from the group consisting of hydrogen, alkyl, cycloalkyl, alkenyl, alkynyl, aryl, heteroaryl, and heterocyclyl;

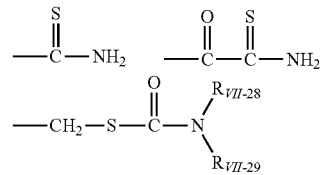

wherein R$_{VII-28}$ and R$_{VII-29}$ are independently selected from the group consisting of hydrogen, alkyl, cycloalkyl, alkenyl, alkynyl, aryl, heteroaryl, and heterocyclyl;

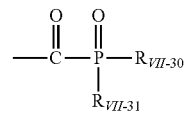

wherein R$_{VII-30}$ and R$_{VII-31}$ are independently alkoxy, alkenoxy, alkynoxy, aryloxy, heteroaryloxy, and heterocyclyloxy; and

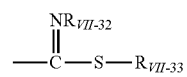

wherein $R_{VII-32}$ and $R_{VII-33}$ are independently selected from the group consisting of hydrogen, alkyl, cycloalkyl, alkenyl, alkynyl, aryl, heteroaryl, and heterocyclyl;

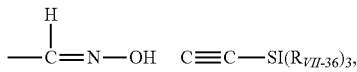

wherein $R_{VII-36}$ is selected from the group consisting of alkyl, alkenyl, aryl, heteroaryl and heterocyclyl;

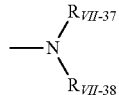

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

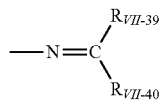

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

—N=$R_{VII-41}$, wherein $R_{VII-41}$ is heterocyclylidenyl;

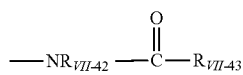

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

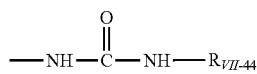

wherein $R_{VII-44}$ is selected from the group consisting of hydrogen, alkyl, cycloalkyl, alkenyl, alkynyl, aryl, heteroaryl and heterocyclyl;

—N=S—O;

—N=C=S;

—N=C=O;

—$N_3$;

—$SR_{VII-45}$ wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —$SR_{VII-46}$, and —$CH_2R_{VII-47}$, wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and

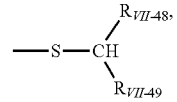

wherein $R_{VII-48}$ is selected from the group consisting of hydrogen, alkyl, cycloalkyl, alkenyl, alkynyl, aryl, heteroaryl and heterocyclyl, and $R_{VII-49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

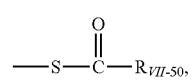

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

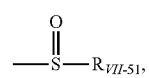

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

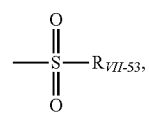

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII and their methods of manufacture are disclosed in PCT Publication No. WO 9941237-A1, which is incorporated herein by reference in its entirety for all purposes.

In a preferred embodiment, the CETP inhibitor of Formula VII is dimethyl 5,5-dithiobis[2-difluoromethyl-4-(2-methylpropyl)-6-(trifluoromethyl)-3-pyridine-carboxylate].

Another class of CETP inhibitors that finds utility with the present invention consists of substituted biphenyls having the Formula VIII

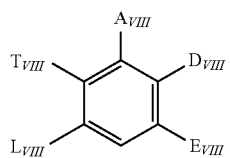

or a pharmaceutically acceptable salt, enantiomers, or stereoisomers thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VIII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula $R_{VIII-7}$—$X_{VIII}$— or

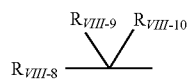

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$ and $R_{VIII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula VIII are disclosed in PCT Publication No. WO 9804528, which is incorporated herein by reference in its entirety for all purposes.

Another class of CETP inhibitors that finds utility with the present invention consists of substituted 1,2,4-triazoles having the Formula IX

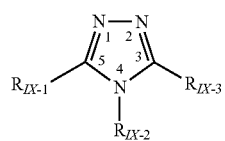

Formula IX or a pharmaceutically acceptable salt or tautomer thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is BSH.

Compounds of Formula IX and their methods of manufacture are disclosed in PCT Publication No. WO 9914204, which is incorporated herein by reference in its entirety for all purposes.

In a preferred embodiment, the CETP inhibitor is selected from the following compounds of Formula IX:

2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethyl phenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

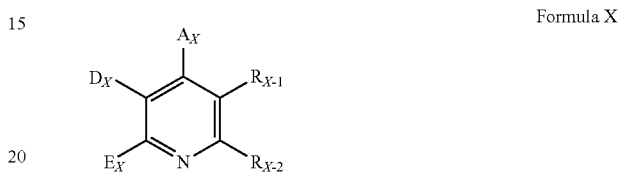

Formula X and pharmaceutically acceptable salts, enantiomers, or stereoisomers or N-oxides of said compounds;

in which $A_X$ represents cycloalkyl with 3 to 8 carbon atoms or a 5 to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula $BNR_{X-3}R_{X-4}$, in which $R_{X-3}$ and $R_{X-4}$ are identical or different and denote hydrogen, phenyl or straight-chain or branched alkyl having up to 6 carbon atoms, or $A_X$ represents a radical of the formula

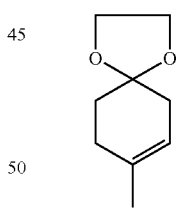

$D_X$ represents an aryl having 6 to 10 carbon atoms, that is optionally substituted by phenyl, nitro, halogen, trifluormethyl or trifluormethoxy, or it represents a radical of the formula $R_{X-5}-L_X$-,

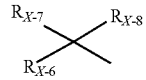

or $R_{X-9}-T_X-V_X-X_X$ in which $R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or O, and/or substituted by a group of the formula $BOR_{X-10}$, $-SR_{X-11}$, $SO_2R_{X-12}$ or $BNR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

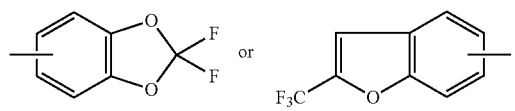

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula $BNR_{X-15}R_{X-16}$, in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula =O or =$NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_X$ and $X_X$ are identical or different and denote a straight chain or branched alkylene chain with up to 8 carbon atoms or $T_X$ or $X_X$ denotes a bond, $V_X$ represents an oxygen or sulfur atom or an $BNR_{X-18}$-group, in which $R_{X-18}$ denotes hydrogen or straight chain or branched alkyl with up to 6 carbon atoms or phenyl, $E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

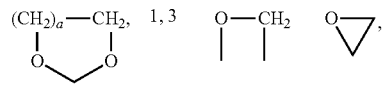

—$OR_{X-19}$ or 1,2

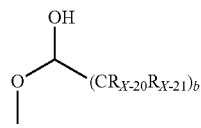

in which a and b are identical or different and denote a number equaling 1, 2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula $BOR_{X-22}$, in which $R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of trifluoromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifluoromethyl or trifluoromethoxy, and/or the formed carbocyclic rings are optionally substituted, also seminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

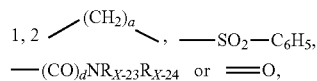

in which c denotes a number equaling 1, 2, 3, or 4, d denotes a number equaling 0 or 1, $R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

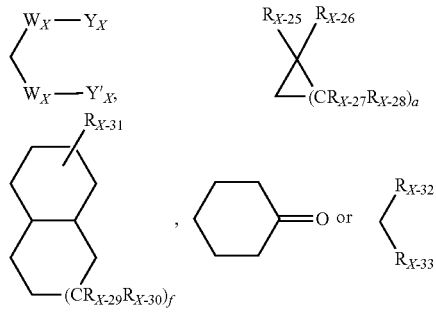

in which
$W_X$ denotes either an oxygen or a sulfur atom
$Y_X$ and $Y'_X$ together form a 2 to 6 membered straight chain or branched alkylene chain,
e denotes a number equaling 1, 2, 3, 4, 5, 6, or 7,
f denotes a number equaling 1 or 2,
$R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each, or
$R_{X-25}$ and $R_{X-26}$ or $R_{X-27}$ and $R_{X-28}$ respectively form together a straight chain or branched alkyl chain with up to 6 carbon atoms, or
$R_{X-25}$ and $R_{X-26}$ or $R_{X-27}$ and $R_{X-28}$ each together form a radical with the formula

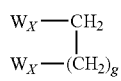

in which
$W_X$ has the meaning given above,
g denotes a number equaling 1, 2, 3, 4, 5, 6, or 7,
$R_{X-32}$ and $R_{X-33}$ form together a 3- to 7-membered heterocycle, which contains an oxygen or sulfur atom or a group with the formula SO, $SO_2$ or —$NR_{X-34}$,
in which
$R_{X-34}$ denotes hydrogen, phenyl, benzyl or straight or branched alkyl with up to 4 carbon atoms.

Compounds of Formula X and their methods of manufacture are disclosed in PCT Publication No. WO 9914215, which is incorporated herein by reference in its entirety for all purposes.

In a preferred embodiment, the CETP inhibitor is selected from the following compounds of Formula X:
2-cyclopentyl-5-hydroxy-7,7-dimethyl-4-(3-thienyl)-3-(4-trifluoromethylbenxoyl)-5,6,7,8-tetrahydroquinoline;
2-cyclopentl)-3-[fluoro-(4-trifluoromethylphenyl)methyl]-5-hydroxy-7,7-dimethyl-4-(3-thienyl)-5,6,7,8-tetrahydroquinoline; and
2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compound having the Formula XI

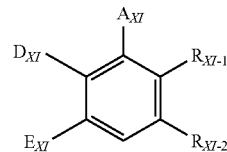

Formula XI and stereoisomers, stereoisomer mixtures, and salts thereof,
in which
$A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula —$NR_{XI-3}R_{XI-4}$,
in which
$R_{XI-3}$ and $R_{XI-4}$ are identical or different and denote hydrogen, phenyl, or straight-chain or branched alkyl with up to 6 carbon atoms
$D_{XI}$ stands for a radical of the formula

$R_{XI-5}$-$L_{XI}$,

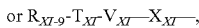
or $R_{XI-9}$-$T_{XI}$-$V_{XI}$—$X_{XI}$—, in which
$R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substitutedCin the case of the nitrogen-containing rings also via the N-function-Cup to 5-fold, identical or different, by halogen, trifluoromethyl. nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula —$OR_{XI-10}$, —$SR_{XI-11}$, —$SO_2R_{X-12}$ or —$NR_{XI-13}R_{XI-14}$,
in which
$R_{XI-10}$, $R_{XI-11}$ and $R_{XI-12}$, independent of each other, denote aryl with 6 to 10 carbon atoms, which itself is substituted up to 2-fold, identical or different, by phenyl, halogen or by straight-chain or branched alkyl with up to 6 carbon atoms,
$R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

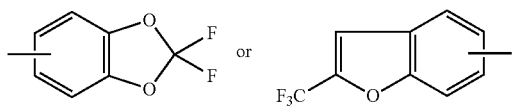

$R_{XI-7}$ denotes hydrogen, halogen or methyl, and $R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{X-16}$, in which $R_{XI-15}$ and $R_{XI-16}$ are identical or different and have the meaning given above for $R_{XI-3}$ and $R_{XI-4}$, or $R_{XI-7}$ and $R_{XI-8}$ together form a radical of the formula =O or =$NR_{XI-17}$, in which $R_{XI-17}$ denotes hydrogen or straight-chain or branched alkyl, alkoxy or acyl with up to 6 carbon atoms each, $L_{XI}$ denotes a straight-chain or branched alkylene- or alkenylene chain with up to 8 carbon atoms each, which is possibly substituted up to 2-fold by hydroxy, $T_{XI}$ and $X_{XI}$ are identical or different and denote a straight-chain or branched alkylene chain with up to 8 carbon atoms, or $T_{XI}$ and $X_{XI}$ denotes a bond, $V_{XI}$ stands for an oxygen- or sulfur atom or for an —$NR_{XI-18}$ group, in which $R_{XI-18}$ denotes hydrogen or straight-chain or branched alkyl with up to 6 carbon atoms, or phenyl, $E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl, $R_{XI-1}$ and $R_{XI-2}$ together form a straight-chain or branched alkylene chain with up to 7 carbon atoms, which must be substituted by a carbonyl group and/or by a radical of the formula

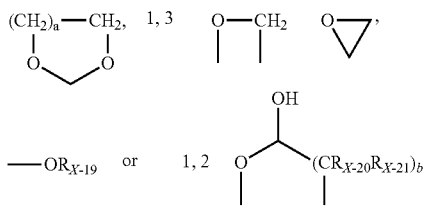

in which a and b are identical or different and denote a number 1, 2 or 3

$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$, in which $R_{XI-22}$ denotes straight-chain or branched acyl with up to 4 carbon atoms, or benzyl, or $R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms, $R_{XI-20}$ and $R_{XI-21}$ are identical or different, denoting hydrogen, phenyl or straight-chain or branched alkyl with up to 6 carbon atoms, or $R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different by hydroxyl, benzyloxy, trifluoromethyl, benzoyl, straight-chain or branched alkoxy, oxyacyl or carboxyl with up to 4 carbon atoms each, and/or phenyl— which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl—which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

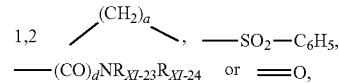

in which c denotes a number 1, 2, 3 or 4, d denotes a number 0 or 1, $R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold identical or different, by halogen, trifluoromethyl, cyano, phenyl or nitro, and/ or the alkylene chain formed by $R_{XI-1}$ and $R_{XI-2}$ is possibly substituted by a spiro-jointed radical of the formula

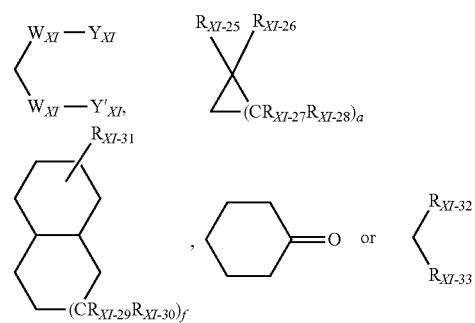

in which $W_{XI}$ denotes either an oxygen or a sulfur atom, $Y_{XI}$ and $Y'_{XI}$ together form a 2- to 6-membered straight-chain or branched alkylene chain, e is a number 1, 2, 3, 4, 5, 6 or 7, f denotes a number 1 or 2, $R_{XI-25}$, $R_{XI-26}$, $R_{XI-27}$, $R_{XI-28}$, $R_{XI-29}$, $R_{XI-30}$ and $R_{XI-31}$ are identical or different and denot hydrogen, trifluoromethyl, phenyl, halogen, or straight-chain or branched alkyl or alkoxy with up to 6 carbon atoms each, or $R_{XI-25}$ and $R_{XI-26}$ or $R_{XI-27}$ and $R_{XI-28}$ together form a straight-chain or branched alkyl chain with up to 6 carbon atoms, or $R_{XI-25}$ and $R_{XI-26}$ or $R_{XI-27}$ and $R_{XI-28}$ together form a radical of the formula $$\begin{array}{l} W_{XI} - CH_2 \\ \quad\quad\quad | \\ W_{XI} - (CH_2)_g \end{array}$$

in which $W_{XI}$ has the meaning given above, g is a number 1, 2, 3, 4, 5, 6 or 7, $R_{XI-32}$ and $R_{XI-33}$ together form a 3- to 7-membered heterocycle that contains an oxygen- or sulfur atom or a group of the formula SO, $SO_2$ or $-NR_{XI-34}$, in which $R_{XI-34}$ denotes hydrogen, phenyl, benzyl, or straight-chain or branched alkyl with up to 4 carbon atoms.

Compounds of Formula XI and their methods of manufacture are disclosed in PCT Publication No. WO 9914174, which is incorporated herein by reference in its entirety for all purposes.

Another class of CETP inhibitors that finds utility with the present invention consists of 2-aryl-substituted pyridines having the Formula (XII)

Formula XII

[Chemical structure of pyridine with substituents $A_{XII}$, $T_{XII}$, $D_{XII-1}$, $L_{XII}$, $E_{XII-2}$]

or pharmaceutically acceptable salts, enantiomers, or stereoisomers of said compounds, in which $A_{XII}$ and $E_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula $-NR_{XII-1}R_{XII-2}$, where $R_{XII-1}$ and $R_{XII-2}$ are identical or different and are meant to be hydrogen, phenyl or straight-chain or branched alkyl with up to 6 carbon atoms, $D_{XII}$ stands for straight-chain or branched alkyl with up to 8 carbon atoms, which is substituted by hydroxy, $L_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, $T_{XII}$ stands for a radical of the formula $R_{XII-3}-X_{XII}-$ or $$R_{XII-4} \diagdown \diagup^{R_{XII-5}\ R_{XII-6},}$$

where $R_{XII-3}$ and $R_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each or by phenyl, phenoxy or phenylthio which in turn can be substituted by halogen. trifluoromethyl or trifluoromethoxy, and/or where the cycles are possibly substituted by a group of the formula $-NR_{XII-7}R_{XII-8}$, where $R_{XII-7}$ and $R_{XII-8}$ are identical or different and have the meaning of $R_{XII-1}$ and $R_{XII-2}$ given above, $X_{XII}$ is a straight-chain or branched alkyl or alkenyl with 2 to 10 carbon atoms each, possibly substituted up to 2-fold by hydroxy or halogen, $R_{XII-5}$ stands for hydrogen, and $R_{XII-6}$ means to be hydrogen, halogen, mercapto, azido, trifluoromethyl, hydroxy, trifluoromethoxy, straight-chain or branched alkoxy with up to 5 carbon atoms, or a radical of the formula $BNR_{XII-9}R_{XII-10}$, where $R_{XII-9}$ and $R_{XII-10}$ are identical or different and have the meaning of $R_{XII-1}$ and $R_{XII-2}$ given above, or $R_{XII-5}$ and $R_{XII-6}$, together with the carbon atom, form a carbonyl group.

Compounds of Formula XII and their methods of manufacture are disclosed in EP 796846-A1, U.S. Pat. No. 6,127,383 and U.S. Pat. No. 5,925,645, all of which are incorporated herein by reference in their entireties for all purposes.

In a preferred embodiment, the CETP inhibitor is selected from the following compounds of Formula XII:

4,6-bis-(p-fluorophenyl)-2-isopropyl-3-[(p-trifluoromethyl phenyl)-(fluoro)-methyl]-5-(1-hydroxyethyl)pyridine;

2,4-bis-(4-fluorophenyl)-6-isopropyl-5-[4-(trifluoromethyl phenyl]-fluoromethyl]-3-hydroxymethyl)pyridine; and 2,4-bis-(4-fluorophenyl)-6-isopropyl-5-[2-(3-trifluoromethyl phenyl)vinyl]-3-hydroxymethyl)pyridine.

Another class of CETP inhibitors that finds utility with the present invention consists of compounds having the Formula (XIII)

Formula XIII

[Chemical structure of benzene ring with substituents $R_{XIII}$, $Y_{XIII}$, NH, $X_{XIII-1}$, S—$Z_{XIII}$, $X_{XIII-2}$, $X_{XIII-3}$, $X_{XIII-4}$]

or pharmaceutically acceptable salts, enantiomers, stereoisomers, hydrates, or solvates of said compounds, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}$, $X_{XIII-2}$, $X_{XIII-3}$, $X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or $BSO_2$—; and $Z_{XIII}$ is a hydrogen atom; or mercapto protective group.

Compounds of Formula XIII and their methods of manufacture are disclosed in PCT Publication No. WO 98/35937, which is incorporated herein by reference in its entirety for all purposes.

In a preferred embodiment, the CETP inhibitor is selected from the following compounds of Formula XIII:

N,N'-(dithiodi-2,1-phenylene)bis[2,2-dimethyl-propanamide];

N,N'-(dithiodi-2,1-phenylene)bis[1-methyl-cyclohexanecarboxamide];

N,N'-(dithiodi-2,1-phenylene)bis[1-(3-methylbutyl)-cyclopentanecarboxamide];

N,N'-(dithiodi-2,1-phenylene)bis[1-(3-methylbutyl)-cyclohexanecarboxamide];

N,N'-(dithiodi-2,1-phenylene)bis[1-(2-ethyl butyl)-cyclohexanecarboxamide];

N,N'-(dithiodi-2,1-phenylene)bis-tricyclo[3.3.1.1$^{3,7}$]decane-1-carboxamide;

propanethioic acid, 2-methyl-,S-[2[[[1-(2-ethyl butyl)cyclohexyl]carbonyl]amino]phenyl]ester;

propanethioic acid, 2,2-dimethyl-, S-[2-[[[1-(2-ethyl butyl)cyclohexyl]carbonyl]amino]phenyl]ester; and ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV Formula XIV

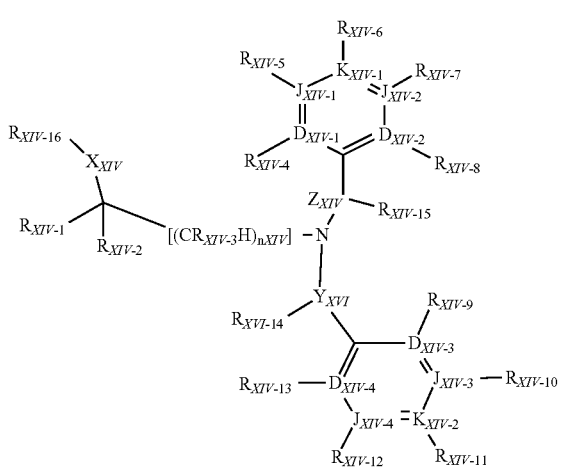

and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl,
perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl,
heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-4}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$ $J_{XIV-3}$, $J_{XIV-4}$ and $K_{XIV-2}$ must be a covalent bond with two of $D_{XIV-3}$, $D_{XIV-4}$, $J_{XIV-3}$, $J_{XIV-4}$ and $K_{XIV-2}$ are O and S, and no more than four of $D_{XIV-3}$, $D_4$, $J_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, aloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyt;

$Y_{XIV}$ is selected from a group consisting of a covalent single bond, $(C(R_{XIV-14})_2)_{qXIV}$ wherein $qXIV$ is an integer selected from 1 and 2 and $(CH(R_{XIV-14}))_{gXIV}$—$W_{XIV}$—$CH(R_{XIV-14}))_{pXIV}$ wherein $gXIV$ and $pXIV$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyi, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $qXIV-2$ is an integer selected from 1 and 2, $(CH(R_{XIV-15}))_{jXIV}$—W—$(CH(R_{XIV-15}))_{kXIV}$ wherein $jXIV$ and $kXIV$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is $(C(R_{XIV-15})_2)_{qXIV}$ wherein $qXIV$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsufonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is (CH$(R_{XIV-15}))_{jXIV}$—W—CH$(R_{XIV-15}))_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyt, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyaikyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$, and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV-4}$ and $R_{XIV-5}$, $R_{XIV-5}$ and $R_{XIV-6}$, $R_{XIV-6}$ and $R_{XIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$, and $R_{XIV-8}$ and $R_{XIV-13}$ is used at the same time.

Compounds of Formula XIV and their methods of manufacture are disclosed in PCT Publication No. WO 00/18721, which is incorporated herein by reference in its entirety for all purposes.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)-phenyl]methyl]amino]-1,1,1-trifluoro-2-propanol;
3-[[3-(3-isopropylphenoxy)phenyl][[3-(1,1,2,2-tetrafluoroethoxy)phenyl]-methyl]amino]-1,1,1-trifluoro-2-propanol;
3-[[3-(3-cyclopropyl phenoxy)phenyl][[3-(1,1,2,2-tetrafluoroethoxy)phenyl]-methyl]amino]-1,1,1-trifluro-2-propanol;
3-[[3-(3-(2-furyl)phenoxy)phenyl][[3-(1,1,2,2-tetrafluoroethoxy)phenyl]-methyl]amino]1,1,1-trifluoro-2-propanol;
3-[[3-(2,3-dichlorophenoxy)phenyl][[3-(1,1,2,2-tetrafluoroethoxy)phenyl]-methyl]amino]-1,1,1-trifluoro-2-propanol;
3-[[3-(4-fluorophenoxy)phenyl][[3-(1,1,2,2-tetrafluoroethoxy)phenyl]-methyl]amino]-1,1,1-trifluoro-2-propanol;
3-[[3-(4-methlylphenoxy)phenyl][[3-(1,1,2,2-tetrafluoroethoxy)phenyl]-methyl]amino]-1,1,1-trifluoro-2-propanol;
3-[[3-(2-fluoro-5-bromophenoxy)phenyl][[3-(1,1,2,2-tetrafluoroethoxy)phenyl]-methyl]amino]-1,1,1-trifluoro-2-propanol;
3-[[3-(4-chloro-3-ethylphenoxy)phenyl][[3-(1,1,2,2-tetrafluoroethoxy)phenyl]-methyl]amino]-1,1,1-trifluoro-2-propanol;
3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;
3-[[3-[3-(pentafluoroethyl)phenoxy]phenyl][[3-(1,1,2,2-tetrafluoroethoxy)-phenyl]methyl]amino]-1,1,1-trifluoro-2-propanol;
3-[[3-(3,5-dimethylphenoxy)phenyl][[3-(1,1,2,2-tetrafluoroethoxy)phenyl]-methyl]amino]-1,1,1-trifluoro-2-propanol;
3-[[3-(3-ethylphenoxy)phenyl][[3-(1,1,2,2-tetrafluoroethoxy)phenyl]-methyl]amino]-1,1,1-trifluoro-2-propanol;
3-[[3-(3-t-butylphenoxy)phenyl][[3-(1,1,2,2-tetrafluoroethoxy)phenyl]-methyl]amino]1,1,1-trifluoro-2-propanol;
3-[[3-(3-methylphenoxy)phenyl][[3-(1,1,2,2-tetrafluoroethoxy)phenyl]-methyl]amino]-1,1,1-trifluoro-2-propanol;
3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;
3-[[3-(phenoxy)phenyl][[3-(1,1,2,2-tetrafluoroethoxy)phenyl]methyl]amino]-1,1,1-trifluoro-2-propanol;
3-[[3-[3-(N,N-dimethylamino)phenoxy]phenyl][[3-(1,1,2,2-tetrafluoroethoxy)phenyl]methyl]amino]-1,1,1-trifluoro-2-propanol;
3-[[[3-(1,1,2,2-tetrafluoroethoxy)phenyl]methyl][3-[[3-(trifluoromethoxy)-phenyl]methoxy]phenyl]amino]-1,1,1-trifluoro-2-propanol;
3-[[[3-(1,1,2,2-tetrafluoroethoxy)phenyl]methyl][3-[[3-(trifluoromethyl)-phenyl]methoxy]phenyl]amino]-1,1,-trifluoro-2-propanol;
3-[[[3-(1,1,2,2-tetrafluoroethoxy)phenyl]methyl][3-[[3,5-dimethylphenyl]-methoxy]phenyl]amino]-1,1,1-trifluoro-2-propanol;
3-[[[3-(1,1,2,2-tetrafluoroethoxy)phenyl]methyl][3-[[3-(trifluoromethylthio)-phenyl]methoxy]phenyl]amino]-1,1,-trifluoro-2-propanol;
3-[[[3-(1,1,2,2-tetrafluoroethoxy)phenyl]methyl][3-[[3,5-difluorophenyl]-methoxy]phenyl]amino]-1,1,1-trifluoro-2-propanol;
3-[[[3-(1,2,2-tetrafluoroethoxy)phenyl]methyl][3-[cyclohexylmethoxy]-phenyl]amino]-1,1,1-trifluoro-2-propanol;
3-[[3-(2-difluoromethoxy-4-pyridyloxy)phenyl][[3-(1,1,2,2-tetrafluoroethoxy)-phenyl]methyl]amino]-1,1,1-trifluoro-2-propanol;
3-[[3-(2-trifluoromethyl-4-pyridyloxy)phenyl][[3-(1,1,1-tetrafluoroethoxy)-phenyl]methyl]amino]-1,1,1-trifluoro-2-propanol;
3-[[3-(3-difluoromethoxyphenoxy)phenyl][[3-(1,1,2,2-tetrafluoroethoxy)-phenyl]methyl]amino]-1,1,1-trifluoro-2-propanol;
3-[[[3-(3-trifluoromethylthio)phenoxy]phenyl][[3-(1,1,2,2-tetrafluoroethoxy)-phenyl]methyl]amino]-1,1,1-trifluoro-2-propanol;
3-[[3-(4-chloro-3-trifluoromethylphenoxy)phenyl][[3-(1,1,2,2-tetrafluoroethoxy)-phenyl]methyl]amino]-1,1,1,-trifluoro-2-propanol;
3-[[3-(3-trifluoromethoxyphenoxy)phenyl][[3-(pentafluoroethymethyl]amino]-1,1,1-trifluoro-2-propanol;
3-[[3-(3-isopropyl phenoxy)phenyl][[3-(pentafluoroethyl)phenyl]methyl]-amino]-1,1,1-trifluoro-2-propanol;
3-[[3-(3-cyclopropylphenoxy)phenyl][[3-(pentafluoroethyl)phenyl]methyl]-amino]-1,1,1-trifluoro-2-propanol;
3-[[3-(3-(2-furyl)phenoxy)phenyl][[3-(pentafluoroethyl)phenyl]methyl]-amino]-1,1,1-trifluoro-2-propanol;
3-[[3-(2,3-dichlorophenoxy)phenyl][[3-(pentafluoroethyl)phenyl]methyl]-amino]-1,1,1-trifluoro-2-propanol;
3-[[3-(4-fluorophenoxy)phenyl][[3-(pentafluoroethyl)phenyl]methyl]amino]-1,1,1-trifluoro-2-propanol;
3-[[3-(4-methylphenoxy)phenyl][[3-(pentafluoroethyl)phenyl]methyl]amino]-1,1,1-trifluoro-2-propanol;
3-[[3-(2-fluoro-5-bromophenoxy)phenyl][[3-(pentafluoroethyl)phenyl]methyl]-amino]-1,1,1-trifluoro-2-propanol;
3-[[3-(4-chloro-3-ethylphenoxy)phenyl][[3-(pentafluoroethyl)phenyl]methyl]-amino]-1,1,1-trifluoro-2-propanol;
3-[[3-[3-(1,1,2,2-tetrafluoroethoxy)phenoxy]phenyl][[3-(pentafluoroethyl)-phenyl]methyl]amino]-1,1,1-trifluoro-2-propanol;
3-[[3-[3-(pentafluoroethyl)phenoxy]phenyl][[3-(pentafluoroethyl)phenyl]-methyl]amino]-1,1,1-trifluoro-2-propanol;
3-[[3-(3,5-dimethylphenoxy)phenyl][[3-(pentafluoroethyl)phenyl]methyl]-amino]-1,1,1-trifluoro-2-propanol;
3-[[3-(3-ethylphenoxy)phenyl][[3-(pentafluoroethyl)phenyl]methyl]amino]-1,1,-trifluoro-2-propanol;

3-[[3-(3-t-butyl phenoxy)phenyl][[3-(pentafluoroethyl)phenyl]methyl]amino]-1,1,1-trifluoro-2-propanol;
3-[[3-(3-methylphenoxy)phenyl][[3-pentafluoroethyl)phenyl]methyl]amino]-1,1,1-trifluoro-2-propanol;
3-[[3-(5,6,7,8-tetrahydro-2-naphthoxy)phenyl][[3-(pentafluoroethyl)phenyl]-methyl]amino]-1,1,1-trifluoro-2-propanol;
3-[[3-(phenoxy)phenyl][[3-(pentafluoroethyl)phenyl]methyl]amino]-1,1,1-trifluoro-2-propanol;
3-[[3-[3-(N,N-dimethylamino)phenoxy]phenyl][[3-(pentafluoroethyl)phenyl]-methyl]amino]-1,1,1-trifluoro-2-propanol;
3-[[[3-(pentafluoroethyl)phenyl]methyl][3-[[3-(trifluoromethoxy)phenyl]-methoxy]phenyl]amino]amino]-1,1,1-trifluoro-2-propanol;
3-[[[3-(pentafluoroethyl)phenyl]methyl][3-[[3-(trifluoromethyl)phenyl]-methoxy]phenyl]amino]-1,1,1-trifluoro-2-propanol;
3-[[[3-(pentafluoroethyl)phenyl]methyl][3-[[3,5-dimethyphenyl]methoxy]-phenyl]amino]-1,1,1-trifluoro-2-propanol;
3-[[[3-(pentafluoroethyl)phenyl]methyl][3-[[3-(trifluoromethylthio)phenyl]-methoxy]phenyl]amino]-1,1,1-trifluoro-2-propanol;
3-[[[3-(pentafluoroethyl)phenyl]methyl][3-[[3,5-difluorophenyl]methoxy]-phenyl]amino]-1,1,1-trifluoro-2-propanol;
3-[[[3-(pentafluoroethyl)phenyl]methyl][3-[cyclohexylmethoxy]phenyl]-amino]-1,1,1-trifluoro-2-propanol;
3-[[3-(2-difluoromethoxy-4-pyridyloxy)phenyl][[3-(pentafluoroethyl)phenyl]-methyl]amino]-1,1,1-trifluoro-2-propanol;
3-[[3-(2-trifluoromethyl-4-pyridyloxy)phenyl][[3-(pentafluoroethyl)phenyl]-methyl]amino]-1,1,1-trifluoro-2-propanol;
3-[[3-(3-difluoromethoxyphenoxy)phenyl][[3-(pentafluoroethyl)phenyl]-methyl]amino]-1,1,1-trifluoro-2-propanol;
3-[[[3-(3-trifluoromethylthio)phenoxy]phenyl][[3-(pentafluoroethyl)phenyl]-methyl]amino]-1,1,1-trifluoro-2-propanol;
3-[[3-(4-chloro-3-trifluoromethylphenoxy)phenyl][[3-(pentafluoroethyl)-phenyl]methyl]amino]-1,1,1-trifluoro-2-propanol;
3-[[3-(3-trifluoromethoxyphenoxy)phenyl][[3-(heptafluoropropyl)phenyl]-methyl]amino]-1,1,1-trifluoro-2-propanol;
3-[[3-(3-isopropylphenoxy)phenyl][[3-(heptafluoropropyl)phenyl]methyl]-amino]-1,1,1-trifluoro-2-propanol;
3-[[3-(3-cyclopropylphenoxy)phenyl][[3-(heptafluoropropyl)phenyl]methyl]-amino]-1,1,1-trifluoro-2-propanol;
3-[[3-(3-(2-furyl)phenoxy)phenyl][[3-(heptafluoropropyl)phenyl]methyl]-amino]-1,1,1-trifluoro-2-propanol;
3-[[3-(2,3-dichlorophenoxy)phenyl][[3-(heptafluoropropyl)phenyl]methyl]-amino]-1,1,1-trifluoro-2-propanol;
3-[[3-(4-fluorophenoxy)phenyl][[3-(heptafluoropropyl)phenyl]methyl]amino]-1,1,1-trifluoro-2-propanol;
3-[[3-(4-methylphenoxy)phenyl][[3-(heptafluoropropyl)phenyl]methyl]amino]-1,1,1-trifluoro-2-propanol;
3-[[3-(2-fluoro-5-bromophenoxy)phenyl][[3-(heptafluoropropyl)phenyl]methyl]amino]-1,1,1-trifluoro-2-propanol;
3-[[3-(4-chloro-3-ethylphenoxy)phenyl][[3-(heptafluoropropyl)phenyl]methyl]amino]-1,1,1-trifluoro-2-propanol;
3-[[3-[3-(1,1,2,2-tetrafluoroethoxy)phenoxy]phenyl][[3-(heptafluoropropyl)-phenyl]methyl]amino]-1,1,1-trifluoro-2-propanol;
3-[[3-(pentafluoroethyl)phenoxy]phenyl][[3-(heptafluoropropyl)phenyl]-methyl]amino]-1,1,1-trifluoro-2-propanol;
3-[[3-(3,5-dimethylphenoxy)phenyl][[3-(heptafluoropropyl)phenyl]methyl]-amino]-1,1,1-trifluoro-2-propanol;
3-[[3-(3-ethylphenoxy)phenyl][[3-(heptafluoropropyl)phenyl]methyl]amino]-1,1,1-trifluoro-2-propanol;
3-[[3-(3-t-butylphenoxy)phenyl][[3-(heptafluoropropyl)phenyl]methyl]amino]-1,1,1-trifluoro-2-propanol;
3-[[3-(3-methylphenoxy)phenyl][[3-(heptafluoropropyl)phenyl]methyl]amino]-1,1,1-trifluoro-2-propanol;
3-[[3-(5,6,7,8-tetrahydro-2-naphthoxy)phenyl][[3-(heptafluoropropyl)phenyl]-methyl]amino]-1,1,1-trifluoro-2-propanol;
3-[[3-(phenoxy)phenyl][[3-(heptafluoropropyl)phenyl]methyl]amino]-1,1,1-trifluoro-2-propanol;
3-[[3-[3-(N,N-dimethylamino)phenoxy]phenyl][[3-(heptafluoropropyl)phenyl]-methyl]amino]-1,1,1-trifluoro-2-propanol;
3-[[[3-(heptafluoropropyl)phenyl]methyl][3-[[3-(trifluoromethoxy)phenyl]-methoxy]phenyl]amino]-1,1,1-trifluoro-2-propanol;
3-[[[3-(heptafluoropropyl)phenyl]methyl][3-[[3-(trifluoromethyl)phenyl]-methoxy]phenyl]amino]-1,1,1-trifluoro-2-propanol;
3-[[[3-(heptafluoropropyl)phenyl]methyl][3-[[3,5-dimethylphenyl]methoxy]-phenyl]amino]-1,1,1-trifluoro-2-propanol;
3-[[[3-(heptafluoropropyl)phenyl]methyl][3-[[3-(trifluoromethylthio)phenyl]-methoxy]phenyl]amino]-1,1,1-trifluoro-2-propanol;
3-[[[3-(heptafluoropropyl)phenyl]methyl][3-[[3,5-difluorophenyl]methoxy]-phenyl]amino]-1,1,1-trifluoro-2-propanol;
3-[[[3-(heptafluoropropyl)phenyl]methyl][3-[cyclohexylmethoxy]phenyl]-amino]-1,1,1-trifluoro-2-propanol;
3-[[3-(2-difluoromethoxy-4-pyridyloxy)phenyl][[3-(heptafluoropropyl)phenyl]-methyl]amino]-1,1,1-trifluoro-2-propanol;
3-[[3-(2-trifluoromethyl-4-pyridyloxy)phenyl][[3-(heptafluoropropyl)phenyl]-methyl]amino]-1,1,1-trifluoro-2-propanol;
3-[[3-(3-difluoromethoxyphenoxy)phenyl][[3-(heptafluoropropyl)phenyl]-methyl]amino]-1,1,1-trifluoro-2-propanol;
3-[[[3-(3-trifluoromethylthio)phenoxy]phenyl][[3-(heptafluoropropyl)phenyl]-methyl]amino]-1,1,1-trifluoro-2-propanol;
3-[[3-(4-chloro-3-trifluoromethylphenoxy)phenyl][[3-(heptafluoropropyl)-phenyl]-methyl]amino]-1,1,1-trifluoro-2-propanol;
3-[[3-(3-trifluoromethoxyphenoxy)phenyl][[2-fluoro-5-(trifluoromethyl)-phenyl]-methyl]amino]-1,1,1-trifluoro-2-propanol;
3-[[3-(3-isopropylphenoxy)phenyl][[2-fluoro-5-(trifluoromethyl)phenyl]-methyl]amino]1,1,1-trifluoro-2-propanol;
3-[[3-(3-cyclopropylphenoxy)phenyl][[2-fluoro-5-(trifluoromethyl)phenyl]-methyl]amino]-1,1,1-trifluoro-2-propanol;
3-[[3-(3-(2-furyl)phenoxy)phenyl][[2-fluoro-5-(trifluoromethyl)phenyl]-methyl]amino]-1,1,1-trifluoro-2-propanol;
3-[[3-(2,3-dichlorophenoxy)phenyl][[2-fluoro-5-(trifluoromethyl)phenyl]-methyl]amino]-1,1,1-trifluoro-2-propanol;
3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;
3-[[3-(2-fluoro-5-bromophenoxy)phenyl][[2-fluoro-5-(trifluoromethyl)-phenyl]methyl]amino]-1,1,1-trifluoro-2-propanol;
3-[[3-(4-chloro-3-ethylphenoxy)phenyl][[2-fluoro-5-(trifluoromethyl)-phenyl]methyl]amino]-1,1,1-trifluoro-2-propanol;
3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
3-[[3-[3-(pentafluoroethyl)phenoxy]phenyl][[2-fluoro-5-(trifluoromethyl)-phenyl]-methyl]amino]-1,1,1-trifluoro-2-propanol;
3-[[3-(3,5-dimethylphenoxy)phenyl][[2-fluoro-5-(trifluoromethyl)phenyl]-methyl]amino]-1,1,1-trifluoro-2-propanol;
3-[[3-(3-ethylphenoxy)phenyl][[2-fluoro-5-(trifluoromethyl)phenyl]methyl-amino]-1,1,1-trifluoro-2-propanol;
3-[[3-(3-t-butylphenoxy)phenyl][[2-fluoro-5-(trifluoromethyl)phenyl]methyl]-amino]-1,1,1-trifluoro-2-propanol;
3-[[3-(3-methylphenoxy)phenyl][[2-fluoro-5-(trifluoromethyl)phenyl]methyl]-amino]-1,1,1-trifluoro-2-propanol;
3-[[3-(5,6,7,8-tetrahydro-2-naphthoxy)phenyl][[2-fluoro-5-(trifluoromethyl)-phenyl]methyl]amino]-1,1,1-trifluoro-2-propanol;
3-[[3-(phenoxy)phenyl][[2-fluoro-5-(trifluoromethyl)phenyl]methyl]amino]-1,1,1-trifluoro-2-propanol;
3-[[3-[3-(N,N-dimethylamino)phenoxy]phenyl][[2-fluoro-5-(trifluoromethyl)-phenyl]methyl]amino]-1,1,1-trifluoro-2-propanol;
3-[[[2-fluoro-5-(trifluoromethyl)phenyl]methyl][3-[[3-(trifluoromethoxy)-phenyl]methoxy]phenyl]amino]-1,1,1-trifluoro-2-propanol;
3-[[[2-fluoro-5-(trifluoromethyl)phenyl]methyl][3-[[3-(trifluoromethyl)-phenyl]methoxy]phenyl]amino]-1,1,1-trifluoro-2-propanol;
3-[[[2-fluoro-5-(trifluoromethyl)phenyl]methyl][3-[[3,5-dimethylphenyl]-methoxy]phenyl]amino]-1,1,1-trifluoro-2-propanol;
3-[[[2-fluoro-5-(trifluoromethyl)phenyl]methyl][3-[[3-(trifluoromethylthio)-phenyl]methoxy]phenyl]amino]-1,1,1-trifluoro-2-propanol;
3-[[[2-fluoro-5-(trifluoromethyl)phenyl]methyl][3-[[3,5-difluorophenyl]-methoxy]phenyl]amino]-1,1,1-trifluoro-2-propanol;
3-[[[2-fluoro-5-(trifluoromethyl)phenyl]methyl][3-[cyclohexylmethoxy]-phenyl]amino]-1,1,1-trifluoro-2-propanol;
3-[[3-(2-difluoromethoxy-4-pyridyloxy)phenyl][[2-fluoro-5-(trifluoromethyl)-phenyl]methyl]amino]-1,1,1-trifluoro-2-propanol;
3-[[3-(2-trifluoromethyl-4-pyridyioxy)phenyl][[2-fluoro-5-(trifluoromethyl)-phenyl]methyl]amino]-1,1,1-trifluoro-2-propanol;
3-[[3-(3-difluoromethoxyphenoxy)phenyl][[2-fluoro-5-(trifluoromethyl)-phenyl]methyl]amino]-1,1,1-trifluoro-2-propanol;
3-[[[3-(3-trifluoromethylthio)phenoxy]phenyl][[2-fluoro-5-(trifluoromethyl)-phenyl]methyl]amino]-1,1,1-trifluoro-2-propanol;
3-[[3-(4-chloro-3-trifluoromethylphenoxy)phenyl][[2-fluoro-5-(trifluoromethyl)phenyl]methyl]amino]-1,1,1-trifluoro-2-propanol;
3-[[3-(3-trifluoromethoxyphenoxy)phenyl][[2-fluoro-4-(trifluoromethyl)-phenyl]methyl]amino]-trifluoro-2-propanol;
3-[[3-(3-isopropylphenoxy)phenyl][[2-fluoro-4-(trifluoromethyl)phenyl]-methyl]amino]-1,1,1-trifluoro-2-propanol;
3-[[3-(3-cyclopropylphenoxy)phenyl][[2-fluoro-4-(trifluoromethyl)phenyl]-methyl]amino]-1,1,1-trifluoro-2-propanol;
3-[[3-(3-(2-furyl)phenoxy)phenyl][[2-fluoro-4-(trifluoromethyl)phenyl]-methyl]amino]-1,1,1-trifluoro-2-propanol;
3-[[3-(2,3-dichlorophenoxy)phenyl][[2-fluoro-4-(trifluoromethyl)phenyl]-methyl]amino]-1,1,1-trifluoro-2-propanol;
3-[[3-(4-fluorophenoxy)phenyl][[2-fluoro-4-(trifluoromethyl)phenyl]-methyl]amino]-1,1,1-trifluoro-2-propanol;
3-[[3-(4-methylphenoxy)phenyl][[2-fluoro-4-(trifluoromethyl)phenyl]-methyl]amino]-1,1,1-trifluoro-2-propanol;
3-[[3-(2-fluoro-5-bromophenoxy)phenyl][[2-fluoro-4-(trifluoromethyl)phenyl]methyl]amino]-1,1,1-trifluoro-2-propanol;
3-[[3-(4-chloro-3-ethylphenoxy)phenyl][[2-fluoro-4-(trifluoromethyl)phenyl]methyl]amino]-1,1,1-trifluoro-2-propanol;
3-[[3-[3-(1,1,2,2-tetrafluoroethoxy)phenoxy]phenyl][[2-fluoro-4-(trifluoro-methyl)phenyl]methyl]amino]-1,1,1-trifluoro-2-propanol;
3-[[3-[3-(pentafluoroethyl)phenoxy]phenyl][[2-fluoro-4-(trifluoromethyl)-phenyl]methyl]amino]-1,1,1-trifluoro-2-propanol;
3-[[3-(3,5-dimethylphenoxy)phenyl][[2-fluoro-4-(trifluoromethyl)phenyl]-methyl]amino]-1,1,1-trifluoro-2-propanol;
3-[[3-(3-ethylphenoxy)phenyl][[2-fluoro-4-(trifluoromethyl)phenyl]methyl]-amino]-1,1,1-trifluoro-2-propanol;
3-[[3-(3-t-butylphenoxy)phenyl][[2-fluoro-4-(trifluoromethyl)phenyl]methyl]-amino]-1,1,1-trifluoro-2-propanol;
3-[[3-(3-methylphenoxy)phenyl][[2-fluoro-4-(trifluoromethyl)phenyl]methyl]-amino]-1,1,1-trifluoro-2-propanol;
3-[[3-(5,6,7,8-tetrahydro-2-naphthoxy)phenyl][[2-fluoro-4-(trifluoromethyl)-phenyl]methyl]amino]-1,1,1-trifluoro-2-propanol;
3-[[3-(phenoxy)phenyl][[2-fluoro-4-(trifluoromethyl)phenyl]methyl]amino]-1,1,1-trifluoro-2-propanol;
3-[[3-[3-(N,N-dimethylamino)phenoxy]phenyl][[2-fluoro-4-(trifluoromethyl)-phenyl]methyl]amino]-1,1,1-trifluoro-2-propanol;
3-[[[2-fluoro-4-(trifluoromethyl)phenyl]methyl][3-[[3-(trifluoromethoxy)-phenyl]methoxy]phenyl]amino]-1,1,1-trifluoro-2-propanol;
3-[[[2-fluoro-4-(trifluoromethyl)phenyl]methyl][3-[[3-(trifluoromethyl)-phenyl]methoxy]phenyl]amino]-1,1,1-trifluoro-2-propanol;
3-[[[2-fluoro-4-(trifluoromethyl)phenyl]methyl][3-[[3,5-dimethylphenyl]-methoxy]phenyl]amino]-1,1,1-trifluoro-2-propanol;
3-[[[2-fluoro-4-(trifluoromethyl)phenyl]methyl][3-[[3-(trifluoromethylthio)-phenyl]methoxy]phenyl]amino]-1,1,1-trifluoro-2-propanol;
3-[[[2-fluoro-4-(trifluoromethyl)phenyl]methyl][3-[[3,5-difluorophenyl]-methoxy]phenyl]amino]-1,1,1-trifluoro-2-propanol;
3-[[[2-fluoro-4-(trifluoromethyl)phenyl]methyl][3-[cyclohexylmethoxy]-phenyl]amino]-1,1,1-trifluoro-2-propanol;
3-[[3-(2-difluoromethoxy-4-pyridyloxy)phenyl][[2-fluoro-4-(trifluoromethyl)-phenyl]methyl]amino]-1,1,1-trifluoro-2-propanol;
3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(tri-fluoromethyl)-phenyl]methyl]amino]-1,1,1-trifluoro-2-propanol;

3-[[[3-(3-trifluoromethylthio)phenoxy]phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoro-methyl)phenyl]methyl]amino]-1,1,1-trifluoro-2-propanol.

Another class of CETP inhibitors that finds utility with the present invention consists of substitued N-Aliphatic-N-Aromatic tertiary-Heteroalkylamines having the Formula XV

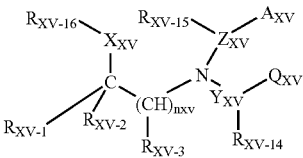

and pharmaceutically acceptable forms thereof, wherein:

$n_{XV}$ is an integer selected from 1 through 2;

$A_{XV}$ and $Q_{XV}$ are independently selected from the group consisting of —CH$_2$(CR$_{XV-37}$R$_{XV-38}$)$_{vXV}$—(CR$_{XV-33}$R$_{XV-34}$)$_{uXV}$-T$_{XV}$-(CR$_{XV-35}$R$_{XV-36}$)$_{wXV}$-H,

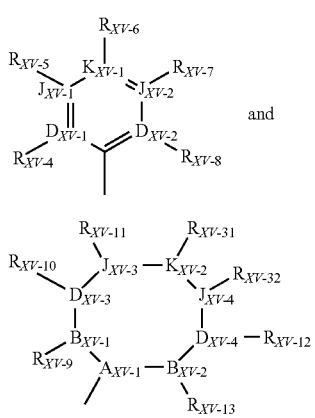

with the provisos that one of $A_{XV}$ and $Q_{XV}$ must be AQ-1 and that one of $A_{XV}$ and $Q_{XV}$ must be selected from the group consisting of AQ-2 and —CH$_2$(CR$_{XV-37}$R$_{XV-38}$)$_{vXV}$—(CR$_{XV-33}$R$_{XV-34}$)$_{uXV}$-T$_{XV}$-(CR$_{XV-35}$R$_{XV-36}$)$_{wXV}$—H;

$T_{XV}$ is selected from the group consisting of a single covalent bond, O, S, S(O), S(O)$_2$, C(R$_{XV-33}$)═C(R$_{XV-35}$), and C≡C;

$v_{XV}$ is an integer selected from 0 through 1 with the proviso that $v_{XV}$ is 1 when any one of R$_{XV-33}$, R$_{XV-34}$, R$_{XV-35}$, and R$_{XV-36}$ is aryl or heteroaryl;

$u_{XV}$ and $w_{XV}$ are integers independently selected from 0 through 6;

$A_{XV-1}$ is C(R$_{XV-30}$);

D$_{XV-1}$, D$_{XV-2}$, J$_{XV-1}$, J$_{XV-2}$, and K$_{XV-1}$, are independently selected from the group consisting of C, N, O, S and a covalent bond with the provisos that no more than one of D$_{XV-1}$, D$_{XV-2}$, J$_{XV-1}$, J$_{XV-2}$, and K$_{XV-1}$ is a covalent bond, no more than one of D$_{XV-1}$, D$_{XV-2}$ J$_{XV-1}$, J$_{XV-2}$, and K$_{XV-1}$ is O, no more than one of D$_{XV-1}$, D$_{XV-2}$, J$_{XV-1}$, J$_{XV-2}$, and K$_{XV-1}$ is S, one of D$_{XV-1}$ D$_{XV-2}$, J$_{XV-1}$, J$_{XV-2}$, and K$_{XV-1}$ must be a covalent bond when two of D$_{XV-1}$, D$_{XV-2}$, J$_{XV-1}$, J$_{XV-2}$, and K$_{XV-1}$ are O and S, and no more than four of D$_{XV-1}$, D$_{XV-2}$, J$_{XV-1}$, J$_{XV-2}$ and K$_{XV-1}$ are N;

B$_{XV-1}$, B$_{XV-}$2, D$_{XV-3}$, D$_{XV-4}$, J$_{XV-3}$, J$_{XV-4}$, and K$_{XV-2}$ are independently selected from the group consisting of C, C(R$_{XV-30}$), N, O, S and a covalent bond with the provisos that no more than 5 of B$_{XV-1}$, B$_{XV-2}$, D$_{XV-3}$. D$_{XV-4}$, J$_{XV-3}$, J$_{XV-4}$, and K$_{XV-2}$ are a covalent bond, no more than two of B$_{XV-1}$, B$_{XV-2}$, D$_{XV-3}$, D$_{XV-4}$, J$_{XV-3}$, J$_{XV-4}$, and K$_{XV-2}$ are O, no more than two of B$_{XV-1}$, B$_{XV-2}$, D$_{XV-3}$, D$_{XV-4}$, J$_{XV-3}$, J$_{XV-4}$, and K$_{XV-2}$ and S, no more than two of B$_{XV-1}$, B$_{XV-2}$, D$_{XV-3}$, D$_{XV-4}$, J$_{XV-3}$, J$_{XV-4}$, and K$_{XV-2}$ are simultaneously O and S, and no more than two of B$_{XV-1}$, B$_{XV-2}$, D$_{XV-3}$, D$_{XV-4}$, J$_{XV-3}$, J$_{XV-4}$, and K$_{XV-2}$ are N;

B$_{XV-1}$ and D$_{XV-3}$, D$_{XV-}$3 and J$_{XV-3}$, J$_{XV-4}$ and K$_{XV-2}$, K$_{XV-2}$ and J$_{XV-4}$, J$_{XV-4}$ and D$_{XV-4}$, and D$_{XV-4}$ and B$_{XV-2}$ are independently selected to form an in-ring spacer pair wherein said spacer pair is selected from the group consisting of C(R$_{XV-33}$)═C(R$_{XV-35}$) and N═N with the provisos that AQ-2 must be a ring of at least five contiguous members, that no more than two of the group of said spacer pairs are simultaneously C(R$_{XV-33}$)═C(R$_{XV-35}$) and that no more than one of the group of said spacer pairs can be N═N unless the other spacer pairs are other than C(R$_{XV-33}$)═C(R$_{XV-35}$) O, N, and S;

R$_{XV-1}$ is selected from the group consisting of haloalkyl and haloalkoxymethyl;

R$_{XV-2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

R$_{XV-3}$ is selected from the group consisting of hydrido, aryl, alkyl, alkenyl, haloalkyl, and haloalkoxyalkyl;

Y$_{XV}$ is selected from the group consisting of a covalent single bond, (CH$_2$)$_q$ wherein q is an integer selected from 1 through 2 and (CH$_2$)$_j$—O—(CH$_2$)$_k$ wherein j and k are integers independently selected from 0 through 1;

Z$_{XV}$ is selected from the group consisting of covalent single bond, (CH$_2$)$_q$ wherein q is an integer selected from 1 through 2, and (CH$_2$)$_j$—O—(CH$_2$)$_k$ wherein j and k are integers independently selected from 0 through 1;

R$_{XV-4}$, R$_{XV-9}$ and R$_{XV-13}$ are independently selected from the group consisting of hydrido, halo, haloalkyl, and alkyl;

R$_{XV-30}$ is selected from the group consisting of hydrido, alkoxy, alkoxyalkyl, halo, haloalkyl, alkylamino, alkylthio, alkylthioalkyl, alkyl, alkenyl, haloalkoxy, and haloalkoxyalkyl with the proviso that R$_{XV-30}$ is selected to maintain the tetravalent nature of carbon, trivalent nature of nitrogen, the divalent nature of sulfur, and the divalent nature of oxygen;

R$_{XV-30}$, when bonded to A$_{XV-1}$, is taken together to form an intra-ring linear spacer connecting the A$_{XV-1}$-carbon at the point of attachment of R$_{XV-30}$ to the point of bonding of a group selected from the group consisting of R$_{XV-10}$, R$_{XV-11}$, R$_{XX-12}$, R$_{XV-31}$, and R$_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

R$_{XV-30}$, when bonded to A$_{XV-1}$, is taken together to form an intra-ring branched spacer connecting the A$_{XV-1}$-carbon at the point of attachment of R$_{XV-30}$ to the points of bonding of each member of any one of substituent pairs selected from the group consisting of substituitent pairs R$_{XV-10}$ and R$_{XV-11}$, R$_{XV-10}$ and R$_{XV-31}$, R$_{XV-10}$ and R$_{XV-32}$, R$_{XV-10}$ and R$_{XV-12}$, R$_{XV-11}$ and R$_{XV-31}$, R$_{XV-11}$ and R$_{XV-32}$, R$_{XV-11}$ and R$_{XV-12}$, $R_{XV-31}$ and $R_{XV}$-32. $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkylamidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are each independently simultaneously oxo, and that $R_{XV-9}$, $R_{XV-10}$, $R_{XV-11}$, $R_{XV-12}$, $R_{XV-13}$, $R_{XV-31}$, and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV}$-5 and $R_{XV-6}$, $R_{XV-6}$ and $R_{XV-7}$, $R_{XV-7}$ and $R_{XV-8}$, $R_{XV-9}$ and $R_{XV-10}$, and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$, $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV and their methods of manufacture are disclosed in PCT Publication No. WO 00/18723, which is incorporated herein by reference in its entirety for all purposes.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;

3-[[3-(4-chloro-3-ethylphenoxy)phenyl](cyclopentylmethyl)amino]-1,1,1-trifluoro-2-propanol;

3-[[3-(4-chloro-3-ethyl phenoxy)phenyl](cyclopropylmethyl)amino]-1,1,1-trifluoro-2-propanol;

3-[[3-(4-chloro-3-ethyl phenoxy)phenyl][(3-trifluoromethyl)cyclohexyl-methyl]amino]-1,1,1-trifluoro-2-propanol;

3-[[3-(4-chloro-3-ethyl phenoxy)phenyl][(3-pentafluoroethyl)cyclohexyl-methyl]amino]-1,1,1-trifluoro-2-propanol;

3-[[3-(4-chloro-3-ethyl phenoxy)phenyl][(3-trifluoromethoxy)cyclohexyl-methyl]amino]-1,1,1-trifluoro-2-propanol;

3-[[3-(4-chloro-3-ethylphenoxy)phenyl][[3-(1,1,2,2-tetrafluoroethoxy)cyclo-hexylmethyl]amino]-1,1,1-trifluoro-2-propanol;

3-[[3-(3-trifuoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl][(3-pentafluoroethyl)cyclohexy-methyl]amino]-1,1,1-trifluoro-2-propanol;
3-[[3-(3-trifuoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropyl phenoxy)phenyl](cyclohexylmethyl]amino]-1,1,1-trifluoro-2-propanol:
3-[[3-(3-isopropylphenoxy)phenyl](cyclopentylmethyl]amino]-1,1,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexyl-methyl]amino]-1,1,1-trifluoro-2-propanol;
3-[[3-(3-isopropylphenoxy)phenyl][(3-pentafluoroethyl)cyclohexyl-methyl]amino]-1,1,1-trifluoro-2-propanol;
3-[[3-(3-isopropylphenoxy)phenyl][(3-trifluoromethoxy)cyclohexyl-methyl]amino]-1,1,1-trifluoro-2-propanol;
3-[[3-(3-isopropylphenoxy)phenyl][3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethyl)amino]-1,1,1-trifluoro-2-propanol;
3-[[3-(2,3-dichlorophenoxy)phenyl][(3-trifluoromethyl)cyclohexyl-methyl]amino]-1,1,1-trifluoro-2-propanol;
3-[[3-(2,3-dichlorophenoxy)phenyl][(3-pentafluoroethyl)cyclohexyl-methyl]amino]-1,1,1-trifluoro-2-propanol;
3-[[3-(2,3-dichlorophenoxy)phenyl][(3-trifluoromethoxy)cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexyl-methyl]amino]-1,1,1-trifluoro-2-propanol;
3-[[3-(4-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phennyl](cyclopropylmethyl)amino]-1,1,1-triflouro-2-propanol;
3-[[3-(4-fluorophenoxy)phenyl][(3-trifluoromethyl)cyclohexyl-methyl]amino]-1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][[3-(1,1,2,2-tetrafluoroethoxy)cyclohexyl-methyl]amino]-1,1,1-trifluoro-2-propanol;
3-[[3-(3-trifluoromethoxybenzyloxy]phenyl](cyclohexylmethyl)amino]-1,1,1-trifluoro-2-propanol;
3-[[3-(3-trifluoromethoxybenzyloxy)phenyl](cyclopentylmethyl)amino]-1,1,1-trifluoro-2-propanol;
3-[[3-(3-trifluoromethoxybenzyloxy)phenyl](cyclopropylmethyl]amino]-1,1,1-trifluoro-2-propanol;
3-[[3-(3-trifluoromethoxybenzyloxy)phenyl][(3-trifluoromethyl)cyclohexyl-methyl]amino]-1,1,1-trifluoro-2-propanol;
3-[[3-(3-trifluoromethoxybenzyloxy)phenyl][(3-pentafluoroethyl)cyclohexyl-methyl]amino]-1,1,1-trifluoro-2-propanol;
3-[[3-(3-trifluoromethoxybenzyloxy)phenyl][(3-trifluoromethoxy)cyclohexyl-methyl]amino]-1,1,1-trifluoro-2-propanol;
3-[[3-(3-trifluoromethoxybenzyloxy)phenyl][[3-(1,1,2,2-tetrafluoroethoxy)-cyclohexylmethyl]amino]-1,1,1-trifluoro-2-propanol;
3-[[3-(3-trifluoromethylbenzyloxy)phenyl](cyclohexylmethyl)amino]-1,1,1-trifluoro-2-propanol;
3-[[3-(3-trifluoromethylbenzyloxy)phenyl](cyclopentylmethyl)amino]-1,1,1-trifluoro-2-propanol;
3-[[3-(3-trifluoromethylbenzyloxy)phenyl](cyclopropyl methyl)amino]-1,1,1-trifluoro-2-propanol;
3-[[3-(3-trifluoromethylbenzyioxy)phenyl][(3-trifluoromethyl)cyclohexyl-methyl]amino]-1,1,1-trifluoro-2-propanol;
3-[[3-(3-trifluoromethylbenzyloxy)phenyl][(3-pentafluoroethyl)cyclohexyl-methyl]amino]-1,1,1-trifluoro-2-propanol;
3-[[3-(3-trifluoromethyl benzyloxy)phenyl][(3-trifluoromethoxy)cyclohexyl-methyl]amino]-1,1,1-trifluoro-2-propanol;
3-[[3-(3-trifluoromethylbenzyloxy)phenyl][3-(1,1,2,2-tetrafluoroethoxy)cyclohexyl-methyl]amino]-1,1,1-trifluoro-2-propanol;
3-[[[(3-trifluoromethyl)phenyl]methyl](cyclohexyl)amino]-1,1,1-trifluoro-2-propanol;
3-[[[(3-pentafluoroethyl)phenyl]methyl](cyclohexyl)amino]-1,1,1-trifluoro-2-propanol;
3-[[[(3-trifluoromethoxy)phenyl]methyl](cyclohexyl)amino]-1,1,1-trifluoro-2-propanol;
3-[[[3-(1,1,2,2-tetrafluoroethoxy)phenyl]methyl](cyclohexyl)amino]-1,1,1-trifluoro-2-propanol;
3-[[[(3-trifluoromethyl)phenyl]methyl](4-methylcyclohexyl)amino]-1,1,1-trifluoro-2-propanol;
3-[[[(3-pentafluoroethyl)phenyl]methyl](4-methylcyclohexyl)amino]-1,1,1-trifluoro-2-propanol;
3-[[[(3-trifluoromethoxy)phenyl]methyl](4-methylcyclohexyl)amino]-1,1,1-trifluoro-2-propanol;
3-[[[3-(1,1,2,2-tetrafluoroethoxy)phenyl]methyl](4-methyl-cyclohexyl)amino]-1,1,1-trifluoro-2-propanol;
3-[[[(3-trifluoromethyl]phenyl]methyl](3-trifluoromethyl-cyclohexyl)amino]-1,1,1-trifluoro-2-propanol;
3-[[[(3-pentafluoroethyl)phenyl]methyl](3-trifluoromethyl-cyclohexyl)amino]-1,1,1-trifluoro-2-propanol;
3-[[[(3-trifluoromethoxy)phenyl]methyl](3-trifluoromethyl-cyclohexyl)amino]-1,1,1-trifluoro-2-propanol;
3-[[[3-(1,1,2,2-tetrafluoroethoxy)phenyl]methyl](3-trifluoromethylcyclohexyl)amino]-1,1,1-trifluoro-2-propanol;
3-[[[(3-trifluoromethyl)phenyl]methyl][3-(4-chloro-3-ethylphenoxy)cyclo-hexyl]amino]-1,1,1-trifluoro-2-propanol;
3-[[[(3-pentafluoroethyl)phenyl]methyl][3-(4-chloro-3-ethylphenoxy)cyclo-hexyl]amino]-1,1,1-trifluoro-2-propanol;
3-[[[(3-trifluoromethoxy)phenyl]methyl][3-(4-chloro-3-methylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethyl phenoxy)-cyclohexyl]amino]-1,1,1-trifluoro-2-propanol;
3-[[[(3-trifluoromethyl)phenyl]methyl](3-phenoxycyclohexyl)amino]-1,1,1-trifluoro-2-propanol;
3-[[[(3-pentafluoroethyl)phenyl]methyl](3-phenoxycyclohexyl)amino]-1,1,1-trifluoro-2-propanol;
3-[[[(3-trifluoromethoxy)phenyl]methyl](3-phenoxycyclohexyl)amino]-1,1,1-trifluoro-2-propanol;
3-[[[3-(1,1,2,2-tetrafluoroethoxy)phenyl]methyl](3-phenoxycyclohexyl)amino]-1,1,1-trifluoro-2-propanol;
3-[[[(3-trifloromethyl)phenyl]methyl](3-isopropoxycyclohexyl)amino]-1,1,1-trifluoro-2-propanol;
3-[[[(3-pentafluoroethyl)phenyl]methyl](3-isopropoxycyclohexyl)amino]-1,1,1-trifluoro-2-propanol;
3-[[[(3-trifluoromethoxy)phenyl]methyl](3-isopropoxycyclohexyl)amino]-1,1,1-trifluoro-2-propanol;
3-[[[3-(1,1,2,2-tetrafluoroethoxy)phenyl]methyl](3-isopropoxycyclohexyl)-amino]-1,1,1-trifluoro-2-propanol;
3-[[[(3-trifluoromethyl)phenyl]methyl](3-cyclopentyloxycyclohexyl]amino]-1,1,1-trifluoro-2-propanol;
3-[[[(3-pentafluoroethyl)phenyl]methyl](3-cyclopentyloxycyclohexyl)amino]-1,1,1-trifluoro-2-propanol;
3-[[[(3-trifluoromethoxy)phenyl]methyl](3-cyclopentyloxycyclohexyl)amino]-1,1,1-trifluoro-2-propanol;
3-[[[3-(1,1,2,2-tetrafluoroethoxy)phenyl]methyl](3-cyclopentyloxycyclohexyl)-amino]-1,1,1-trifluoro-2-propanol;
3-[[[(2-trifluoromethyl)pyrid-6-yl]methyl](3-isopropoxycyclohexyl)amino]-1,1,1-trifluoro-2-propanol;
3-[[[(2-trifluoromethyl)pyrid-6-yl]methyl](3-cyclopentyloxycyclohexyl)-amino]-1,1,1-trifluoro-2-propanol;
3-[[[(2-trifluoromethyl)pyrid-6-yl]methyl](3-phenoxycyclohexyl)amino]-1,1,1-trifluoro-2-propanol;
3-[[[(2-trifluoromethyl)pyrid-6-yl]methyl](3-trifluoromethylcyclohexyl)amino]-1,1,1-trifluoro-2-propanol;
3-[[[(2-trifluoromethyl)pyrid-6-yl]methyl][3-(4-chloro-3-ethylphenoxy)cyclo-hexyl]amino]-1,1,1-trifluoro-2-propanol;
3-[[[(2-trifluoromethyl)pyrid-6-yl]methyl][3-(1,1,2,2-tetrafluoroethoxy)cyclo-hexyl]amino]-1,1,1-trifluoro-2-propanol;
3-[[[(2-trifluoromethyl)pyrid-6-yl]methyl](3-pentafluoroethylcyclohexyl)-amino]-1,1,1-trifluoro-2-propanol;
3-[[[(2-trifluoromethyl)pyrid-6-yl]methyl](3-trifluoromethoxycyclohexyl)-amino]-1,1,1-trifluoro-2-propanol;
3-[[[(3-trifluoromethyl)phenyl]methyl][3-(4-chloro-3-ethylphenoxy)propyl]-amino]-1,1,1-trifluoro-2-propanol;
3-[[[(3-pentafluoroethyl)phenyl]methyl][3-(4-chloro-3-ethylphenoxy)propyl]-amino]-1,1,1-trifluoro-2-propanol;
3-[[[(3-trifluoromethoxy)phenyl]methyl][3-(4-chloro-3-ethylphenoxy)propyl]-amino]-1,1,1-trifluoro-2-propanol;
3-[[[3-(1,1,2,2-tetrafluoroethoxy)phenyl]methyl][3-(4-chloro-3-ethylphenoxy)-propyl]amino]-1,1,1-trifluoro-2-propanol;
3-[[[(3-trifluoromethyl)phenyl]methyl][3-(4-chloro-3-ethylphenoxy)-2,2,-difluropropyl]amino]-1,1,1-trifluoro-2-propanol;
3-[[[(3-pentafluoroethyl)phenyl]methyl][3-(4-chloro-3-ethylphenoxy)-2,2-difluropropyl]amino]-1,1,1-trifluoro-2-propanol;
3-[[[(3-trifluoromethoxy)phenyl]methyl][3-(4-chloro-3-ethylphenoxy)-2,2,-difluropropyl]amino]-1,1,1-trifluoro-2-propanol;
3-[[[3-(1,1,2,2-tetrafluoroethoxy)phenyl]methyl][3-(4-chloro-3-ethylphenoxy)-2,2,-difluoropropyl]amino]-1,1,1-trifluoro-2-propanol;
3-[[[(3-trifluoromethyl)phenyl]methyl][3-(isopropoxy)propyl]amino]-1,1,1-trifluoro-2-propanol;
3-[[[(3-pentafluoroethyl)phenyl]methyl][3-(isopropoxy)propyl]amino]-1,1,1-trifluoro-2-propanol;
3-[[[(3-trifluoromethoxy)phenyl]methyl][3-(isopropoxy)propyl]amino]-1,1,1-trifluoro-2-propanol;
3-[[[3-(1,1,2,2-tetrafluoroethoxy)phenyl]methyl]]3-(isopropoxy)propyl]amino]-1,1,1-trifluoro-2-propanol; and
3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI

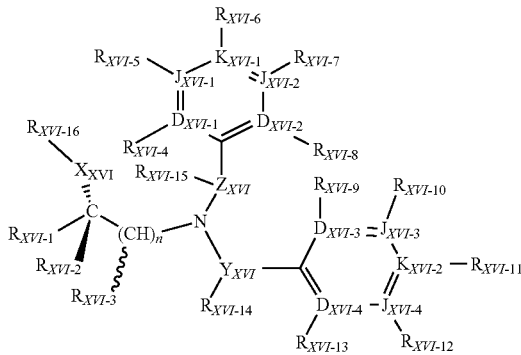

Formula XVI and pharmaceutically acceptable forms thereof, wherein:
$n_{XVI}$ is an integer selected from 1 through 4;
$X_{XVI}$ is oxy;
$R_{XVI-1}$ is selected from the group consisting of haloalkyl, haloalkenyl, haloalkoxymethyl, and haloalkenyloxymethyl with the proviso that $R_{XVI-1}$ has a higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(III);

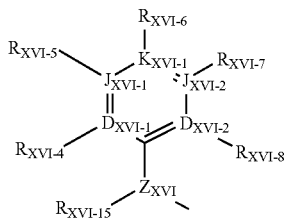

XVI-II

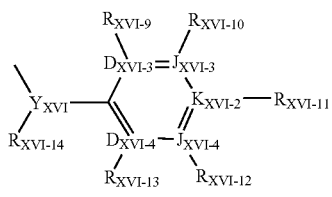

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$ and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{KVI-1}$ must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI}2$, $J_{XVI-1}$, $J_{XVI-2}$ and $K_{XVI-11}$ is N;

$D_{XVI-3}$, $D_{XV-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is O and S, one of $D_{XVI-3}$, $D_{XVI-4}$, $J_{XVI-3}$, $J_{XVI-4}$ and $K_{XVI-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenytoxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-lngold-Prelog stereochemical system ranking than $R_{XVI-1}$ and a higher Cahn-lngold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI-4}$—$CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-15}))_k$ wherein j and k are integers independently selected from 0 and 1;

$W_{XVI}$ is selected from the group consisting of O, C(O), C(S), C(O)N($R_{XVI-14}$), C(S)N($R_{XVI-14}$), ($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydoxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XDVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XIV-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is used at the same time.

Compounds of Formula XVI and their methods of manufacture are disclosed in PCT Publication No. WO 00/18724, which is incorporated herein by reference in its entirety for all purposes.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol:

(2R)-3-[[3-(3-methylphenoxy)phenyl][[3-(1,1,2,2-tetrafluoroethoxy)phenyl]-methyl]amino]-1,1,1-trifluoro-2-propanol;

(2R)-3-[[3-(5,6,7,8-tetrahydro-2-naphthoxy)phenyl][[3-(1,1,2,2-tetrafluoro-ethoxy)phenyl]methyl]amino]-1,1,1-trifluoro-2-propanol;

(2R)-3-[[3-(phenoxy)phenyl][[3-(1,1,2,2-tetrafluoroethoxy)phenyl]methyl]amino]-1,1,1-trifluoro-2-propanol;

(2R)-3-[[3-[3-(N,N-dimethylamino)phenoxy]phenyl][[3-(1,1,2,2-tetrafluoro-ethoxy)phenyl]methyl]amino]-1,1,1-trifluoro-2-propanol;

(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;

(2R)-3-[[[3-(1,1,2,2-tetrafluoroethoxy)phenyl]methyl][3-[[3-(trifluoro-methyl)phenyl]methoxy]phenyl]amino]-1,1,1-trifluoro-2-propanol;

(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;

(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;

(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;

(2R)-3-[[[3-(1,1,2,2-tetrafluoroethoxy)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[3-(1,1,2,2-tetrafluoroethoxy)-phenyl]methyl]amino]-1,1,1-trfluoro-2-propanol;

(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

(2R)-3-[[3-(3-difluoromethoxyphenoxy)phenyl][[3-(1,1,2,2-tetrafluoroethoxy)-phenyl]methyl]amino]-1,1,1-trifluoro-2-propanol;

(2R)-3-[[[3-(3-trifuoromethylthio)phenoxy]phenyl][[3-(1,1,2,2-tetrafluoroethoxy)-phenyl]methyl]amino]-1,1,1-trifluoro-2-propanol;

(2R)-3-[(3-(4-chloro-3-trifluoromethylphenoxy)phenyl][(3-(1,1,2,2-tetrafluoroethoxy)-phenyl]methyl]amino]-1,1,1-trifluoro-2-propanol;

(2R)-3-[[3-(3-trifluoromethoxyphenoxy)phenyl][[3-(pentafluoroethyl)phenyl]-methyl]amino]-1,1,1-trifluoro-2-propanol;

(2R)-3-[[3-(3-isopropylphenoxy)phenyl][[3-(pentafluoroethyl)phenyl]methyl]-amino]-1,1,1-trifluoro-2-propanol;

(2R)-3-[[3-(3-cyclopropylphenoxy)phenyl][[3-(pentafluoroethyl)phenyl]methyl]-amino]-1,1,1-trifluoro-2-propanol;

(2R)-3-[[3-(3-(2-furyl)phenoxy)phenyl][[3-(pentafluoroethyl)phenyl]methyl]-amino]-1,1,1-trifluoro-2-propanol;

(2R)-3-[[3-(2,3-dichlorophenoxy)phenyl][[3-(pentafluoroethyl)phenyl]methyl]-amino]-1,1,1-trifluoro-2-propanol;

(2R)-3-[[3-(4-fluorophenoxy)phenyl][[3-(pentafluoroethyl)phenyl]methyl]amino]-1,1,1-trifluoro-2-propanol;

(2R)-3-[[3-(4-methylphenoxy)phenyl][[3-(pentafluoroethyl)phenyl]methyl]amino]-1,1,1-trifluoro-2-propanol;

(2R)-3-[[3-(2-fluoro-5-bromophenoxy)phenyl][[3-(pentafluoroethyl)phenyl]methyl]-amino]-1,1,1-trifluoro-2-propanol;

(2R)-3-[[3-(4-chloro-3-ethylphenoxy)phenyl][[3-(pentafluoroethyl)phenyl]methyl]-amino]-1,1,1-trifluoro-2-propanol;

(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;

(2R)-3-[[3-[3-(pentafluoroethyl)phenoxy]phenyl][[3-(pentafluoroethyl)phenyl]-methyl]amino]-1,1,1,-trifluoro-2-propanol;

(2R)-3-[[3-(3,5-dimethylphenoxy)phenyl][[3-(pentafluoroethyl)phenyl]methyl]-amino]-1,1,1-trifluoro-2-propanol;

(2R)-3-[[3-(3-ethylphenoxy)phenyl][[3-(pentafluoroethyl)phenyl]methyl]amino]-1,1,1-trifluoro-2-propanol;

(2R)-3-[[3-(3-t-butylphenoxy)phenyl][[3-(pentafluoroethyl)phenyl]methyl]amino]-1,1,1-trifluoro-2-propanol;

- (2R)-3-[[3-(3-methylphenoxy)phenyl][[3-(pentafluoroethyl)phenyl]methyl]amino]-1,1,1-trifluoro-2-propanol;
- (2R-3-[[3-(5,6,7,8-tetrahydro-2-naphthoxy)phenyl][[3-(pentafluoroethyl)phenyl]-methyl]amino]-1,1,1-trifluoro-2-propanol;
- (2R)-3-[[3-(phenoxy)phenyl][[3(pentafluoroethyl)phenyl]methyl]amino]-1,1,1-trifluoro-2-propanol;
- (2R)-3-[[3-[3-(N,N-dimethylamino)phenoxy]phenyl][[3(pentafluoroethyl)phenyl]methyl]amino]-1,1,1-trifluoro-2-propanol;
- (2R)-3-[[[3-(pentafluoroethyl)phenyl]methyl][3-[[3-(trifluoromethoxy)phenyl]-methoxy]phenyl]amino]-1,1,1-trifluoro-2-propanol;
- (2R)-3-[[[3-(pentafluoroethyl)phenyl]methyl][3-[[3-(trifluoromethyl)-phenyl]-methoxy]phenyl]amino]-1,1,1-trifluoro-2-propanol;
- (2R)-3-[[[3-(pentafluoroethyl)phenyl]methyl][3-[[3,5-dimethylphenyl]methoxy]-phenyl]amino]-1,1,1-trifluoro-2-propanol;
- (2R-3-[[[3-(pentafluoroethyl)phenyl]methyl][3-[[3-(trifluoromethylthio)phenyl]-methoxy]phenyl]amino]-1,1,1-trifluoro-2-propanol;
- (2R)-3-[[[3-(pentafluoroethyl)phenyl]methyl][3-[[3,5-difluorophenyl]methoxy]-phenyl]amino]-1,1,1-trifluoro-2-propanol;
- (2R)-3-[[[3-(pentafluoroethyl)phenyl]methyl][3-[cyclohexylmethoxy]phenyl]-amino]-1,1,1-trifluoro-2-propanol;
- (2R)-3-[[3-(2-difluoromethoxy-4-pyridyloxy)phenyl][[3-(pentafluoroethyl)phenyl]-methyl]amino]-1,1,1-trifluoro-2-propanol;
- (2R)-3-[[3-(2-trifluoromethyl-4-pyridyloxy)phenyl][[3-(pentafluoroethyl)phenyl]-methyl]amino]-1,1,1-trifluoro-2-propanol;
- (2R)-3-[[3-(3-difluoromethoxyphenoxy)phenyl][[3-(pentafluoroethyl)phenyl]-methyl]amino]-1,1,1-trifluoro-2-propanol;
- (2R)-3-[[[3-(3-trifluoromethylthio)phenoxy]phenyl][[3-(pentafluoroethyl)phenyl]-methyl]amino]-1,1,1-trifluoro-2-propanol;
- (2R)-3-[[3-(4-chloro-3-trifluoromethylphenoxy)phenyl][[3-(pentafluoroethyl)-phenyl]-methyl]amino]-1,1,1-trifluoro-2-propanol;
- (2R)-3-[[3-(3-trifluoromethoxyphenoxy)phenyl][[3-(heptafluoropropyl)phenyl]-methyl]amino]-1,1,1-trifluoro-2-propanol;
- (2R)-3-[[3-(3-isopropylphenoxy)phenyl][[3-(heptafluoropropyl)phenyl]methyl]-amino]-1,1,1-trifluoro-2-propanol;
- (2R)-3-[[3-(3-cyclopropylphenoxy)phenyl][[3-(heptafluoropropyl)phenyl]methyl]-amino]-1,1,1-trifluoro-2-propanol;
- (2R)-3-[[3-(3-(2-furyl)phenoxy)phenyl][[3-(heptafluoropropyl)phenyl]methyl]-amino]-1,1,1-trifluoro-2-propanol;
- (2R)-3-[[3-(2,3-dichlorophenoxy)phenyl][[3-(heptafluoropropyl)phenyl]methyl]-amino]-1,1,1-trifluoro-2-propanol;
- (2R)-3-[[3-(4-fluorophenoxy)phenyl][[3-(heptafluoropropyl)phenyl]methyl]amino]-1,1,1-trifluoro-2-propanol;
- (2R)-3-[[3-(4-methylphenoxy)phenyl][[3-(heptafluoropropyl)phenyl]methyl]amino]-1,1,1-trifluoro-2-propanol;
- (2R)-3-[[3-(2-fluoro-5-bromophenoxy)phenyl][[3-(heptafluoropropyl)phenyl]-methyl]amino]-1,1,1-trifluoro-2-propanol;
- (2R)-3-[[3-(4-chloro-3-ethylphenoxy)phenyl][[3-(heptafluoropropyl)phenyl]methyl]-amino]-1,1,1-trifluoro-2-propanol;
- (2R)-3-[3-(1,1,2,2-tetrafluoroethoxy)phenoxy]phenyl][[3-(heptafluoropropyl)-phenyl]methyl]amino]-1,1,1-trifluoro-2-propanol;
- (2R)-3-[[3-(pentafluoroethyl)phenoxy]phenyl][[3-heptafluoropropyl)phenyl]-methyl]amino]-1,1,1-trifluoro-2-propanol;
- (2R)-3-[[3-(3,5-dimethylphenoxy)phenyl][[3-heptafluoropropyl)phenyl]methyl]-amino]-1,1,1-trifluoro-2-propanol;
- (2R)-3-[[3-(3-ethylphenoxy)phenyl][[3-(heptafluoropropyl)phenyl]methyl]amino]-1,1,1-trifluoro-2-propanol;
- (2R)-3-[[3-(3-t-butylphenoxy)phenyl][[3-(heptafluoropropyl)phenyl]methyl]amino]-1,1,1-trifluoro-2-propanol;
- (2R)-3-[[3-(3-methylphenoxy)phenyl][[3-(heptafluoropropyl)phenyl]methyl]amino]-1,1,1-trifluoro-2-propanol;
- (2R)-3-[[3-(5,6,7,8-tetrahydro-2-naphthoxy)phenyl][[3-(heptafluoropropyl)phenyl]-methyl]amino]-1,1,1-trifluoro-2-propanol;
- (2R)-3-[[3-(phenoxy)phenyl][[3-(heptafluoropropyl)phenyl]methyl]amino]-1,1,1-trifluoro-2-propanol;
- (2R)-3-[[3-[3-(N,N-dimethylamino)phenoxy]phenyl][[3-(heptafluoropropyl)phenyl]-methyl]amino]-1,1,1-trifluoro-2-propanol;
- (2R)-3-[[[3-(heptafluoropropyl)phenyl]methyl][3-[[3-(trifluoromethoxy)phenyl]-methoxy]phenyl]amino]-1,1,1-trifluoro-2-propanol;
- (2R)-3-[[[3-(heptafluoropropyl)phenyl]methyl][3-[[3-(trifluoromethyl)phenyl]-methoxy]phenyl]amino]-1,1,1-trifluoro-2-propanol;
- (2R)-3-[[[3-(heptafluoropropyl)phenyl]methyl][3-[[3,5-dimethylphenyl]methoxy]-phenyl]amino]-1,1,1-trifluoro-2-propanol;
- (2R)-3-[[[3-(heptafluoropropyl)phenyl]methyl][3-[[3-(trifluoromethylthio)phenyl]-methoxy]phenyl]amino]-1,1,1-trifluoro-2-propanol;
- (2R)-3-[[[3-(heptafluoropropyl)phenyl]methyl][3-[[3,5-difluorophenyl]methoxy]-phenyl]amino]-1,1,1-trifluoro-2-propanol;
- (2R)-3-[[[3-(heptafluoropropyl)phenyl]methyl][3-[cyclohexylmethoxy]phenyl]-amino]-1,1,1-trifluoro-2-propanol;
- (2R)-3-[[3-(2-difluoromethoxy-4-pyridyloxy)phenyl][[3-(heptafluoropropyl)phenyl]-methyl]amino]-1,1,1-trifluoro-2-propanol;
- (2R)-3-[[3-(2-trifluoromethyl-4-pyridyloxy)phenyl][[3-(heptafluoropropyl)phenyl]-methyl]amino]-1,1,1-trifluoro-2-propanol;
- (2R)-3-[[3-(3-difluoromethoxyphenoxy)phenyl][[3-(heptafluoropropyl)phenyl]-methyl]amino]-1,1,1-trifluoro-2-propanol;
- (2R)-3-[[[3-(3-trifluoromethylthio)phenoxy]phenyl][[3-theptafluoropropyl)phenyl]-methyl]amino]-1,1,1-trifluoro-2-propanol;
- (2R)-3-[(3-(4-chloro-3-trifluoromethylphenoxy)phenyl][[3-(heptafluoropropyl)-phenyl]methyl]amino]-1,1,1-trifluoro-2-propanol;
- (2R)-3-[[3-(3-trifluoromethoxyphenoxy)phenyl][[2-fluoro-5-(trifluoromethyl)-phenyl]methyl]amino]-1,1,1-trifluoro-2-propanol;
- (2R)-3-[[3-(3-isopropylphenoxy)phenyl][[2-fluoro-5-(trifluoromethyl)phenyl]-methyl]amino]-1,1,1-trifluoro-2-propanol;

(2R)-3-[[3-(3-cyclopropylphenoxy)phenyl][[2-fluoro-5-(trifluoromethyl)phenyl]-methyl]amino]-1,1,1-trifluoro-2-propanol;
(2R)-3-[[3-(2-furyl)phenoxy)phenyl][[2-fluoro-5-(trifluoromethyl)phenyl]-methyl]amino]-1,1,1-trifluoro-2-propanol;
(2R)-3-[[3-(2,3-dichlorophenoxy)phenyl][[2-fluoro-5-(trifluoromethyl)phenyl]-methyl]amino]-1,1,1-trifluoro-2-propanol;
(2R)-3-[[3-(4-fluorophenoxy)phenyl][[2-fluoro-5-(trifluoromethyl)phenyl]-methyl]amino]-1,1,1-trifluoro-3-propanol;
(2R)-3-[[3-(4-methylphenoxy)phenyl][[2-fluoro-5-(trifluoromethyl)phenyl]-methyl]amino]-1,1,1-trifluoro-2-propanol;
(2R)-3-[[3-(2-fluoro-5-bromophenoxy)phenyl][[2-fluoro-5-(trifluoromethyl)-phenyl]methyl]amino]-1,1,1-trifluoro-2-propanol;
(2R)-3-[[3-(4-chloro-3-ethylphenoxy)phenyl][[2-fluoro-5-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
(2R)-3-[[3-(3-(pentafluoroethyl)phenoxy]phenyl][[2-fluoro-5-(trifluoromethyl)-phenyl]methyl]amino]-1,1,1-trifluoro-2-propanol;
(2R)-3-[[3-(3,5-dimethylphenoxy)phenyl][[2-fluoro-5-(trifluoromethyl)phenyl]-methyl]amino]-1,1,1-trifluoro-2-propanol;
(2R)-3-[[3-(3-ethylphenoxy)phenyl][[2-fluoro-5-(trifluoromethyl)phenyl]methyl]-amino]-1,1,1-trifluoro-2-propanol;
(2R)-3-[[3-(3-t-butylphenoxy)phenyl][[2-fluoro-5-(trifluoromethyl)phenyl]methyl]-amino]-1,1,1-trifluoro-2-propanol;
(2R)-3-[[3-(3-methylphenoxy)phenyl][[2-fluoro-5-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;
(2R)-3-[[3-(phenoxy)phenyl][[2-fluoro-5-(trifluoromethyl)phenyl]methyl]amino]-1,1,1-trifluoro-2-propanol;
(2R)-3-[[3-[3-(N,N-dimethylamino,phenoxy]phenyl][[2-fluoro-5-(trifluoromethyl)-phenyl]methyl]amino]-1,1,1-trifluoro-2-propanol;
(2R)-3-[[[2-fluoro-5-(trifluoromethyl)phenyl]methyl](3-[[3-(trifluoromethoxy)-phenyl]methoxy]phenyl]amino]-1,1,1-trifluoro-3-propanol;
(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;
(2R-3-[[[2-fluoro-5-trifluoromethyl)phenyl]methyl][3-[[3,5-dimethylphenyl]-methoxy]phenyl]amino]-1,1,1-trifluoro-2-propanol;
(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-5-(trifluoromethyl)phenyl]methyl][3-[[3,5-difluorophenyl]-methoxy]phenyl]amino]-1,1,1-trifluoro-2-propanol;
(2R)-3-[[[2-fluoro-5-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;
(2R)-3-[[3-(3-difluoromethoxyphenoxy)phenyl][[2-fluoro-5-(trifluoromethyl)-phenyl]methyl]amino]-1,1,1-trifluoro-2-propanol;
(2R)-3-[[[3-(3-trifluoromethylthio)phenoxy]phenyl][[2-fluoro-5-(trifluoromethyl)-phenyl]methyl]amino]-1,1,1-trifluoro-2-propanol;
(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;
(2R)-3-[(3-(3-trifluoromethoxyphenoxy)phenyl][[2-fluoro-4-(trifluoromethyl)-phenyl]methyl]amino]-1,1,1-trifluoro-2-propanol;
(2R)-3-[[3-(3-isopropylphenoxy)phenyl][[2-fluoro-4-(trifluoromethyl)phenyl]-methyl]amino]-1,1,1-trifluoro-2-propanol;
(2R)-3-[[3-(3-cyclopropylphenoxy)phenyl][[2-flouro-4-(trifluoromethyl)phenyl]-methyl]amino]-1,1,1-trifluoro-2-propanol;
(2R)-3-[[3-(3-(2-furyl)phenoxy)phenyl][[2-fluoro-4-(trifluoromethyl)phenyl]-methyl]amino]-1,1,1-trifluoro-2-propanol;
(2R)-3-[[3-(2,3-dichlorophenoxy)phenyl][[2-fluoro-4-(trifluoromethyl)phenyl]-methyl]amino]-1,1,1-trifluoro-2-propanol;
(2R)-3-[[3-(4-fluorophenoxy)phenyl][[2-fluoro-4-(trifluoromethyl)phenyl]-methyl]amino]-1,1,1-trifluoro-2-propanol;
(2R)-3-[[3-(4-methylphenoxy)phenyl][[2-fluoro-4-(trifluoromethyl)phenyl]-methyl]amino]-1,1,1,-trifluoro-2-propanol;
(2R)-3-[[3-(2-fluoro-5-bromophenoxy)phenyl][[2-fluoro-4-(trifluoromethyl)-phenyl]methyl]amino]-1,1,1-trifluoro-2-propanol;
(2R)-3-[[3-(4-chloro-3-ethylphenoxy)phenyl][[2-fluoro-4-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;
(2R-3-[[3-[3-(pentafluoroethyl)phenoxy]phenyl][[2-fluoro-4-(trifluoromethyl)phenyl]methyl]amino]-1,1,1-trifluoro-2-propanol;
(2R)-3-[[3-(3,5-dimethylphenoxy)phenyl][[2-fluoro-4-(trifluoromethyl)phenyl]-methyl]amino]-1,1,1-trifluoro-2-propanol;
(2R)-3-[[3-(3-ethylphenoxy)phenyl][[2-fluoro-4-(trifluoromethyl)phenyl]methyl]-amino]-1,1,1-trifluoro-2-propanol;
(2R)-3-[[3-(3-t-butylphenoxy)phenyl][[2-fluoro-4-(trifluoromethyl)phenyl]methyl]-amino]-1,1,1-trifluoro-2-propanol;
(2R)-3-[[3-(3-methylphenoxy)phenyl][[2-fluoro-4-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;
(2R)-3-[[3-(phenoxy)phenyl][[2-fluoro-4-(trifluoromethyl)phenyl]methyl]amino]-1,1,1-trifluoro-2-propanol;

(2R)-3-[[3-[3-(N,N-dimethylamino)phenoxy]phenyl][[2-fluoro-4-(trifluoromethyl)-phenyl]methyl]amino]-1,1,1-trifluoro-2-propanol;

(2R)-3-[[[2-fluoro-4-(trifluoromethyl)phenyl]methyl][3-[[3-(trifluoromethoxy)phenyl]methoxy]phenyl]amino]-1,1,1-trifluoro-2-propanol;

(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;

(2R)-3-[[[2-fluoro-4-(trifluoromethyl)phenyl]methyl][3-[[3,5-dimethylphenyl]-methoxy]phenyl]amino]-1,1,1-trifluoro-2-propanol;

(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;

(2R)-3-[[[2-fluoro-4-(trifluoromethyl)phenyl]methyl][3-[[3,5-difluorophenyl]-methoxy]phenyl]amino]-1,1,1-trifluoro-2-propanol;

(2R)-3-[[[2-fluoro-4-(trifluoromethyl)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;

(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;

(2R)-3-[[[3-(3-difluoromethoxyphenoxy)phenyl][[2-fluoro-4-(trifluoromethyl)-phenyl]methyl]amino]-1,1,1-trifluoro-2-propanol;

(2R)-3-[[[3-(3-trifluoromethylthio)phenoxy]phenyl][[2-fluoro-4-(trifluoromethyl)-phenyl]methyl]amino]-1,1,1-trifluoro-2-propanol; and (2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

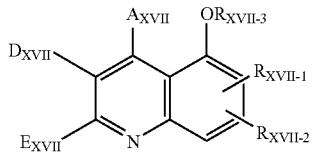

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{XVII-4}R_{XVII-5}$, wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula $R_{XVII-6}$-$L_{XVII}$,

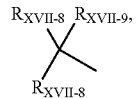

or $R_{XVII-10}$-$T_{XVII}$-$V_{XVII}$-$X_{XVII}$ wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteoatoms from the series of S, N and/or O, and/or in the form of a group according to the formula —$OR_{XVII-11}$, —$SR_{XVII-12}$, —$SO_2R_{XVII-13}$, or —$NR_{XVII-14}R_{XVII-15}$;

$R_{XVII-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

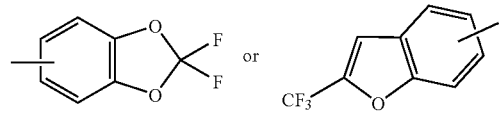

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$;

$R_{XVII-16}$ and $R_{XVII-17}$ are identical or different and have the meaning of $R_{XVII-4}$ and $R_{XVII-5}$ above; or $R_{XVII-8}$ and $R_{XVII-9}$ together form a radical according to the formula =O or =$NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or —$NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched akyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substitued phenyl, and/or an alkyl that is optionally substituted with a group according to the formula $-OR_{XVII-24}$;

$R_{XVII-24}$ is a straight-chained or branched acyl with up to 4 carbon atoms or benzyl.

Compounds of Formula XVII and their methods of manufacture are disclosed in PCT Publication No. WO 98/39299, which is incorporated herein by reference in its entirety for all purposes.

Another class of CETP inhibitors that finds utility with the present invention consists of 4-Phenyltetrahydroquinolines of Formula XVIII

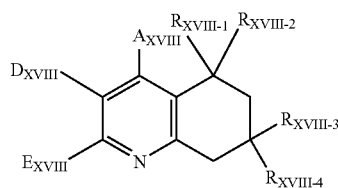

Formula XVIII

N oxides thereof, and pharmaceutically acceptable forms thereof, wherein:

$A_{XVIII}$ denotes a phenyl optionally substituted with up to two identical or different substituents in the form of halogen, trifluoromethyl or a straight-chain or branched alkyl or alkoxy containing up to three carbon atoms;

$D_{XVIII}$ denotes the formula

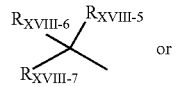 or $R_{XVIII-5}$ and $R_{XVIII-6}$ are taken together to form =O; or $R_{XVIII-5}$ denotes hydrogen and $R_{XVIII-6}$ denotes halogen or hydrogen; or $R_{XVIII-5}$ and $R_{XVIII-6}$ denote hydrogen;

$R_{XVIII-7}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, $-SO_2-CH_3$ or $NR_{XVIII-9}R_{XVIII-10}$;

$R_{XVIII-9}$ and $R_{XVIII-10}$ are identical or different and denote hydrogen or a straight-chained or branched alkyl of up to three carbon atoms;

$E_{XVIII}$ denotes a cycloalkyl of from three to six carbon atoms or a straight-chained or branched alkyl of up to eight carbon atoms;

$R_{XVIII-1}$ denotes hydroxy;

$R_{XVIII-2}$ denotes hydrogen or methyl;

$R_{XVIII-3}$ and $R_{XVIII-4}$ are identical or different and denote straight-chained or branched alkyl of up to three carbon atoms; or $R_{XVIII-3}$ and $R_{XVIII-4}$ taken together form an alkenylene made up of between two and four carbon atoms.

Compounds of Formula XVIII and their methods of manufacture are disclosed in PCT Publication No. WO 99/15504 and U.S. Pat. No. 6,291,477, both of which are incorporated herein by reference in their entireties for all purposes.

The present invention is particularly useful for acid-sensitive drugs which chemically react with acidic species, or are otherwise unstable in the presence of acidic species, including acidic dispersion polymers. Acid-sensitive drugs often have as part of their molecular structure functional groups which are reactive under acidic conditions, such as sulfonyl ureas, hydroxamic acids, hydroxy amides, carbamates, acetals, hydroxy ureas, esters, and amides. Drugs which include such functional groups may be prone to reactions such as hydrolysis, lactonization, or transesterification in the presence of acidic species.

Acid-sensitive drugs may be identified experimentally by determining whether the drug chemically reacts or degrades when dispersed in an acidic polymer. In particular, as used herein, the term "acid-sensitive drug" refers to a drug which, when dispersed in a "control acidic dispersion," degrades when stored under controlled aging conditions either for long storage times at ambient storage conditions or for short storage times under elevated temperature and relative humidity conditions. The "control acidic dispersion" used to determine whether a drug is acid-sensitive is a dispersion of the drug and an unneutralized acidic polymer as described below.

Alternatively, another test to determine whether a drug is an acid-sensitive drug as used herein is to administer the drug to an acidic aqueous solution and plot drug purity or potency versus time. The acidic solution should have a pH of from 1-4. Drugs which are acid sensitive are those for which the drug degrades (as evidenced by a decrease in drug purity or potency) by at least 1% within 24 hours of administration of the drug to the acidic solution. If the drug degrades by 1% in the 6-24 hour time period, then the drug is "slightly acid-sensitive." If the drug degrades by 1% in the 1-6 hour time period, then the drug is "moderately acid-sensitive." If the drug degrades by 1% in less than 1 hour, then the drug is "highly acid-sensitive." The present invention finds particular utility for drugs which are slightly acid-sensitive, moderately acid-sensitive and highly acid-sensitive.

Examples of acid-sensitive drugs include (+)-N-{3-[3-(4-fluorophenoxy)phenyl]-2-cyclopenten-1-yl}-N-hydroxyurea; omeprazole; etoposide; famotidine; erythromycin; quinapril; lansoprazole; progabide; as well as CCR1 inhibitors such as quinoxaline-2-carboxylic acid[4(R)-carbamoyl-1(S)-3-fluorobenzyl-2(S),7-dihydroxy-7-methyl-octyl] amide and quinoxaline-2-carboxylic acid[1-benzyl-4-(4,4-difluoro-1-hydroxy-cyclohexyl)-2-hydroxy-4-hydroxycarbamoyl-butyl]-amide.

The invention is useful for improving the intrinsic dissolution rate of compounds selected from the following. The intrinsic dissolution rate is defined as the rate of dissolution of a pure pharmaceutical active ingredient when conditions such as surface area, agitation-stirring speed, pH and ionic-strength of the dissolution medium are kept constant. Intrinsic dissolution rate is further defined as being measured in water at 37° C. using a USP II dissolution apparatus equipped with a Wood's apparatus (Wood, J H; Syarto, J E and Letterman, H: J. Pharm. Sci. 54 (1965), 1068) with a stirring speed of 50 rpm. The intrinsic dissolution rate is defined in terms of mg of drug dissolved per minute from a unit surface area, therefore, the intrinsic dissolution rate is referred to in units of mg/min.cm$^2$.

The compositions and methods of the invention are particularly useful for compounds with an intrinsic dissolution rate of preferably less than 0.1 mg/min.cm$^2$ and more preferably with less than 0.05 mg/min.cm$^2$.

Turning now to the chemical structures of specific CCR1 inhibitors, one class of CCR1 inhibitors that finds utility with the present invention consists of dihydroxyhexanoic acid derivatives having the Formula CCR1-I

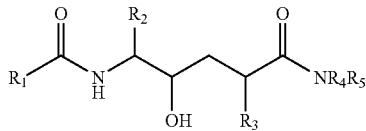

CCR1-I wherein $R_1$ is ($C_2$-$C_9$) heteroaryl optionally substituted with one, two or three substituents independently selected from the group consisting of hydrogen, halo, cyano, ($C_1$-$C_6$) alkyl optionally substituted with one, two or three fluorine atoms, hydroxy, hydroxy-($C_1$-$C_6$)alkyl, ($C_1$-$C_6$)alkoxy, ($C_1$-$C_6$)alkoxy($C_1$-$C_6$)alkyl, HO—(C═O)—, ($C_1$-$C_6$)alkyl-O—(C═O)—, HO—(C═O)—($C_1$-$C_6$)alkyl, ($C_1$-$C_6$)alkyl-O—(C═O)—($C_1$-$C_6$)alkyl, ($C_1$-$C_6$)alkyl-(C═O)—O—, ($C_1$-$C_6$)alkyl-(C═O)—O—($C_1$-$C_6$)alkyl, H(O═C)—, H(O═C)—($C_1$-$C_6$)alkyl, ($C_1$-$C_6$)alkyl(O═C)—, ($C_1$-$C_6$)alkyl(O═C)—($C_1$-$C_6$)alkyl, NO$_2$, amino, ($C_1$-$C_6$)alkylamino, [($C_1$-$C_6$)alkyl]$_2$amino, amino($C_1$-$C_6$)alkyl, ($C_1$-$C_6$)alkylamino($C_1$-$C_6$)alkyl, [($C_1$-$C_6$)alkyl]$_2$amino, ($C_1$-$C_6$)alkyl-H$_2$N—(C═O)—, ($C_1$-$C_6$)alkyl-NH—(C═O)—, [($C_1$-$C_6$)alkyl]$_2$N—(C═O)—, H$_2$N(C═O)—($C_1$-$C_6$)alkyl-HN(C═O)—($C_1$-$C_6$)alkyl, [($C_1$-$C_6$)alkyl]$_2$N—(C═O)—($C_1$-$C_6$)alkyl, H(O═C)—NH—, ($C_1$-$C_6$)alkyl(C═O)—NH, ($C_1$-$C_6$)alkyl(C═O)—[NH]($C_1$-$C_6$)alkyl, ($C_1$-$C_6$)alkyl(C═O)—[N($C_1$-$C_6$)alkyl]($C_1$-$C_6$)alkyl, ($C_1$-$C_6$)alkyl-S—, ($C_1$-$C_6$)alkyl-(S═O)—, ($C_1$-$C_6$)alkyl-SO$_2$—, ($C_1$-$C_6$)alkyl-SO$_2$—NH—, H$_2$N—SO$_2$—, H$_2$N—SO$_2$—($C_1$-$C_6$)alkyl, ($C_1$-$C_6$)alkylHN—SO$_2$—($C_1$-$C_6$)alkyl, [($C_1$-$C_6$)alkyl]$_2$N—SO$_2$—($C_1$-$C_6$)alkyl, CF$_3$SO$_3$—, ($C_1$-$C_6$)alkyl-SO$_3$—, phenyl, ($C_3$-$C_{10}$)cycloalkyl, ($C_2$-$C_9$)heterocycloalkyl, and ($C_2$-$C_9$)heteroaryl;

wherein $R_2$ is phenyl-(CH$_2$)$_m$—, naphthyl-(CH$_2$)$_m$—, ($C_3$-$C_{10}$)cycloalkyl-(CH$_2$)$_m$—, ($C_1$-$C_6$)alkyl or $C_2$-$C_9$)heteroaryl-(CH$_2$)$_m$—, wherein each of said phenyl, naphthyl, ($C_3$-$C_{10}$)cycloalkyl or ($C_2$-$C_9$)heteroaryl moieties of said phenyl-(CH$_2$)$_m$—, naphthyl-(CH$_2$)$_m$—, ($C_3$-$C_{10}$)cycloalkyl-(CH$_2$)$_m$— or ($C_2$-$C_9$)heteroaryl-(CH$_2$)$_m$— groups may optionally be substituted with one, two, or three substituents independently selected from the group consisting of hydrogen, halo, cyano, ($C_1$-$C_6$)alkyl, hydroxy, hydroxy-$C_1$-$C_6$) alkyl, ($C_1$-$C_6$)alkoxy, ($C_1$-$C_6$)alkoxy($C_1$-$C_6$)alkyl, HO—(C═O)—, ($C_1$-$C_6$)alkyl-O—(C═O)—, HO—(C═O)—($C_1$-$C_6$)alkyl-O—(C═O)—($C_1$-$C_6$)alkyl, ($C_1$-$C_6$)alkyl-(C═O)—O—, ($C_1$-$C_6$)alkyl-(C═O)—O—($C_1$-$C_6$)alkyl, H(O═C)—, H(O═C)—($C_1$-$C_6$)alkyl, ($C_1$-$C_6$)alkyl(O═C)—, ($C_1$-$C_6$)alkyl(O═C)—($C_1$-$C_6$)alkyl, NO$_2$, amino, ($C_1$-$C_6$)alkylamino, [($C_1$-$C_6$)alkyl]$_2$amino, amino ($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, H$_2$N—(C═O)—, ($C_1$-$C_6$)alkyl—NH—(C═O)—, [($C_1$-$C_6$)alkyl]$_2$N—(C═O)—, H$_2$N(C═O)—($C_1$-$C_6$)alkyl-HN(C═O)—($C_1$-$C_6$)alkyl, [($C_1$-$C_6$)alkyl]$_2$N—(C═O)—($C_1$-$C_6$)alkyl, H(O═C)—NH—, ($C_1$-$C_6$)alkyl(C═O)—NH, ($C_1$-$C_6$)alkyl(C═O)—[NH]($C_1$-$C_6$)alkyl, ($C_1$-$C_6$)alkyl(C═O)—[N($C_1$-$C_6$)alkyl] ($C_1$-$C_6$)alkyl, ($C_1$-$C_6$)alkyl-S—, ($C_1$-$C_6$)alkyl-(S═O)—, ($C_1$-$C_6$)alkyl-SO$_2$—, ($C_1$-$C_6$)alkyl-SO$_2$—NH—, H$_2$N—SO$_2$—, H$_2$N—SO$_2$—($C_1$-$C_6$)alkyl, ($C_1$-$C_6$)alkylHN—SO$_2$—($C_1$-$C_6$)alkyl, [($C_1$-$C_6$)alkyl]$_2$N—SO$_2$—($C_1$-$C_6$)alkyl, CF$_3$—$C_6$)alkyl-SO$_3$—, phenyl phenoxy, benzyloxy, ($C_3$-$C_{10}$)cycloalkyl, ($C_2$-$C_9$)heterocycloalkyl, and ($C_2$-$C_9$)heteroaryl; wherein R$^3$ is hydrogen, ($C_1$-$C_{10}$)alkyl, ($C_3$-$C_{10}$)cycloalkyl-(CH$_2$)$_n$—, ($C_2$-$C_9$)heterocycloalkyl-(CH$_2$)$_n$—, ($C_2$-$C_9$)heteroaryl-(CH$_2$)$_n$— or aryl-(CH$_2$)$_n$—; wherein n is an integer from zero to six;

wherein said $R_3$ ($C_1$-$C_{10}$)alkyl group may optionally be substituted with one or more substituents, (preferably from one to three substituents) independently selected from hydrogen, halo, CN, ($C_1$-$C_6$)alkyl, hydroxy, hydroxy-($C_1$-$C_6$)alkyl, ($C_1$-$C_6$)alkoxy, ($C_1$-$C_6$)alkoxy($C_1$-$C_6$)alkyl, HO—(C═O)—, ($C_1$-$C_6$)alkyl-O—(C═O)—, HO—(C═O)—($C_1$-$C_6$)alkyl, ($C_1$-$C_6$)alkyl-O—(C═O)—($C_1$-$C_6$)alkyl, ($C_1$-$C_6$)alkyl-(C═O)—O—, ($C_1$-$C_6$)alkyl-(C═O)—O—($C_1$-$C_6$)alkyl, H(O═C)—, H(O═C)—($C_1$-$C_6$)alkyl, ($C_1$-$C_6$)alkyl(O═C)—, ($C_1$-$C_6$)alkyl(O═C)—($C_1$-$C_6$)alkyl, NO$_2$, amino, ($C_1$-$C_6$)alkylamino, [($C_1$-$C_6$)alkyl]$_2$amino, amino ($C_1$-$C_6$)alkyl, ($C_1$-$C_6$)alkylamino($C_1$-$C_6$)alkyl, [($C_1$-$C_6$)alkyl]$_2$amino($C_1$-$C_6$)alkyl, H$_2$N—(C═O)—, ($C_1$-$C_6$)alkyl-NH—(C═O)—, [($C_1$-$C_6$)alkyl]$_2$N—(C═O)—, H$_2$N(C═O)—($C_1$-$C_6$)alkyl, ($C_1$-$C_6$)alkyl-HN(C═O)—($C_1$-$C_6$)alkyl, [($C_1$-$C_6$)alkyl]$_2$N—(C═O)—($C_1$-$C_6$)alkyl, H(O═C—NH—, ($C_1$-$C_6$)alkyl(C═O)—NH, ($C_1$-$C_6$)alkyl(C═O)—[NH]($C_1$-$C_6$)alkyl, ($C_1$-$C_6$)alkyl(C═O)—[N($C_1$-$C_6$)alkyl]($C_1$-$C_6$)alkyl, ($C_1$-$C_6$)alkyl-S—, ($C_1$-$C_6$)alkyl-(S═O)—, ($C_1$-$C_6$)alkyl-SO$_2$—, ($C_1$-$C_6$)alkyl-SO$_2$—NH—, H$_2$N—SO$_2$—, H$_2$N—SO$_2$—($C_1$-$C_6$)alkyl, ($C_1$-$C_6$)alkylHN—SO$_2$—($C_1$-$C_6$)alkyl, [($C_1$-$C_6$)alkyl]$_2$ N—SO$_2$—($C_1$-$C_6$)alkyl, CF$_3$SO$_3$—, ($C_1$-$C_6$)alkyl-SO$_3$—, phenyl, ($C_3$-$C_{10}$)cycloalkyl, ($C_2$-$C_9$)heterocycloalkyl, and ($C_2$-$C_9$)heteroaryl; and wherein any of the carbon-carbon single bonds of said ($C_1$-$C_{10}$)alkyl may optionally be replaced by a carbon-carbon double bond;

wherein the ($C_3$-$C_{10}$)cycloalkyl moiety of said $R_3$($C_3$-$C_{10}$) cycloalkyl-(CH$_2$)$_n$— group may optionally be substituted by one to three substitutents independently selected from the group consisting of hydrogen, halo, CN, ($C_1$-$C_6$)alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, $[(C_1$-$C_6)$alkyl$]_2$amino, amino$(C_1$-$C_6)$alkyl, $(C_1$-$C_6)$alkylamino$(C_1$-$C_6)$alkyl, $[(C_1$-$C_6)$alkyl$]_2$amino$(C_1$-$C_6)$alkyl, $H_2N$—C=O)—, $(C_1$-$C_6)$alkyl-NH—(C=O)—, $[(C_1$-$C_6)$alkyl$]_2$N—(C=O)—, $H_2N$(C=O)—$(C_1$-$C_6)$alkyl, $(C_1$-$C_6)$alkyl-HN(C=O)—$(C_1$-$C_6)$alkyl, $[(C_1$-$C_6)$alkyl$]_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkyl HN—$SO_2$—$(C_1$-$C_6)$alkyl, $[(C_1$-$C_6)$alkyl$]_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl;

wherein the $(C_2$-$C_9)$heterocycloalkyl moiety of said $R_3$ $(C_2$-$C_9)$heterocycloalkyl-$(CH_2)_n$— group may contain from one to three heteroatoms independently selected from nitrogen, sulfur, oxygen, >S(=O), >$SO_2$ or >$NR^6$, wherein said $(C_2$-$C_9)$heterocycloalkyl moiety of said $(C_2$-$C_9)$heterocycloalkyl-$(CH_2)_n$— group may optionally be substituted on any of the ring carbon atoms capable of forming an additional bond (preferably one to three substitutents per ring) with a substituent independently selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, $[(C_1$-$C_6)$alkyl$]_2$amino, amino$(C_1$-$C_6)$alkyl, $(C_1$-$C_6)$alkylamino$(C_1$-$C_6)$alkyl, $[(C_1$-$C_6)$alkyl$]_2$amino$(C_1$-$C_6)$alkyl, $H_2N$—(C=O)—, $(C_1$-$C_6)$alkyl-NH—(C=O)—, $[(C_1$-$C_6)$alkyl$]_2$N—(C=O)—, $H_2N$(C=O)—$(C_1$-$C_6)$alkyl, $(C_1$-$C_6)$alkyl-HN(C=O)—$(C_1$-$C_6)$alkyl, $[(C_1$-$C_6)$alkyl$]_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkylHN—$SO_2$—$(C_1$-$C_6)$alkyl, $[(C_1$-$C_6)$alkyl$]_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl;

wherein the $(C_2$-$C_9)$heteroaryl moiety of said $R^3$ $(C_2$-$C_9)$heteroaryl-$(CH_2)_n$— group may contain from one to three heteroatoms independently selected from nitrogen, sulfur or oxygen, wherein said $(C_2$-$C_9)$heteroaryl moiety of said $(C_2$-$C_9)$heteroaryl-$(CH_2)_n$— group may optionally be substituted on any of the ring carbon atoms capable of forming an additional bond (preferably one to three substitutents per ring) with a substituent selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, $[(C_1$-$C_6)$alkyl$]_2$amino, amino$(C_1$-$C_6)$alkyl, $(C_1$-$C_6)$alkylamino$(C_1$-$C_6)$alkyl, $[(C_1$-$C_6)$alkyl$]_2$amino$(C_1$-$C_6)$alkyl, $H_2N$—(C=O)—, $(C_1$-$C_6)$alkyl-NH—(C=O)—, $[(C_1$-$C_6)$alkyl$]_2$N—(C=O)—, $H_2N$(C=O)—$(C_1$-$C_6)$alkyl, $(C_1$-$C_6)$alkyl-HN(C=O)—$(C_1$-$C_6)$alkyl, $[(C_1$-$C_6)$alkyl$]_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkyl HN—$SO_2$—$(C_1$-$C_6)$alkyl, $[(C_1$-$C_6)$alkyl$]_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl; and wherein said aryl moiety of said $R_3$ aryl-$(CH_2)_n$— group is optionally substituted phenyl or naphthyl, wherein said phenyl and naphthyl may optionally be substituted with from one to three substituents independently selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)—$(C_1$-$C_6)$alkyl, $(C_1$-$C_6)$alkyl-O—(C=O)—$(C_1$-$C_6)$alkyl, $(C_1$-$C_6)$alkyl-(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, $[(C_1$-$C_6)$alkyl$]_2$amino, amino$(C_1$-$C_6)$alkyl, $(C_1$-$C_6)$alkylamino$(C_1$-$C_6)$alkyl, $[(C_1$-$C_6)$alkyl$]_2$amino$(C_1$-$C_6)$alkyl, $H_2N$—(C=O)—, $(C_1$-$C_6)$alkyl—NH—C=O)—, $[(C_1$-$C_6)$alkyl$]_2$N—(C=O)—, $H_2N$(C=O)—$(C_1$-$C_6)$alkyl, $(C_1$-$C_6)$alkyl-HN(C=O)—$(C_1$-$C_6)$alkyl, $[(C_1$-$C_6)$alkyl$]_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkyl HN—$SO_2$—$(C_1$-$C_6)$alkyl, $[(C_1$-$C_6)$alkyl$]_2$N—$SO_2$($C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl;

or $R_3$ and the carbon to which it is attached form a five to seven membered carbocyclic ring, wherein any of the carbon atoms of said five membered carbocyclic ring may optionally be substituted with a substituent selected from the group consisting of hydrogen, halo, CN, $(C_1$-$C_6)$alkyl, hydroxy, hydroxy-$(C_1$-$C_6)$alkyl, $(C_1$-$C_6)$alkoxy, $(C_1$-$C_6)$alkoxy$(C_1$-$C_6)$alkyl, HO—(C=O)—, $(C_1$-$C_6)$alkyl-O—(C=O)—, HO—(C=O)$C_1$-$C_6)$alkyl, $(C_1$-$C_6)$alkyl-O—(C=O)—$(C_1$-$C_6)$alkyl, $(C_1$-$C_6)$alkyl—(C=O)—O—, $(C_1$-$C_6)$alkyl-(C=O)—O—$(C_1$-$C_6)$alkyl, H(O=C)—, H(O=C)—$(C_1$-$C_6)$alkyl, $(C_1$-$C_6)$alkyl(O=C)—, $(C_1$-$C_6)$alkyl(O=C)—$(C_1$-$C_6)$alkyl, $NO_2$, amino, $(C_1$-$C_6)$alkylamino, $[(C_1$-$C_6)$alkyl$]_2$amino, amino$(C_1$-$C_6)$alkyl, $(C_1$-$C_6)$alkylamino$(C_1$-$C_6)$alkyl, $[(C_1$-$C_6)$alkyl$]_2$amino$(C_1$-$C_6)$alkyl, $H_2N$—(C=O)—, $(C_1$-$C_6)$alkyl—NH—C=O)—, $[(C_1$-$C_6)$alkyl$]_2$N—(C=O)—, $H_2N$(C=O)—$(C_1$-$C_6)$alkyl, $(C_1$-$C_6)$alkyl-HN(C=O)—$(C_1$-$C_6)$alkyl, $[(C_1$-$C_6)$alkyl$]_2$N—(C=O)—$(C_1$-$C_6)$alkyl, H(O=C)—NH—, $(C_1$-$C_6)$alkyl(C=O)—NH, $(C_1$-$C_6)$alkyl(C=O)—[NH]$(C_1$-$C_6)$alkyl, $(C_1$-$C_6)$alkyl(C=O)—[N$(C_1$-$C_6)$alkyl]$(C_1$-$C_6)$alkyl, $(C_1$-$C_6)$alkyl-S—, $(C_1$-$C_6)$alkyl-(S=O)—, $(C_1$-$C_6)$alkyl-$SO_2$—, $(C_1$-$C_6)$alkyl-$SO_2$—NH—, $H_2N$—$SO_2$—, $H_2N$—$SO_2$—$(C_1$-$C_6)$alkyl, $(C_1$-$C_6)$alkylHN—$SO_2$—$(C_1$-$C_6)$alkyl, $[(C_1$-$C_6)$alkyl$]_2$N—$SO_2$—$(C_1$-$C_6)$alkyl, $CF_3SO_3$—, $(C_1$-$C_6)$alkyl-$SO_3$—, phenyl, $(C_3$-$C_{10})$cycloalkyl, $(C_2$-$C_9)$heterocycloalkyl, and $(C_2$-$C_9)$heteroaryl; wherein one of the carbon-carbon bonds of said five to seven membered carbocyclic ring may optionally be fused to an optionally substituted phenyl ring, wherein said substituents may be independently selected from hydrogen, halo, CN, $(C_1-C_6)$alkyl, hydroxy, hydroxy-$C_1-C_6$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$_4$ is hydrogen, $(C_1-C_6)$alkyl, hydroxy, $(C_1-C_6)$alkoxy, hydroxy$(C_1-C_6)$alkyl, $(C_1-C_6)$alkoxy$(C=O)$—, $(C_3-C_{10})$cycloalkyl-$(CH_2)_q$—, $(C_2-C_9)$heterocycloalkyl-$(CH_2)_q$—, $(C_2-C_9)$heteroaryl-$(CH_2)_q$—, phenyl-$(CH_2)_q$—, or naphthyl-$(CH_2)_q$—; wherein said $(C_2-C_9)$heterocycloalkyl, $(C_2-C_9)$heteroaryl, phenyl naphthyl groups may be optionally substituted with one or two substituents from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—(C=O)—$(C_1-C_6)$alkyl, $(C_1-C_6)$alkyl-(C=O)—O—, $(C_1-C_6)$alkyl-(C=O)—O—$(C_1-C_6)$alkyl, H(O=C)—$(C_1-C_6)$alkyl, $(C_1-C_6)$alkyl(O=C)—, $(C_1-C_6)$alkyl(O=C)—$(C_1-C_6)$alkyl, NO$_2$, amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN(C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl-S—, $(C_1-C_6)$alkyl-(S=O)—, $(C_1-C_6)$alkyl-SO$_2$—, $(C_1-C_6)$alkyl-SO$_2$—NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$, phenyl, $(C_3-C_{10})$cycloalkyl, $(C_2-C_9)$heterocycloalkyl, and $(C_2-C_9)$heteroaryl;

wherein R$_5$ is hydrogen, $(C_1-C_6)$alkyl or amino; or R$_4$ and R$_5$ together with the nitrogen atom to which they are attached form a $(C_2-C_9)$heterocycloalkyl group optionally substituted with one or two substituents selected from the group consisting of hydrogen, halo, cyano, $(C_1-C_6)$alkyl, hydroxy, hydroxy-$(C_1-C_6)$alkyl, $(C_1-C_6)$alkoxy, $(C_1-C_6)$alkoxy$(C_1-C_6)$alkyl, HO—(C=O)—, $(C_1-C_6)$alkyl-O—(C=O)—, HO—(C=O)—$(C_1-C_6)$alkyl, $(C_1-C_6)$alkyl-O—$(C_1-C_6)$alkyl, $(C_1-C_6)$alkyl-(C=O)—O—, $(C_1-C_6)$alkyl-(C=O)—O—$(C_1-C_6)$alkyl, H(O=C)—, H(O=C)—$(C_1-C_6)$alkyl, $(C_1-C_6)$alkyl(O=C)—, $(C_1-C_6)$alkyl(O=C)—$(C_1-C_6)$alkyl, NO$_2$), amino, $(C_1-C_6)$alkylamino, [$(C_1-C_6)$alkyl]$_2$amino, amino$(C_1-C_6)$alkyl, $(C_1-C_6)$alkylamino$(C_1-C_6)$alkyl, [$(C_1-C_6)$alkyl]$_2$amino$(C_1-C_6)$alkyl, H$_2$N—(C=O)—, $(C_1-C_6)$alkyl-NH—(C=O)—, [$(C_1-C_6)$alkyl]$_2$N—(C=O)—, H$_2$N(C=O)—$(C_1-C_6)$alkyl, $(C_1-C_6)$alkyl-HN (C=O)—$(C_1-C_6)$alkyl, [$(C_1-C_6)$alkyl]$_2$N—(C=O)—$(C_1-C_6)$alkyl, H(O=C)—NH—, $(C_1-C_6)$alkyl(C=O)—NH, $(C_1-C_6)$alkyl(C=O)—[NH]$(C_1-C_6)$alkyl, $(C_1-C_6)$alkyl(C=O)—[N$(C_1-C_6)$alkyl]$(C_1-C_6)$alkyl, $(C_1-C_6)$alkyl-S—, $(C_1-C_6)$alkyl-(S=O)—, $(C_1-C_6)$alkyl-SO$_2$—, $(C_1-C_6)$alkyl-SO$_2$NH—, H$_2$N—SO$_2$—, H$_2$N—SO$_2$—$(C_1-C_6)$alkyl, $(C_1-C_6)$alkylHN—SO$_2$—$(C_1-C_6)$alkyl, [$(C_1-C_6)$alkyl]$_2$N—SO$_2$—$(C_1-C_6)$alkyl, CF$_3$SO$_3$—, $(C_1-C_6)$alkyl-SO$_3$—, phenyl, $(C_3-C_{10})$cycloalkyl, $(C_2-C_9)$heterocycloalkyl, and $(C_2-C_9)$heteroaryl;

wherein R$^6$ is hydrogen, $(C_1-C_6)$alkyl, $(C_1-C_6)$alkoxy-$(CH_2)_g$—, $(C_1-C_6)$alkoxy(C=O)—$(CH_2)_g$—, $(C_1-C_6)$alkyl-SO$_2$)—$(CH_2)_g$—, $(C_6-C_{10})$aryloxy-$(CH_2)_g$—, $(C_6-C_{10})$aryloxy(C=O)—$(CH_2)_g$—, or $(C_6-C_{10})$aryl-(SO$_2$)—$(CH_2)_g$—;

wherein g is an integer from zero to four;

wherein m is an integer from zero to four;

wherein n is an interger from zero to six; with the proviso that when one of R$^4$ or R$^5$ is hydrogen, and the other of R$^4$ or R$^5$ is $(C_1-C_6)$alkyl; R$^2$ is $(C_3-C_{10})$cycloalkyl or isopropyl and R$^3$ is $(C_3-C_5)$alkyl, phenyl, methylvinyl, dimethylvinyl, halovinyl, hydroxy$(C_1-C_3)$alkyl or amino$(C_1-C_4)$alkyl then R$^1$ must be other than indol-5-yl, 6-azaindol-2-yl, 2,3-dichloro-pyrrol-5-yl, 4-hydroxyquinolin-3-yl, 2-hydroxyquinoxalin-3-yl, 6-azaindolin-3-yl, or optionally substituted indol-2 or 3-yl; and the pharmaceutically acceptable salts of such compounds.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Such alkyl and alkoxy groups may be substituted with one, two or three halogen and/or hydroxy atoms, preferably fluorine atoms.

Unless otherwise indicated, "halogen" includes fluorine, chlorine, bromine, and iodine.

"$(C_3-C_{10})$cycloalkyl" when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl, and the like.

"$(C_2-C_9)$heterocycloalkyl" when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, and the like. One of ordinary skill in the art will understand that the connection of said $(C_2-C_9)$heterocycloalkyl rings is through a carbon or a sp$^3$ hybridized nitrogen heteroatom.

"$(C_2-C_9)$heteroaryl" when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, and the like. One of ordinary skill in the art will understand that the connection of said ($C_2$-$C_9$)heterocycloalkyl rings is through a carbon atom or a sp3 hybridized nitrogen heteroatom.

"Aryl" when used herein refers to phenyl or naphthyl.

"Protected amine" and "protected amino" refers to an amine group with one of the hydrogen atoms replaced with a protecting group (P). Any suitable protecting group may be used for amine protection. Suitable protecting groups include carbobenzyloxy, t-butoxy carbonyl (BOC) or 9-fluorenylmethylenoxy carbonyl.

Compounds of Formula CCR1-I and their methods of manufacture are disclosed in commonly assigned U.S. patent application Ser. No. 09/380,269, filed Feb. 5, 1998, U.S. patent application Ser. No. 09/403,218, filed Jan. 18, 1999, PCT Publication No. WO98/38167, and PCT Publication No. WO99/40061, all of which are incorporated herein by reference in their entireties for all purposes.

In a preferred embodiment, the CCR1 inhibitor is selected from one of the following compounds of Formula CCR1-I:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid(1S)-benzyl-4(R)-carbamoyl-2(S),7-dihydroxy-7-methyl-octyl)-amide;

6,7,8-trifluoro-quinoline-3-carboxylic acid(1(S)-benzyl-4(R)-carbamoyl-2(S),7-dihydroxy-7-methyl-octyl)-amide;

quinoxaline-2-carboxylic acid[4(R)-carbamoyl-1(S)-(3-fluoro-benzyl)-2(S),7-dihydroxy-7-methyl-octyl]-amide;

quinoxaline-2-carboxylic acid(1(S)-benzyl-2(S),7-dihydroxy-4(R)-hydroxycarbamoyl-7-methyl-octyl)-amide;

quinoxaline-2-carboxylic acid[4(R)-carbamoyl-1(S-(2-chloro-benzyl)-2(S),7-dihydroxy-7-methyl-octyl]-amide;

quinoxaline-2-carboxylic acid[1(S)-(2-fluoro-benzyl)-2(S),7-dihydroxy-4(R)-hydroxycarbamoyl-7-methyl-octyl]-amide;

quinoxaline-2-carboxylic acid[4(R)-carbamoyl-1(S)-(2-fluoro-benzyl)-2(S),7-dihydroxy-7-methyl-octyl]-amide;

quinoxaline-2-carboxylic acid[1(S)-(3,4-difluoro-benzyl)-2(S),7-dihydroxy-4(R)-hydroxycarbamoyl-7-methyl-octyl]-amide;

quinoxaline-2-carboxylic acid[4(R)-carbamoyl-1(S)-(3,4-difluoro-benzyl)-2(S),7-dihydroxy-7-methyl-octyl]-amide;

quinoxaline-2-carboxylic acid(4(R)-carbamoyl-2(S),7-dihydroxy-7-methyl-1(S)-naphthalen-1-ylmethyl-octyl)-amide;

7,8-difluoro-quinoline-3-carboxylic acid 1(S)-benzyl-2(S)-hydroxy-7-methyl-4(R)-methylcarbamoyl-octyl)-amide;

8-fluoro-quinoline-3-carboxylic acid 1(S)-benzyl-2(S)-hydroxy-7-methyl-4(R)-methylcarbamoyl-octyl)-amide;

quinoxaline-2-carboxylic acid[4(R)-carbamoyl-7-fluoro-1-(3(S)-fluoro-benzyl)-2(S)-hydroxy-7-methyl-octyl]-amide;

quinoxaline-2-carboxylic acid[4(R)-carbamoyl-1-(2(S)-fluoro-benzyl)-2(S)-hydroxy-7-methyl-octyl]-amide;

quinoxaline-2-carboxylic acid[1(S)-benzyl-4(S)-carbamoyl-4(S)-(2,6-dimethyl-tetrahydro-pyran-4-yl)-2(S)-hydroxy-butyl]-amide;

quinoxaline-2-carboxylic acid 1(S)-benzyl-4(R)-carbamoyl-7-fluoro-2(S)-hydroxy-7-methyl-octyl)-amide;

quinoxaline-2-carboxylic acid 1(S)-benzyl-5-cyclohexyl-2(S)-hydroxy-4(R)-methylcarbamoyl-pentyl)-amide;

quinoxaline-2-carboxylic acid 1(S)-cyclohexylmethyl-2(S)-hydroxy-7-methyl-4(R)-methylcarbamoyl-octyl)-amide;

quinoxaline-2-carboxylic acid[1(S)-benzyl-2(S)-hydroxy-4(S)-hydroxycarbamoyl-4-(1-hydroxy-4-methyl-cyclohexyl)-butyl]-amide;

quinoxaline-2-carboxylic acid[1(S)-benzyl-4(S)-(4,4-difluoro-1-hydroxy-cyclohexyl)-2(S)-hydroxy-4-hydroxycarbamoyl-butyl]-amide;

quinoxaline-2-carboxylic acid[1(S)-benzyl-4(S)-carbamoyl-4(S)-(4,4-difluoro-cyclohexyl)-2(S)-hydroxy-butyl]-amide;

quinoline-3-carboxylic acid(1(S)-benzyl-4(S)-carbamoyl-4-cyclohexyl-2(S)-hydroxy-butyl)-amide;

quinoxaline-2-carboxylic acid(4(R)-carbamoyl-2(S)-hydroxy-7-methyl-1(S)-thiophen-2-ylmethyl-octyl)-amide;

quinoxaline-2-carboxylic acid 1(S)-benzyl-4(R)-carbamoyl-7-chloro-2(S)-hydroxy-oct-6-enyl)-amide;

quinoxaline-2-carboxylic acid 1(S)-benzyl-4(R)-carbamoyl-2(S)-hydroxy-5-phenyl-pentyl)-amide;

N-1(S)-benzyl-4(R)-carbamoyl-7-fluoro-2(S)-hydroxy-7-methyl-octyl)-5,6-dichloro-nicotinamide;

quinoxaline-2-carboxylic acid(4(R)-carbamoyl-2(S)-hydroxy-7-methyl-1(S)-thiazol-4(R)-ylmethyl-octyl)amide;

benzothiazole-2-carboxylic acid 1(S)-benzyl-4(R)-carbamoyl-7-fluoro-2(S)hydroxy-7-methyl-octyl)-amide; and benzofuran-2-carboxylic acid 1(S)-benzyl-4(R)-carbamoyl-7-fluoro-2(S)-hydroxy-7-methyl-octyl)-amide.

In another preferred embodiment, the CCR1 compound has a formula Ia-1:

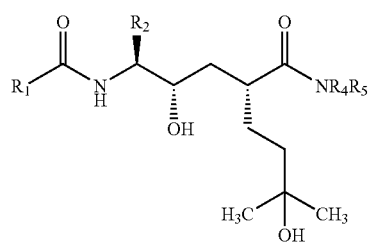

(Ia-1)

wherein the substituents are as defined above.

In a preferred method of making the compound Ia-1, the reaction is started with Scheme 1. In the herein described processes, the substituents are as defined for CCR1-I, and the following:

$R_7$ is hydroxy, ($C_1$-$C_6$)alkyl, or phenyl wherein the phenyl group unsubstituted or substituted with one, two, or three ($C_1$-$C_6$)alkyl, hydroxy, or halogen groups;

$R_8$ is hydroxy or halogen;

$R_9$ is phenyl, naphthyl, ($C_3$-$C_{10}$)cycloalkyl, ($C_1$-$C_6$)alkyl or ($C_2$-$C_9$)heteroaryl, wherein each of said phenyl, naphthyl, ($C_3$-$C_{10}$)cycloalkyl or ($C_2$-$C_9$)heteroaryl groups may be unsubstituted or substituted with one, two, or three substituents independently selected from the group consisting of halogen, cyano, and ($C_1$-$C_6$)alkyl;

P is a protecting group;

X is hydroxy or halogen; and q is 0, 1, 2, 3, or 4.

Scheme 1

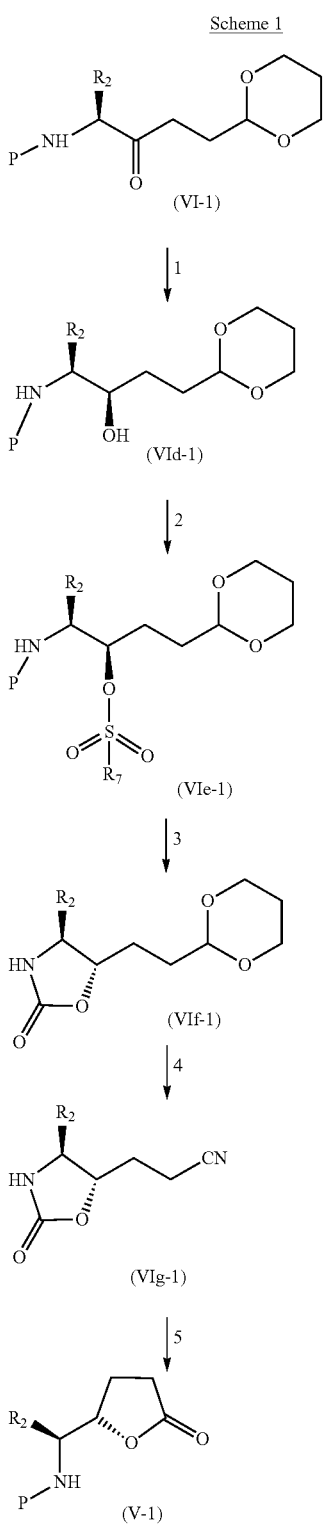

mixture to room temperature, diluting with more isopropanol and collecting the crystalline material or by cooling the reaction to room temperature and adding 1N HCL and water and collecting the crystalline material.

Step 2 of scheme 1 includes reacting a compound of the formula $R_7$—$SO_2$—X and a compound of the formula (VId-1) in the presence of a base to form the compound of the formula (VIe-1). Any amine base is suitable, including pyridine, triethylamine, N-methylmayholine, and diisoyropylethylamine. In one embodiment, $R_7$—SO2-$R_8$ is p-toluenesulfonic acid, methanesulfonic acid, sulfuric acid, or methanesulfonyl chloride. In another embodiment, the conversion of hydroxy dioxane (VId-1) to dioxane oxazolidinone (VIe-1) can be achieved by treatment of the hydroxy dioxane (VId-1) with methanesulfonyl chloride and triethylamine in tetrahydrofuran solution and heating the mixture to cause the cyclization of the mesylate formed in situ to the oxazolidinone.

In step 3 of scheme 1, a compound of the formula (VIf-1) may be formed by heating the compound of the formula (VIe-1). The reaction may proceed by dissolving compound VIe-1 in a solvent such as pyridine or N-methyl imidazole and heating the mixture for several hours at temperature from about 50° C. to about 100° C.; preferably at about 80° C. The mesylate (VIf-1) may be recovered by extraction into an organic solvent such as ethyl acetate and removal of the amine solvents by extraction of the solution with aqueous acid.

Step 4 of scheme 1 depicts reacting hydroxylamine hydrochloride, a compound of the formula $R_7$—$SO_2$—X, and a compound of the formula (VIf-1) to form a compound of the formula (VIg-1). In one embodiment, $R_7$—SO2-X is p-toluenesulfonic acid, methanesulfonic acid, sulfuric acid, or methanesulfonyl chloride. The reaction may occur in a solvent, such as methanol. In one embodiment, the reaction occurs in methanol with tosic acid at reflux for 8 to 24 hours. The resulting nitrile oxazolidinone contains a small amount of the corresponding ethyl ester which is not removed since it also is converted to the desired lactone in subsequent steps.

Step 5 of scheme 1 includes a) hydrolyzing a compound of the formula (VIg-1) with an aqueous solution in the presence of a base, b) protecting the amine group of the compound so formed, and c) cyclizing the compound so formed with heat and an acid catalyst. In one embodiment, the compound VIg-1 is hydrolyzed with sodium hydroxide. The pH is adjusted to approximately 10 and tetrahydrofuran and BOC dicarbonate are added. This provides the protected hydroxy acid, which may be heated in 10% acetic acid and toluene to provide the protected amine lactone (V-1).

The compound of formula (V-1) may also be produced according to scheme 2.

In scheme 1 step 1, a compound of the formula (VI-1) is reduced with a reducing agent under heat to form a compound of the formula (VId-1). In one embodiment, the reducing agent is aluminum triisopropoxide and isopropanol. Preferably, the temperature is maintained above room temperature, more preferably between about 60° C. and about 82° C. The product alcohol can be isolated by either cooling the reaction

Scheme 2

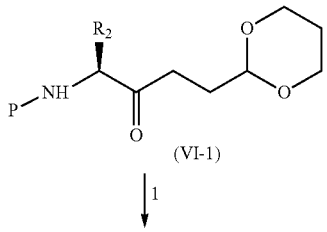

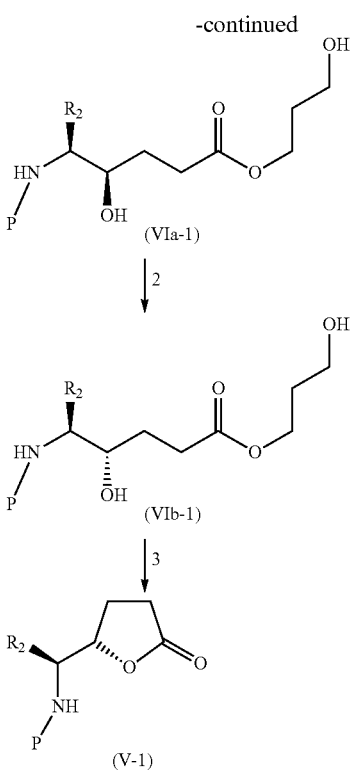

In step 1 of scheme 2, a compound of the formula (VI-1) may be reacted with ozone to for a compound of the formula (VIa-1). The compound VI-1 may be present in a solvent, such as ethyl acetate, and the ozone introduced through sparging at a temperature below room temperature, preferably at about −15° C., until the starting dioxane ketone is substantially reacted. Any excess ozone may be removed by bubbling nitrogen through the solution. The resulting crude ketone ester mixture may be isolated after treatment with aqueous sodium bisulfite to remove any hydroperoxides.

Alternatively, in step 1 of scheme 2, the compound of the formula (VIa-1) may be formed by reacting hypochlorous acid and a compound of the formula (VI-1). Such an oxidation reaction typically produces chlorinated forms of the compound VIa-1 as side products in addition to the compound VIa-1. This oxidation reaction proceeds by mixing the compound VI-1 in solvent, such as acetic acid and/or acetone, and adding sodium hypochlorite, while keeping the mixture at a low temperature, preferably at or below about 0° C.

As a means to convert the side product chlorinated forms of the compound VIa-1 to compounds of the formula V-1, the compounds formed from the hypochlorous acid oxidation reaction may optionally be hydrogenated by reaction with hydrogen in the presence of a catalyst. The hydrogenation may include introducing the products from the hypochlorous acid oxidation reaction into a solvent system of tetrahydrofuran and water, followed by addition of a Pd/C catalyst. The resulting mixture is subjected to hydrogen above atmospheric pressure and temperature. In one embodiment, the pressure is about 80 pounds per square inch and the temperature is maintained from about 60° C. to about 70° C. until the reaction is substantially complete.

In step 2 of scheme 2, the compound of the formula (VIb-1) may be formed by reacting a silyating agent and a compound of the formula (VIa-1) and reacting the compound so formed with a reducing agent. In one embodiment, the reducing agent is N-selectride. In another emodiment, the silyating agent is 1,1,1,3,3,3-hexamethyl-disilazane. The reduction reaction may occur at temperatures below about 0° C., preferably below about −20° C., more preferably below about −50° C. In addition, the reducing agent may be present in slight excess.

In step 3 of scheme 2, the compound of the formula (V-1) is formed by heating a compound of the formula (VIb-1) in the presence of an acid catalyst, such as acetic acid. In one embodiment, the cyclization reaction occurs by introducing the compound VIb-1 into a solvent mixture, such as toluene and 10% acetic acid, at the solvent reflux temperature for 8 to 16 hours. This provides the desired lactone as a crystalline solid after work up.

One method of making the compound of the formula (VI-1) is by reacting a compound of the formula (VII-1)

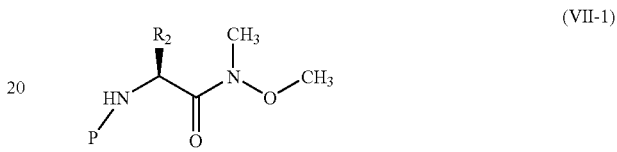

with a Grinard reagent formed in situ by addition of 2-(2-bromo-ethyl)-[1,3]dioxane to a mixture comprising magnesium and the compound of the formula (VII-1). In one embodiment, the mixture further comprises methyl magnesium chloride and/or methyl magnesium bromide in a solvent. Any exotherm formed from the reaction may be controlled by the rate of addition of the bromide. The compound of the formula (VII-1) may be formed by coupling N,O-dimethylhydroxylamine hydrochloride and a compound of the formula (VIII-1)

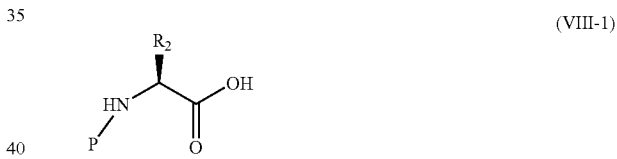

This coupling reaction may be performed by mixed anhydride procedure. In one mixed anhydride procedure, compound VII-1 is combined with methylene chloride and N-methylmorpholine is added followed by isobutyl chloroformate. In a separate mixture, a slurry of N,O-dimethylhydroxylamine hydrochloride is treated with N-methylmorpholine. The two reaction mixtures are combined and then quenched with a solution of citric acid in water. This procedure preferably operates at a temperature below about 20° C., more preferably below about 0° C.

Compounds of formula (V-1) may be used to produce compounds of the formula (IVa1-1) according to scheme 3:

Scheme 3

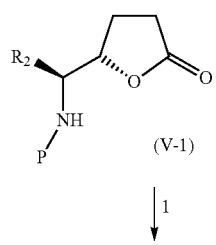

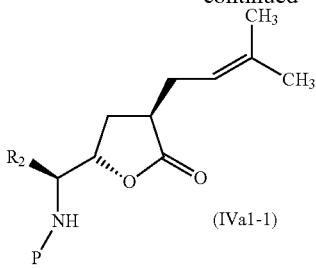

(IVa1-1)

In step 1 of scheme 3, the compound of the formula (IVa1-1) may be formed by reacting 4-halo-2-methyl-2-butene and a compound of the formula (V-1) in the presence of a base. Exemplary bases include lithium dialkyl amides such as lithium N-isopropyl-N-cyclohexylamide, lithium bis(trimethylsilyl)amide, lithium di-isopropylamide, and potassium hydride. Suitable solvents include aprotic polar solvents such as ethers (such as tetrahydrofuran, glyme or dioxane), benzene, or toluene, preferably tetrahydrofuran. The aforesaid reaction is conducted at a temperature from about −78° C. to about 0° C., preferably at about −78° C. In one embodiment, alkylation of the lactone (V-1) is accomplished by reacting the lactone (V-1) with lithium bis(trimethylsilyl)amide and dimethylallyl bromide in tetrahydrofuran at a temperature from about −78° C. to about −50° C. Reaction times range from several hours or if an additive such as dimethyl imidazolidinone is present, the reaction may be complete in minutes.

Compounds of formula (IVa1-1) may be used to produce compounds of the formula (Ia-1) according to scheme 4:

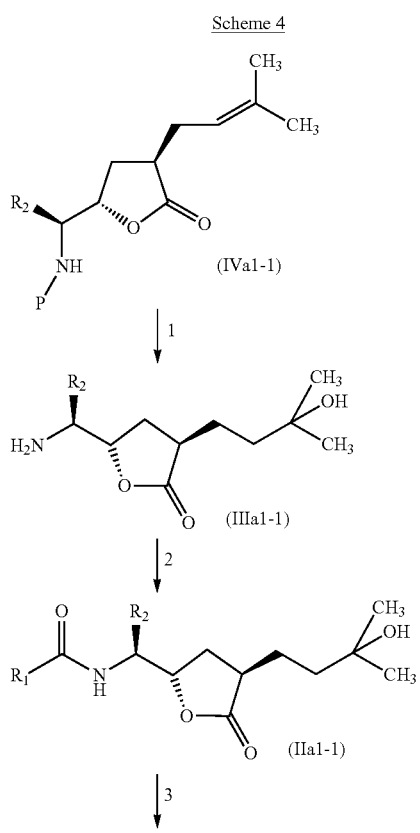

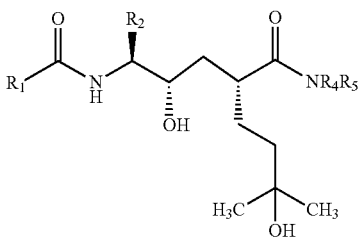

(Ia-1)

In step 1 of scheme 4, a compound of the formula (IIIa1-1) is formed by reacting a compound of the formula (IVa1-1) with phosphoric acid. Preferably, this reaction occurs in any suitable solvent, such as non-alcoholic solvents. Two preferred solvents include tetrahydrofuran and dichloroethane. The reaction may take place at any suitable temperature, preferably from about −25° C. to about 120° C., more preferably from about 15° C. to about 40° C. Reaction time is dependent on temperature and batch size, amount other factors, but typically reaction time is from about 2 hours to about 14 hours.

Step 2 of scheme 4 depicts coupling a compound IIIa1-1 with a compound having the formula $R_1$—CO—X to form a compound having the formula (IIa1-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI), and diethylphosphorylcyanide. The coupling is conducted in an inert solvent, preferably an aprotic solvent, such as tetrahydrofuran, acetonitirile, dichloromethane, chloroform, or N,N-dimethylformamide. One preferred solvent is tetrahydrofuran. In one embodiment, quinoxaline acid is combined with CDI in anhydrous tetrahydrofuran and heated to provide the acyl imidazole. Compound IIIa1-1 is added to the acyl imidazole at room temperature to form the compound IIa1-1.

Step 3 of scheme 4 includes reacting the compound of formula IIa1-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa1-1 is dissolved in methanol which has been saturated with ammonia gas. In another embodiment, the compound IIa1-1 in methanol is treated with ammonium hydroxide in tetrahydrofuran at room temperature.

Scheme 5 represents an alternative method to form compounds of formula Ia-1 from compounds of formula IVa1-1.

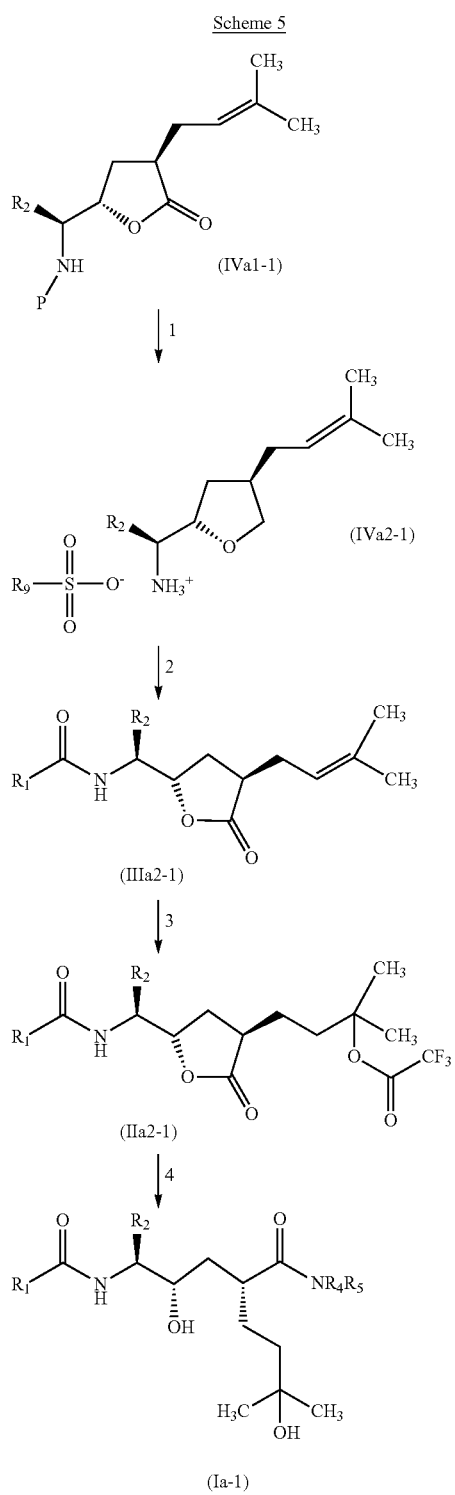

In step 1 of scheme 5, a compound of the formula (IVa1-1) is reacted with a compound of the formula $R_9$—$SO_2$—X to form a compound of the formula (IVa2-1). Any suitable acidic deprotection reaction may be performed. In one example, an excess of p-toluenesulfonic acid hydrate in ethyl acetate is introduced to the compound IVa1-1 at room temperature. Suitable solvents include ethyl acetate, alcohols, tetrahydrofuran, and mixtures thereof. The reaction may proceed at ambient or elevated temperatures. Typically, the reaction is substantially complete within two and twelve hours. The resulting compound IVa2-1 may be crystallized and separated from the reaction mixture, and may be further purified to remove impurities by recrystallization from hot ethyl acetate.

In step 2 of scheme 5, the compound IVa2-1 may be coupled with a compound having the formula $R_1$—CO—X to form a compound of the formula (IIIa2-1). This coupling reaction is generally conducted at a temperature from about −30° C. to about 80° C., preferably from about 0° C. to about 25° C. The coupling reaction may occur with a coupling reagent that activates the acid functionality. Exemplary coupling reagents include dicyclohexylcarbodiimide/hydroxybenzotriazole (DCC/HBT), N-3-dimethylaminopropyl-N'-ethylcarbodiimide (EDC/HBT), 2-ethyoxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitrile, dichloromethane, chloroform, or N,N-dimethylformamide. One preferred solvent is methylene chloride. In one embodiment, quinoxaline acid is combined with methylene chloride, oxalyl chloride and a catalytic amount of N,N-dimethylformamide to form an acid chloride complex. The compound IVa2-1 is added to the acid chloride complex followed by triethylamine at a temperature from about 0° C. to about 25° C. to form the compound IIIa2-1.

Step 3 of scheme 5 includes reacting a compound IIIa2-1 with trifluoroacetic acid to produce a compound of the formula (IIa2-1). In one embodiment, the hydration with trifluoroacetic acid occurs in methylene chloride solution at room temperature. The hydration may take several hours to complete at room temperature. A catalytic amount of sulfuric acid can be added to the reaction solution to increase the rate of reaction.

Step 4 of scheme 5 includes reacting the compound of formula IIa2-1 with an amine having a formula $NHR_4R_5$ to form a compound of the formula (Ia-1). In one embodiment, the amine is ammonia either anhydrous in an organic solvent or as an aqueous solution of ammonium hydroxide added to a polar solvent at a temperature from about −10° C. to about 35° C., preferably at about 30° C. Suitable solvents include, alcohols, such as methanol, ethanol, or butanols; ethers such as tetrahydrofuran, glyme or dioxane; or a mixture thereof, including aqueous mixtures. Preferably the solvent is methanol. In one embodiment, the compound IIa2-1 is dissolved in methanol which has been saturated with ammonia gas. In another embodiment, the compound IIa2-1 in methanol is treated with ammonium hydroxide in tetrahydrofuran at room temperature.

Neutralized Acidic Polymers

Polymers suitable for use in the compositions of the present invention should be pharmaceutically acceptable, and have at least some solubility in aqueous solution at physiologically relevant pHs (e.g. 1-8). The polymer should have an aqueous-solubility of at least 0.1 mg/mL over at least a portion of the pH range of 1-8. The polymer is "concentration-enhancing" as described in more detail below.

While specific polymers are discussed as being suitable for use in the compositions of the present invention, blends of such polymers may also be suitable. Thus the term "polymer" is intended to include blends of polymers in addition to a single species of polymer.

By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Here, the term $pK_a$ is used in its traditional form, the $pK_a$ being the negative logarithm of the acid ionization constant. The $pK_a$ will be influenced by such factors as solvent, temperature, water content, and ionic strength of the media or matrix in which the acid resides. Unless otherwise noted, the $pK_a$ is assumed to be measured in distilled water at 25° C. Since in general, the more acidic the polymer the more useful the invention, the invention is preferred for polymers with functional groups with $pK_a$s of less than about 7, and even more preferred with $pK_a$s of less than about 6. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents."

By "neutralized acidic polymer" is meant any acidic polymer for which a significant fraction of the "acidic moieties" or "acidic substituents" have been "neutralized"; that is, exist in their deprotonated form. The "degree of neutralization," $\alpha$, of a polymer substituted with monoprotic acids (such as carboxylic acids) is defined as the fraction of the acidic moieties on the polymer that have been neutralized; that is, deprotonated by a base. The degree to which the acidic moieties on the polymer are neutralized by the base is dependent on (1) the ratio of the number of milliequivalents of base per gram of polymer divided by the number of milliequivalents of acidic moieties per gram of polymer and (2) the relative $pK_a$s of the base and the acidic polymer. When the $pK_a$ of the base is much higher than the $pK_a$ of the acidic moieties of the acidic polymer (that is, the ratio of the $pK_a$ of the base to the $pK_a$ of the polymer $\geq 2$), then each milliequivalent of base will approximately neutralize one milliequivalent of acid. Thus, if 0.5 milliequivalent of a strong base per gram of polymer is added to an acidic polymer with 1.0 milliequivalents of acidic moieties per gram of polymer, then the degree of neutralization is roughly equal to 0.5.

If a relatively weak base with a $pK_a$ value roughly equal to that of the polymer's acidic moieties is used to neutralize the polymer (e.g., the base is the sodium salt of an aliphatic carboxylic acid, such as sodium propionate, and the acidic groups on the polymer are aliphatic carboxylic acids, such as succinate), then more base must be added to achieve the same extent of neutralization. Thus, if 1.0 milliequivalent of a base per gram of polymer, with a $pK_a$ roughly equal to the $pK_a$ of the polymer, is added to an acidic polymer with 1.0 milliequivalents of acidic moieties per gram of polymer, then the degree of neutralization is roughly also equal to 0.5.

When the degree of neutralization, $\alpha$, is less than 0.9, it may be approximated by the following equation:

$$\alpha = \frac{E_{base}}{E_{polymer}} \cdot 1 + \frac{10^{pKa,Base-pKa,Polymer}}{10^{pKa,Base-pKa,Polymer}}$$

where $E_{base}$ is the number of milliequivalents of base per gram of polymer, $E_{polymer}$ is the number of milliequivalents of acidic moieties (of the polymer) per gram of polymer, and $pK_a$,Base and $pK_a$,polymer are the $pK_a$ values of the base and polymer, respectively. It should be noted that if the calculated value of $\alpha$ from this equation is greater than 1, the degree of neutralization can be considered essentially 1, meaning that essentially all of the acidic moieties on the polymer have been neutralized.

Alternatively, the degree of neutralization may be measured experimentally. Although not strictly applicable to organic solutions or solid dispersions, the Henderson-Hasselbach equation can be used to relate the effective pH of an aqueous solution or a hydrated dispersion to the degree of neutralization. According to this equation the effective pH of the solution or hydrated dispersion is given as:

$$pH = pK_a,\text{polymer} - \log[(1-\alpha)/\alpha]$$

As yet another alternative, the degree of neutralization may be determined experimentally through spectroscopic analysis or thermal methods such as differential scanning calorimetry (DSC). Using DSC, for example, conversion of an acidic cellulosic polymer such as HPMCAS to the sodium or calcium salt form will lead to a measurable increase in the glass transition temperature ("$T_g$") of the polymer alone or drug/polymer dispersion. The change in physical characteristic such as glass transition temperature may be used to determine the degree of neutralization.

Typically, for an acidic polymer to be considered a "neutralized acidic polymer," $\alpha$ must be at least about 0.001 (or 0.1%), preferably about 0.01 (1%) and more preferably at least about 0.1 (10%). Such small degrees of neutralization may be acceptable because often the effective pH of the polymer changes dramatically with small increases in the degree of neutralization. Nonetheless, even greater degrees of neutralization are even more preferred. Thus, $\alpha$ is preferably at least 0.5 (meaning that at least 50% of the acidic moieties have been neutralized) and is more preferably at least 0.9 (meaning that at least 90% of the acidic moieties have been neutrralized).

Often the most chemically stable compositions are formed when approximately 100% of the acidic groups of the polymer have been neutralized, that is a is approximately equal to 1.0. In some cases stable dispersions are formed when excess base is present. However, for acid-sensitive drugs that are also base sensitive, it is often preferred for a to be approximately equal to 1.0, as this minimizes the presence of both acid and base. An alternate method involves using excess weak base ($pK_a$ of the base being roughly equal to the $pK_a$ of the polymer's acidic moieties) such that $\alpha$ is about 1.0. The advantage of using a weak base is that even the presence of excess base does not cause the dispersion to become overly basic.

Yet another alternative method for determining whether a significant fraction of the acidic moieties have been neutralized is, in the case of a dispersion comprising an acid-sensitive drug, to disperse the acid-sensitive drug in the neutralized acidic polymer and compare the chemical stability of the drug in the dispersion with the chemical stability of the same drug in a control composition comprised of the same quantity of drug dispersed in the acidic polymer (unneutralized form). A significant fraction of the acidic moieties of the acidic polymer have been neutralized if the acid-sensitive drug degrades more slowly when dispersed in the neutralized acidic polymer relative to the rate it degrades in the control acidic polymer. Thus, only a portion of the acidic moieties or acidic substituents may need to be neutralized. Since the effective pH of an acidic polymer is raised significantly by even a small change in the degree of neutralization, a relatively low degree of neutralization may well result in measurable improvements in the stability of acid-sensitive drugs.

Neutralized acidic polymers may be either cellulosic or non-cellulosic. A preferred class of acidic polymers consists of cellulosic polymers with at least one ester- and/or ether-linked acidic substituent in which the polymer has a degree of substitution of at least 0.02 for the acidic substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents that are ether-linked via the ethoxy group. Analogously, ester-linked substituents are recited after "cellulose" as the carboxylate; for example, "cellulose acetate phthalate" has acetate and phthalate moieties ester-linked to the polymer. Such polymers include at least one acidic substituent, which may be either ether-linked or ester-linked. When substituents possess more than one carboxylic acid group, generally, unless otherwise specified, one carboxylic acid group is ester linked to a hydroxyl group on the polymer backbone and the remaining carboxylic acid group or groups remain as carboxylic acid groups for the "acidic polymer." Thus, phthalate groups for cellulose acetate phthalate are substantially ester-linked to the hydroxyl groups of the cellulose via one carboxylate group while the second carboxylate group for each phthalate remains unreacted.

It should also be noted that a polymer name such as "cellulose acetate phthalate" refers to any of the family of cellulosic polymers that have acetate and phthalate groups attached via ester linkages to a significant fraction of the cellulosic polymer's hydroxyl groups. Generally, the degree of substitution of each substituent group can range from 0.02 to 2.9 as long as the other criteria of the polymer are met. More typically, the degree of substitution for each substituent is from about 0.1 to 2.0. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Exemplary acidic, ether-linked ionizable substituents include: carboxylic acids, such as carboxymethoxy (commonly referred to as carboxymethyl), carboxyethoxy (commonly referred to as carboxyethyl), carboxypropoxy (commonly referred to as carboxypropyl), and carboxyphenoxy (commonly referred to as carboxyphenyl), salicylic acid (attached to the cellulosic polymer via the phenolic hydroxyl), alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; phosphates, such as ethoxy phosphate; and sulfonates, such as ethoxy sulphonate.

Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary acidic cellulosic polymers include such polymers as carboxyethyl cellulose, carboxymethyl cellulose, carboxymethyl ethyl cellulose, cellulose succinate, cellulose acetate succinate, hydroxyethyl cellulose succinate, hydroxyethyl cellulose acetate succinate, hydroxyethyl methyl cellulose succinate, hydroxyethyl methyl cellulose acetate succinate, hydroxypropyl cellulose succinate, hydroxypropyl cellulose acetate succinate, hydroxypropyl methyl cellulose acetate succinate, hydroxypropyl methyl cellulose succinate, cellulose phthalate, cellulose acetate phthalate, methyl cellulose acetate phthalate, ethyl cellulose acetate phthalate, cellulose propionate phthalate, hydroxyethyl methyl cellulose acetate phthalate, hydroxypropyl cellulose acetate phthalate, hydroxypropyl methyl cellulose phthalate, hydroxypropyl methyl cellulose acetate phthalate, hydroxypropyl cellulose acetate phthalate succinate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Alternatively, the acidic polymer may be non-cellulosic. Exemplary acidic non-cellulosic polymers include carboxylic acid-functionalized vinyl polymers, such as the carboxylic acid functionalized polymethacrylates and carboxylic acid functionalized polyacrylates such as the EUDRAGITS® manufactured by Rohm Tech, Inc., of Malden, Mass.; and carboxylic acid functionalized starches such as starch glycolate.

The neutralized form of these acidic polymers often provide several advantages relative to the unneutralized form. First, where the composition is a dispersion, the neutralized form of the acidic polymer, i.e., the salt form of the polymer, tends to have a higher glass transition temperature relative to the acidic form of the polymer. To obtain the best physical stability, particularly upon storage for long times prior to use, it is preferred that the drug remain, to the extent possible, in the amorphous state. The inventors have found that this is best achieved when the mobility of the drug in the dispersion polymer is relatively low. This is generally the case when the glass-transition temperature, $T_g$, of the amorphous drug/polymer dispersion is substantially above the storage temperature of the dispersion. In particular, it is preferable that the $T_g$ of the amorphous state of the drug be at least 40° C. and preferably at least 60° C. Where the drug itself has a relatively low $T_g$ (about 70° C. or less), it is preferred that the dispersion polymer have a $T_g$ of at least 40° C., preferably at least 70° C.

and more preferably greater than 100° C. (Unless otherwise specified, as used herein and in the claims, reference to a glass transition refers to the glass transition temperature measured at 50% relative humidity.) Exemplary high $T_g$ polymers include neutralized forms of hydroxypropyl methyl cellulose acetate succinate, hydroxypropyl methyl cellulose phthalate, cellulose acetate phthalate, cellulose acetate trimellitate, and other cellulosics that have alkylate or aromatic substituents or both alkylate and aromatic substituents.

Increasing the glass transition temperature of the polymer, and hence of the dispersion, improves the physical storage stability of the dispersion by decreasing the mobility of drug in the polymer matrix. Thus, dispersions formed from neutralized acidic polymers, which have a higher $T_g$ relative to the unneutralized form, tend to be more physically stable.

When the neutralized form of the acidic polymer comprises a multivalent cationic species such as $Ca^{2+}$, $Mg^{2+}$, $Al^{3+}$, $Fe^{2+}$, $Fe^{3+}$, or a diamine, such as ethylene diamine, the cationic species may interact with two or more neutralized acidic moieties on more than one polymer chain, resulting in an ionic crosslink between the polymer chains. An acidic polymer may be considered "ionically crosslinked" if the number of milliequivalents of multivalent cationic species per gram of polymer is at least 5%, preferably at least 10% the number of milliequivalents of acidic moieties (of the polymer) per gram of polymer. Alternatively, an acidic polymer may be considered "ionically crosslinked" if sufficient multivalent cationic species are present such that the neutralized acidic polymer has a higher $T_g$ than the same polymer containing essentially no multivalent cationic species. Drug mobility in dispersions formed from such ionically crosslinked polymers is particularly low relative to dispersions formed from the acidic form of the same polymers. Such ionically crosslinked polymers may be formed by neutralization of the acidic polymer using any base where the cationic counterion of the base is divalent. Thus, calcium hydroxide, magnesium acetate or ethylene diamine may be added to an acidic polymer such as cellulose acetate phthalate or hydroxypropyl methyl cellulose acetate succinate to form a neutralized, ionically crosslinked, acidic cellulosic polymer. Low drug mobility in such polymers may be indicated by high $T_g$ values or, more typically, a decrease in the magnitude of the heat capacity increase in the vicinity of the $T_g$ or, in some cases, the absence of any apparent $T_g$ when the dispersion is subjected to differential thermal analysis. Thus, when sufficient calcium hydroxide is added to HPMCAS such that the degree of neutralization is near 1, no $T_g$ is apparent when the neutralized polymer is subjected to differential thermal analysis. In addition, an acid-sensitive drug dispersed in this polymer is more chemically and physically stable than when it is dispersed in a non-ionically crosslinked neutralized acidic polymer.

Second, the neutralized form of the acidic polymer also tends to improve concentration enhancement relative to the unneutralized acidic form of the polymer. The present inventors have found that for neutralized acidic polymers, such as hydroxypropyl methyl cellulose acetate succinate, the neutralized form of the acidic polymer can, for some drugs, provide superior concentration enhancement. In addition, the neutralized form of the acidic polymers tend to provide more rapid dissolution of the dispersion. Thus, when the dispersion of the drug and polymer are introduced into the use environment, the dispersion dissolves more rapidly relative to a dispersion of the drug and unneutralized acidic polymer.

Finally, the neutralized form of the acidic polymer tends to be less reactive than the acidic polymer. Thus, in addition to minimizing reactions of the drug with the polymer, the selection of a neutralized acidic enteric polymer also minimizes reactions of the polymer with other excipients.

Neutralized enteric polymers are an especially preferred class of neutralized acidic polymers. First, enteric polymers typically have a higher $T_g$ relative to non-enteric polymers, and those are capable of forming compositions having improved physical stability. Second, enteric polymers often result in greater drug concentration relative to non-enteric polymers.

By "enteric polymer" is meant a polymer which has an aqueous solubility that is higher at neutral pH (pH $\geq 6.5$) than at low pH (pH $\leq 5.5$). Typically, enteric polymers are relatively insoluble at low pH, typically a pH of less than about 5.5, but at least partially soluble at a pH of greater than about 6.5. Exemplary acidic cellulosic enteric polymers have both (1) an acidic substituent such as succinate, phthalate, trimellitate or carboxyalkyl (such as carboxymethyl) and (2) a hydrophobic substituent such as an alkyl or aryl ether (e.g., methyl or ethyl) or an alkyl or aryl ester (e.g., acetate, propionate, butyrate or benzoate). This excludes polymers such as carboxymethyl cellulose because they do not possess one or more hydrophobic substituents and polymers such as methyl cellulose because they do not possess one or more acidic substituents. It should also be noted that for such polymers to have the requisite solubility properties to be "enteric" polymers, the amount or degree of substitution ("d.s.") of each substituent must be at the appropriate level. For example, if the acetate level of a polymer such as HPMCAS is too low (typically a d.s. value of about 0.1 or less), then the polymer will be soluble even at low pH. In contrast, if the acetate level is too high (typically a d.s. value of about 0.4 or more when the succinate level is about 0.1 to 0.4) then the polymer may be insoluble at even high pH (pH $\geq 6.5$).

Exemplary cellulosic acidic enteric polymers include hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxymethyl methyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another class of acidic enteric polymers suitable for use with the present invention comprises ionizable non-cellulosic polymers. Exemplary non-cellulosic acidic enteric polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; and acidic proteins.

Concentration Enhancement

As described above, the neutralized acidic polymers of the present invention are also "concentration-enhancing," meaning that the polymers improve the concentration of the low-solubility drug in a use environment, and thereby preferably improve bioavailability of the drug. A preferred class of concentration-enhancing polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, or esters. It is believed that such amphiphilic polymers act to retard crystallization or precipitation of the drug. Such polymers may thus act to decrease the rate at which the drug falls from the maximum drug concentration (MDC) to the equilibrium concentration of drug.

The term "concentration-enhancing" means that the polymer is present in a sufficient amount in the composition so as to improve the concentration of the drug in a use environment relative to a control composition free from the concentration-enhancing polymer. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PSB) or a Model Fasted Duodenal (MFD) solution. Concentration enhancement may be determined through either in vitro dissolution tests or through in vivo tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition containing a concentration-enhancing polymer may be dissolution-tested by adding it to MFD or PBS solution and agitating to promote dissolution.

In one aspect of the invention, a composition containing a concentration-enhancing polymer of the present invention provides an MDC that is at least 1.25-fold the MDC provided by a control composition. In other words, if the MDC provided by the control composition is 100 μg/mL, then a composition of the present invention containing a concentration-enhancing polymer provides an MDC of at least 125 μg/mL. More preferably, the MDC of drug achieved with the compositions of the present invention are at least 2-fold, even more preferably at least 3-fold, and, most preferably at least 10-fold that provided by the control composition.

The control composition is conventionally the undispersed drug alone (e.g., typically, the crystalline drug alone in its most thermodynamically stable crystalline form, or in cases where a crystalline form of the drug is unknown, the control may be the amorphous drug alone) or the drug plus a weight of inert diluent equivalent to the weight of polymer in the test composition (by inert is meant not concentration-enhancing). Where the composition is comprised of a mixture of a dispersion and additional concentration-enhancing polymer, the control composition is the dispersion alone without any additional concentration-enhancing polymer.

Alternatively, the compositions containing concentration-enhancing polymers of the present invention provide in an aqueous use environment a concentration versus time Area Under The Curve (AUC), for any period of at least 90 minutes between the time of introduction into the use environment and about 270 minutes following introduction to the use environment that is at least 1.25-fold the AUC provided by an appropriate control composition. More preferably, the AUC achieved with the compositions of the present invention are at least 2-fold and more preferably at least 3-fold that of a control composition.

Alternatively, the compositions of the present invention containing concentration-enhancing polymers, when dosed orally to a human or other animal, provide an AUC in drug concentration in the blood plasma or serum that is at least 1.25-fold that observed when an appropriate control composition is dosed. Preferably, the blood AUC is at least 2-fold, more preferably at least 3-fold, that of an appropriate control composition. Thus, the compositions of the present invention can be evaluated in either an in vitro or in vivo test, or both.

A typical in vitro test to evaluate enhanced drug concentration can be conducted by (1) administering with agitation a sufficient quantity of test composition (e.g., the dispersion of the low-solubility drug and neutralized acidic polymer) in a test medium, such that if all of the drug dissolved, the theoretical concentration of drug would exceed the equilibrium concentration of the drug by a factor of at least 2; (2) adding an appropriate amount of a control composition to an equivalent amount of test medium; and (3) determining whether the measured MDC and/or AUC of the test composition in the test medium is at least 1.25-fold that provided by the control composition. The concentration of dissolved drug is typically measured as a function of time by sampling the test medium and plotting drug concentration in the test medium vs. time so that the MDC and/or AUC can be ascertained. In conducting such a dissolution test, the amount of test composition used is an amount such that if all of the drug dissolved the drug concentration would be at least 2-fold to 100-fold that of the solubility of the drug. For some dispersions of very low-solubility drug and acidic neutralized polymer, it may be necessary to administer an even greater amount of the dispersion to determine the MDC.

To avoid drug particulates which would give an erroneous determination, the test solution is either filtered or centrifuged. "Dissolved drug" is typically taken as that material that either passes a syringe micro filter or, alternatively, the material that remains in the supernatant following centrifugation. Filtration can be conducted using any filter with a pore size rating in the 0.2 to 2.0 □g range. In particular, a 13 mm, 0.45 μm polyvinylidine difluoride syringe filter sold by Scientific Resources under the trademark TITAN® may be used. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved drug" encompasses not only monomeric solvated drug molecules but also a wide range of species such as polymer/drug assemblies that have micron or submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the concentration-enhancing polymer results in improved bioavailability. Relative bioavailability of the drug in the compositions of the present invention can be tested in vivo in animals or humans using conventional methods for making such a determination. An in vivo test, such as a crossover study, may be used to determine whether a composition provides an enhanced relative bioavailability compared with a control. In an in vivo crossover study a "test composition" of drug and concentration-enhancing polymer is dosed to half a group of test subjects and, after an appropriate washout period (e.g., one week) the same subjects are dosed with a "control composition" that comprises an equivalent quantity of drug as the "test composition." The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). Generally, the values for AUC represent a number of values taken from all of the subjects in a patient test population averaged over the entire test population.

A preferred embodiment of the invention is one in which the relative bioavailability of the test composition is at least 1.25 relative to a control composition as described above. (That is, the AUC in the blood provided by the test composition is at least 1.25-fold the AUC provided by the control composition.) An even more preferred embodiment of the invention is one in which the relative bioavailability of the test composition is at least 2, more preferably at least 3 relative to a control composition of the drug but with no polymer present, as described above. The determination of AUCs is a well-known procedure and is described, for example, in Welling, "Pharmacokinetics Processes and Mathematics," ACS Monograph 185 (1986).

Often the enhancement in drug concentration or relative bioavailability that is observed increases as the drug:polymer ratio decreases from a value of about 1 (50 wt % drug) to a value of about 0.11 (10 wt % drug). The drug:polymer ratio that yields optimum results varies from drug to drug and is best determined in in vitro dissolution tests and/or in vivo bioavailability tests. However, the amount of polymer that can be used in a dosage form is often limited by the total mass requirements of the dosage form. For example, when oral dosing to a human is desired, at low drug-to-polymer ratios the total mass of drug and polymer may be unacceptably large for delivery of the desired dose in a single tablet or capsule. Thus, it is often necessary to use drug-to-polymer ratios that are less than optimum in specific dosage forms to provide a sufficient drug dose in a dosage form that is small enough to be easily delivered to a use environment.

Improved Chemical Stability

With respect to dispersions comprising an acid-sensitive drug and a neutralized acidic polymer, the resulting compositions provide improved chemical stability of the drug. That is, the acid-sensitive drug, when dispersed in a neutralized acidic polymer, degrades less over time under controlled storage conditions than when dispersed in the unneutralized acidic polymer.

In general, drug degradation may be measured using any conventional method for measuring the purity or potency of drug in a pharmaceutical composition. For example, the amount of active drug present in a dispersion may be initially measured using high-performance liquid chromatography (HPLC) or other analytical techniques well known in the art. Alternatively, the amount of drug initially present may be calculated from the amount of drug present in the dispersion formulation. The potency of the dispersion is then measured after storage at controlled temperature and humidity conditions for an appropriate period of time. A decrease in potency indicates that a chemical reaction has occurred, leading to a decrease in the amount of active drug present in the dispersion, and is an indication of poor chemical stability.

An alternative method used to evaluate chemical stability is to analyze the rate of increase in the amount of drug degradant(s) in the dispersion, which would indicate reaction of the drug. An HPLC or other analytical technique may be used to determine the concentration of drug degradant(s) in a dispersion. The amount of the degradant(s) is measured before and after storage under controlled storage conditions. The amount of increase in the drug degradant(s) may be used to determine the amount of decrease in percent "purity of the drug." The "percent drug purity" is defined as 100 times the total amount of drug present divided by the total amount of drug initially present. Thus, percent drug purity may be calculated by the formula $$\text{wt \% drug purity} = \left(\frac{\text{total amt. of drug present}}{\text{total amt. of drug init. present}}\right) * 100$$

When the drug purity is calculated from the total amount of impurities, "percent drug purity" may be calculated by assuming that the "total amount of drug initially present," given in wt %, is equal to 100 wt % minus the wt % of total initial impurities, and that "total amount of drug present" is equal to 100 wt % minus the wt % of total impurities after storage, that is, at some later time. This method is equivalent to calculating "percent drug purity" by the formula:

$$\text{wt \% drug purity} = \left[1 - \left(\frac{\text{Total amt. of Impurities present}}{\text{total amt. of drug init. present}}\right)\right] * 100$$

The rate at which drug degradation occurs is generally dependent on the storage conditions. The drug, when formulated as a composition of the present invention, should be stable at ambient temperature and humidity conditions (e.g., relative humidities of 20% to 60%) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final drug percent purity (either determined by measuring the decrease in drug present or an increase in the amount of drug degradants present) from the initial percent purity. For example, for a dispersion initially containing 100 mg drug, and no measurable impurities it would have an initial percent purity of 100 wt %. If, after storage, the amount of drug in the dispersion decreases to 95 mg, the final percent purity would be 95 wt % and the "degree of degradation" is 5 wt % (100 wt %-95 wt %). Alternatively, if 100 mg of drug substance were found to initially have 1 mg of impurities present, it would have an initial "percent purity" of 99 wt %. If, after storage, the total impurities present had increased to 6 wt %, the final percent purity would be 94 wt % and the "degree of degradation" would be 5 wt % (99 wt %-94 wt %).

Alternatively, "degree of degradation" can be determined by subtracting the amount of one or more specific drug degradants initially present from the amount of that specific degradant present after storage. Such a measure is useful where there are several drug degradants, of which only one (or a few) is of concern. The degree of degradation may be calculated on the basis of only those degradants that are of concern, rather than all of the degradants. For example, if a drug initially contained a specific degradant at a concentration of 1 wt % and after storage the concentration of that degradant was 6 wt %, the degree of degradation would be 5 wt % (6 wt %-1 wt %).

The dispersions of the present invention exhibit improved chemical stability relative to a control composition comprised of an equivalent quantity of acid-sensitive drug dispersed in the unneutralized form of the acidic polymer. The "unneutralized form" of the acidic polymer means that the degree of neutralization is less than 0.001. For example, where the dispersion of the present invention utilizes the sodium salt of hydroxy propyl methyl cellulose acetate succinate as the neutralized form of the acidic dispersion polymer, the control composition is comprised of an equivalent amount of drug dispersed in hydroxypropyl methyl cellulose acetate succinate in which essentially none of the succinate groups are neutralized.

A relative degree of improvement in chemical stability may be determined by taking the ratio of the degree of degradation of the drug in a control dispersion and the degree of degradation of the drug in a test dispersion of the present invention under the same storage conditions for the same storage time period. The test dispersion is simply the dispersion of acid-sensitive drug, neutralized form of the acidic polymer, and optional additional excipients of the present invention. The control dispersion is the same as the test dispersion with the exception that the acidic polymer in the unneutralized form replaces the neutralized acidic polymer of the test dispersion. For example, where the degree of degradation of a drug in a test dispersion comprised of a neutralized acidic dispersion polymer is 1 wt %, and the degree of degradation of the control composition is 50 wt %, the relative degree of improvement is 50 wt %/1 wt %, or 50. For dispersions of acid-sensitive drugs and neutralized acidic polymers of the present invention, the relative degree of improvement is at least 1.25. When the drug is particularly acid-sensitive, larger relative degrees of improvement may be necessary in order for the chemical stability of the dispersion to be pharmaceutically acceptable. In such cases, the invention provides greater chemical stability when the relative degree of improvement is at least about 2, preferably at least about 5, and even more preferably at least 10. In fact, some dispersions may achieve a relative degree of improvement greater than 100.

The particular storage conditions and time of storage may be chosen as convenient depending on the degree of acid-sensitivity of the drug, the particular acidic polymer used in the control dispersion, and the ratio of drug to polymer in the dispersion. Where the drug is particularly acid-sensitive, or where the dispersion has a low ratio of drug to polymer, then shorter storage time periods may be used. Where the rate of drug degradation is linear, the relative degree of improvement will be independent of the storage time. However, where the rate of drug degradation is non-linear under controlled storage conditions, the stability test used to compare the test dispersion with the control dispersion is preferably chosen such that the degree of degradation is sufficiently large that it may be accurately measured. Typically, the time period is chosen so as to observe a degree of degradation of at least 0.1 wt % to 0.2 wt %. However, the time period is not so long that the ratio of drug to polymer changes substantially. Typically, the time period is such that the observed degree of degradation for the test composition is less than 50 wt % and preferably less than 20 wt %. When the rate of drug degradation in the control composition is relatively slow, the test is preferably conducted over a long enough period of time under controlled storage conditions to allow a meaningful comparison of the stability of the test dispersion with the control dispersion.

A stability test which may be used to test whether a dispersion meets the chemical stability criteria described above is storage of the test dispersion and the control dispersion for six months at 40° C. and 75% RH. A relative degree of improvement may become apparent within a shorter time, such as three to five days, and shorter storage times may be used for some acid-sensitive drugs. When comparing dispersions under storage conditions which approximate ambient conditions, e.g., 25° C. and 60% RH, the storage period may need to be from several months up to two years.

In addition, it is preferred that the dispersions comprising acid-sensitive drug and neutralized acidic polymer(s) result in drug stability such that the acid-sensitive drug has a degree of degradation of less than about 2 wt %, more preferably less than about 0.5 wt %, and most preferably less than about 0.1 wt % when stored at 40° C. and 75% RH for six months, or less than about 2 wt %, more preferably less than about 0.5 wt %, and more preferably less than about 0.1 wt %, when stored at 30° C. and 60% RH for one year, or less than about 2 wt %, more preferably less than about 0.5 wt %, and more preferably less than about 0.1 wt %, when stored at ambient conditions for two years. Nevertheless, the compositions of the present invention may have a degree of degradation that is much greater than the preferred values, so long as the dispersion achieves the degree of improvement relative to a control composition as described above.

Neutralization Methods

The acidic polymers for use with the compositions of the present invention may be neutralized by any conventional method known in the art which results in the desired degree of neutralization. In general, the acidic polymer is neutralized through the addition of a sufficient amount of base to a solution or composition containing the polymer. The polymer may be neutralized prior to formation of the dispersion. For example, a base may be added to a solution of the acidic polymer resulting in neutralization of the polymer's acidic functional groups. Alternatively, the acidic polymer may be neutralized during formation of the dispersion, or may be neutralized following formation of the dispersion.

A wide range of bases may be used to neutralize the acidic polymer. The term "base" is used broadly to include not only strong bases such as sodium hydroxide, but also weak bases and buffers that are capable of achieving the desired degree of neutralization. Examples of bases include hydroxides, such as sodium hydroxide, calcium hydroxide, ammonium hydroxide, choline hydroxide; bicarbonates, such as sodium bicarbonate, potassium bicarbonate, and ammonium bicarbonate; carbonates, such as ammonium carbonate, and sodium carbonate; amines, such as tris(hydroxymethyl) amino methane, ethanolamine, diethanolamine, N-methyl glucamine, glucosamine, ethylenediamine, N,N'-dibenzyl-ethylenediamine, N-benzyl-2-phenethylamine, cyclohexylamine, cyclopentylamine, diethylamine, isopropylamine, diisopropylamine, dodecylamine, and triethylamine; proteins, such as gelatin; amino acids such as lysine, arginine, guanine, glycine, and adenine; polymeric amines, such as poly amino methacrylates, such as Eudragit E; conjugate bases of various acids, such as sodium acetate, sodium benzoate, ammonium acetate, disodium phosphate, trisodium phosphate, calcium hydrogen phosphate, sodium phenolate, sodium sulfate, ammonium chloride, and ammonium sulfate; salts of EDTA, such as tetra sodium EDTA; and salts of various acidic polymers such as sodium starch glycolate, sodium carboxymethyl cellulose and sodium polyacrylic acid. The use of the bicarbonates is in some cases preferred, as these generate carbon dioxide during the neutralization process, which can be removed easily following neutralization.

When the drug itself is basic the drug may constitute all or a portion of the base used to neutralize the acidic dispersion polymer. Thus, when the drug is the salt of an organic acid or an amine in its free base form, combination of the drug and the acidic polymer in a dispersion-formation process such as spray-drying, melt congealing, screw extrusion or the like may result in a composition of the invention. This is particularly true when the number of equivalents of base added in the form of the drug is equal to half or more of the number equivalents of and present as part of the polymer. Additional base that is not the drug may optionally be added.

As described previously, dispersions that contain significant quantities of a divalent cationic or multivalent cationic species such as $Ca^{2+}$, $Mg^{2+}$, or a diamine such as ethylene diamine are particularly desirable as they may ionically crosslink the dispersion polymer. This may conveniently be accomplished by adding such species in their basic form. Thus, exemplary bases containing a dicationic species include: calcium hydroxide, calcium acetate, magnesium hydroxide, magnesium stearate, aluminum hydroxide, ethylene diamine, polyamino methyacrylate, or any other pharmaceutically acceptable compound that may form a dicationic or polycationic species in the dispersion.

In one neutralization method, the polymer is neutralized prior to formation of the dispersion. The acidic polymer is first dissolved in a suitable solvent prior to addition of the base. Suitable solvents include water; ketones, such as acetone; alcohols, such as methanol, ethanol, isopropanol; and other solvents such as tetrahydrofuran, benzene, and dichloromethane. Mixtures of solvents, including mixtures of water and one or more organic solvents, may also be used. In particular, when organic solvents are used, addition of at least a small amount of water is often preferred to facilitate the neutralization process and to minimize excessively high or low pH values. The solvent may be selected such that it is a solvent for the neutralized acidic polymer but not necessarily a solvent for the acidic polymer prior to neutralization. This may facilitate isolation of the neutralized acidic polymer. Thus, prior to adding the base, the acidic polymer is not completely dissolved in the solvent. As the base is added, the neutralized acidic polymer dissolves.

For example, the acidic polymer HPMCAS may be neutralized by addition of a base to an aqueous solution containing HPMCAS. HPMCAS has a $pK_a$ of about 5. One procedure for neutralizing HPMCAS is to suspend the HPMCAS in distilled water. A base, such as sodium bicarbonate can then be added to this solution. As the base is added, the succinate groups on HPMCAS are neutralized, forming the sodium salt form of HPMCAS and at the same time the pH of the solution increases. When the pH of the solution reaches about 5, the $pK_a$ of the acidic moeities (succinate groups) of the polymer, the degree of neutralization, α, is 0.5. More base may be added, increasing the pH of the solution and increasing the extent of neutralization. Care must be taken, however, not to increase the pH too high, as at high pH (greater than about 8), the excess base can lead to degradation of the polymer. In the case of HPMCAS, such degradation can take the form of hydrolysis of ester-linked groups such as acetate or succinate or even cleavage of the cellulosic backbone of the polymer.

Following neutralization, the neutralized acidic polymer may be isolated and purified using methods known in the art. Examples of suitable methods include precipitation using a non-solvent, evaporation, rotoevaporation, spray-drying, and lyophylization. The neutralized acidic polymer can then be used to form the dispersion with the drug using the methods described below.

In another method, the neutralized acidic polymer is not isolated from the solvent, but instead, the drug is added to the polymer/solvent solution and the dispersion formed directly from this mixture. Examples of processes for forming the dispersion from such a solution are described below in connection with the discussion regarding formation of dispersions.

Another method for neutralizing the polymer during formation of the dispersion is to use a basic form of a drug which is capable of existing in a less basic form (for example where the drug has two basic substituents) or a non-basic form, such as a neutral or acidic form. The basic drug itself may be used to neutralize the acidic polymer, resulting in a dispersion of neutralized acidic polymer and drug. The drug in the dispersion may be partially or completely converted to its less basic or non-basic form.

Another method for neutralizing an acidic dispersion polymer is to neutralize the polymer after the dispersion has been formed. In this method, a base is blended with the dispersion of the acid-sensitive drug and acidic polymer. Exemplary bases that may be used to neutralize the acidic polymer include any of those listed above for neutralization of a polymer in solution but include, in particular, salts of acidic polymers such as sodium starch glycolate, cross carmellose sodium, and sodium carboxymethyl cellulose; amine functionalized polymers such as aminomethacryrates, amino acrylates, chitin, and proteins; inorganic bases such as tribasic calcium phosphate, calcium carbonate, disodium hydrogen phosphate and aluminum hydroxide; salts of acidic compounds such as magnesium stearate, sodium acetate, and potassium lactate; and amines such as meglumine and mono-, di- and tri-ethanolamine. Many of these bases, such as phosphate, carbonate and carboxylate salts, may be added in excess and as such may act as buffers, maintaining a relatively neutral pH (e.g., pH between about 5 and 9) in the composition. The amount of base to be blended with the dispersion should generally be in the range from about 0.1 to about 2.0 equivalents of base per equivalent of the acidic polymer moieties.

The amount of base to be blended with the dispersion may be determined by various techniques. For example, various dispersions of drug, acidic polymer, and base may be made that have varying levels of base equivalents per acidic polymer equivalent. An improvement in chemical stability during storage is an indication that sufficient base has been added. Alternatively, the polymer and drug may be dissolved or slurried in water and the pH monitored as base is added. The amount of base per amount of drug and polymer to achieve the desired pH may be noted. Generally, adding sufficient base to substantially increase the pH may be sufficient. The amount of base required to raise the pH to a value near 6 to 8 is often preferred.

The base and dispersion may be blended together to create a physical mixture using any conventional method known in the art. Thus, the base and dispersion may be blended together using wet- or dry-granulation. A high degree of blending or mixing is generally preferred in order to achieve maximum neutralization of the acidic polymer using this method. In general, the neutralization is facilitated by the presence of solvent, particularly water. For example, simple storage of the blended composition as a bulk material or in the form of a dosage form such as a tablet, granule or capsule under humid conditions for a period of a few hours to 30 days can result in sufficient neutralization of the acidic polymer dispersion. Likewise, the neutralization process may be facilitated by wet granulation processes in which the blend is relatively wet during at least a portion of the processing time.

Neutralization may be quantified by numerous methods, including storage and measurement of reduced drug degradation rates, spectroscopic analysis, potentiometric analysis, and thermal methods such as differential scanning calorimetry (DSC). Using DSC, for example, conversion of an acidic cellulosic polymer such as HPMCAS to the sodium or calcium salt form will lead to a measurable increase in the glass transition temperature of the polymer alone or drug/polymer dispersion. In the case of adding calcium the glass transition may be completely absent from the DSC data.

In addition, when dispersions are made by thermal processes such as a melt-congeal process, or an extrusion process, using, for example, a twin-screw extruder, that may form a dispersion by a combination of thermal and mechanical means, then the basic excipient may be blended with the drug and acidic polymer and the blend then fed to the melt-congeal or extrusion process apparatus. Such processes may also optionally include small amounts of solvent. Neutralization may occur completely or in part during processing as the heat, mechanical shear and solvent, if present, facilitate the neutralization process.

Preparation of Dispersions

In a preferred aspect of the invention, the mixture of drug and neutralized acidic polymer is a solid dispersion. While the drug in its pure state may be crystalline or amorphous, at least a major portion of the drug in the dispersion is amorphous. By "amorphous" is meant simply that the drug is in a non-crystalline state. As used herein, the term "a major portion" of the drug means that at least 60% of the drug in the dispersion is in the amorphous form, rather than the crystalline form. In general, drug is more reactive in its amorphous state relative to its crystalline state and so the need to neutralize the dispersion polymer to prevent degradation of acid-sensitive drug increases as the fraction of drug in the amorphous state increases. It has also been found that the aqueous concentration of the drug in a use environment tends to improve as the amount of amorphous drug present in the dispersion increases. Preferably, the drug in the dispersion is "substantially amorphous." As used herein, "substantially amorphous" means that the amount of the drug in amorphous form is at least 75%. More preferably, the drug in the dispersion is "almost completely amorphous" meaning that the amount of drug in the amorphous form is at least 90%. Amounts of crystalline drug may be measured by powder X-ray diffraction, Scanning Electron Microscope (SEM) analysis, differential scanning calorimetry (DSC), or any other standard quantitative measurement.

The amorphous drug can exist as a pure phase, as a solid solution of drug homogeneously distributed throughout the polymer or any combination of these states or those states that lie intermediate between them. To maximize the concentration enhancement provided by the dispersion, the dispersion is preferably substantially homogeneous so that the amorphous drug is dispersed as homogeneously as possible throughout the polymer. As used herein, "substantially homogeneous" means that the drug present in relatively pure amorphous domains within the solid dispersion is relatively small, and is less than 20%, and preferably less than 10%, of the total amount of drug. While the dispersion may have some drug-rich domains, it is preferred that the dispersion itself have a single glass transition temperature ($T_g$) which demonstrates that the dispersion is substantially homogeneous. This contrasts with a simple physical mixture of pure amorphous drug particles and pure amorphous polymer particles which generally display two distinct $T_g$s, one that of the drug and one that of the polymer. $T_g$ as used herein is the characteristic temperature where a glassy material, upon gradual heating, undergoes a relatively rapid (e.g., 10 to 100 seconds) physical change from a glass state to a rubber state. Dispersions of the present invention that are substantially homogeneous generally are more physically stable and have improved concentration-enhancing properties and, in turn, improved bioavailability, relative to nonhomogeneous dispersions.

Dispersions of the drug and neutralized acidic polymer may be made according to any known process which results in at least a major portion of the drug in the dispersion being in the amorphous state. Such processes include mechanical, thermal and solvent processes. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923, U.S. Pat. No. 5,939,099 and U.S. Pat. No. 4,801,460 which describe formation of dispersions via extrusion processes; U.S. Pat. No. 5,340,591 and U.S. Pat. No. 4,673,564 which describe forming dispersions by milling processes; and U.S. Pat. No. 5,684,040, U.S. Pat. No. 4,894,235 and U.S. Pat. No. 5,707,646 which describe the formation of dispersions via melt/congeal processes, the disclosures of which are incorporated by reference.

In particular, when either the neutralized acidic polymer or the drug has a relatively low melting point, typically less than about 200° C. and preferably less than about 160° C., extrusion or melt-congeal processes that provide heat and/or mechanical energy are often suitable for forming almost completely amorphous dispersions. Often, when the drug has significant solubility in the dispersion material, such methods may also make substantially homogeneous dispersions. For example, 10 wt % drug and 90 wt % of a suitable polymer may be dry blended, with or without the addition of water, and the blend fed to a twin-screw extrusion device. The processing temperature may vary from about 50° C. up to about 200° C. depending on the melting point of the drug and polymer, which is a function of the polymer grade chosen and the amount of water, if any, added. Generally, the higher the melting point of the drug and polymer, the higher the processing temperature. Generally, the lowest processing temperature that produces a satisfactory dispersion (almost completely amorphous and substantially homogeneous) is chosen.

A preferred method for forming dispersions is "solvent processing," which consists of dissolution of the drug and one or more neutralized acidic polymers in a common solvent. The term "solvent" is used broadly and includes mixtures of solvents. "Common" here means that the solvent, which can be a mixture of compounds, will simultaneously dissolve the drug and the polymer(s). For dispersions formed from neutralized acidic polymers that have not been isolated from the polymer/solvent solution to which base has been added, the acid-sensitive drug may be added to the solution containing the solvent and neutralized acidic polymer, and the dispersion then may be formed directly from the resulting solution.

After both the drug and polymer(s) have been dissolved, the solvent is rapidly removed by evaporation or by mixing with a non-solvent. Exemplary processes are spray-drying, spray-coating (pan-coating, fluidized bed coating, etc.), vacuum evaporation, and precipitation by rapid mixing of the polymer and drug solution with $CO_2$, water, or some other non-solvent. Preferably, removal of the solvent results in a solid dispersion which is substantially homogeneous. In substantially homogeneous dispersions, the drug is dispersed as homogeneously as possible throughout the polymer and can be thought of as a solid solution of drug dispersed in the polymer(s). When the resulting dispersion constitutes a solid solution of drug in polymer, the dispersion may be thermodynamically stable, meaning that the concentration of drug in the polymer is at or below its equilibrium value, or it may be considered a supersaturated solid solution where the drug concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be any organic compound in which the drug and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable. As described previously, addition of at least a few percent water is often preferred.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and polymer-rich phases. As above, to get large enhancements in concentration and bioavailability it is often necessary to obtain as homogeneous of a dispersion as possible. Solidification times should be less than 100 seconds, preferably less than a few seconds, and more preferably less than 1 second. In general, to achieve this rapid solidification of the drug/polymer solution, it is preferred that the size of droplets formed during the spray-drying process are less than about 100 µm in diameter. The resultant solid particles thus formed are generally less than about 100 µm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of drug molecules in the dispersion, thereby improving its stability. Generally, the solvent content of the dispersion as it leaves the spray-drying chamber should be less than 10 wt % and preferably less than 2 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

The amount of polymer relative to the amount of drug present in the dispersions of the present invention depends on the drug and polymer and may vary widely from a drug-to-polymer weight ratio of from 0.01 to about 4 (e.g., 1 wt % drug to 80 wt % drug). However, in most cases it is preferred that the drug-to-polymer ratio is greater than about 0.05 (4.8 wt % drug) and less than about 2.5 (71 wt % drug).

In addition to the drug and polymer(s), the dispersions of the present invention may include optional additional ingredients. For example, the dispersions may contain other neutral polymers or other dispersion forming materials. Nevertheless, the drug and neutralized acidic polymer comprise at least 50 wt % of the dispersion.

When the composition comprises a dispersion of an acid-sensitive drug and a neutralized acidic polymer, a preferred optional additional ingredient is a buffer. Although the combination of the acidic polymer and base may itself constitute a buffer, additional excipients may further serve to maintain the effective pH of the compositions of the invention closer to the optimum value for stability of the drug of interest. This is particularly important when the composition may come into contact with additional sources of acid or base during processing or storage of the composition. In particular, certain acid-sensitive drugs may generate acidic or basic species upon storage and therefore the presence of a buffer that may neutralize such species may be preferred as it leads to improved stability. Addition of a buffer to the dispersion will also buffer any acidic or basic degradants that form, inhibiting further degradation. For example, a buffer such as disodium hydrogen phosphate may be added to keep the pH of the composition between the second and third $pK_a$s of phosphate. This is particularly preferred when a strong base such as potassium hydroxide is used to neutralize an acidic polymer. In such cases, it may be difficult to ensure that the degree of neutralization, at, is equal to 1.0 without adding more than 1.0 equivalent of base per equivalent of acid (polymeric). Without the buffer, excess base could lead to an undesirably high pH, which could lead to degradation of the drug, degradation of the dispersion polymer, or other undesirable effects.

Exemplary buffers that may be used in the dispersions of the present invention include sodium acetate, ammonium acetate, sodium carbonate and various salts of phosphate including disodium hydrogen phosphate and trisodium phosphate. Such buffers may comprise from 5 to 30 wt % of the dispersion. Buffers suitable for use in the dispersions of the present invention are preferably those that will maintain the pH of the dispersion at a value of 5 or more and preferably 6 or more. In cases where the drug is base sensitive, it is also preferred that the buffer be chosen to maintain the effective pH of the dispersion below 9 and more preferably below 8. Buffers are particularly preferred for dispersions of neutralized polymers and drugs that have a high degree of acid sensitivity. The buffers may reduce the risk of drug degradation due to the presence of acidic species in either the dispersion or elsewhere in the composition.

Mixtures of Dispersions and Concentration-Enhancing Polymer

An optional additional ingredient is a second concentration-enhancing polymer that is not present in the dispersion. The compositions of this aspect of the present invention are generally physical combinations comprising the dispersion and the second concentration-enhancing polymer. "Combination" as used herein means that the dispersion and second concentration-enhancing polymer may be in physical contact with each other or in close proximity but without the necessity of being in the form of a molecular dispersion. For example, the solid composition may be in the form of a multi-layer tablet, as known in the art, wherein one or more layers comprises the dispersion and one or more different layers comprises the second concentration-enhancing polymer. Yet another example may constitute a coated tablet wherein either the dispersion or the second concentration-enhancing polymer or both may be present in the tablet core and the coating may comprise the second concentration-enhancing polymer or both. Alternatively, the combination can be in the form of a simple dry physical mixture wherein both the dispersion and the second concentration-enhancing polymer are mixed in particulate form and wherein the particles of each, regardless of size, retain the same individual physical properties that they exhibit in bulk. Any conventional method used to mix the second concentration-enhancing polymer and dispersion together such as physical mixing and dry or wet granulation, which does not substantially convert the dispersion and second concentration-enhancing polymer to another molecular dispersion, may be used.

Alternatively, the dispersion and second concentration-enhancing polymer may be co-administered, meaning that the dispersion may be administered separately from, but within the same general time frame as, the second concentration-enhancing polymer. Thus, a dispersion may, for example, be administered in its own dosage form which is taken at approximately the same time as the second concentration-enhancing polymer which is in a separate dosage form. If administered separately, it is generally preferred to administer both the dispersion and the second concentration-enhancing polymer within 60 minutes of each other, so that the two are present together in the use environment. When not administered simultaneously, the second concentration-enhancing polymer is preferably administered prior to the dispersion.

The second concentration-enhancing polymer may be any concentration-enhancing polymer, such as those described above in connection with the neutralized acidic polymer. As described above, the inventors have found that ionizable, cellulosic polymers, particularly those that are cellulosic acidic enteric polymers, provide superior enhancement in aqueous concentration of the drug in a use environment relative to other polymers, and are therefore preferred in the absence of their reactivity with the drug. Many of these ionizable, cellulosic polymers have acidic functional groups and therefore are inappropriate for use as a dispersion polymer without first being neutralized. However, the concentration-enhancing advantage provided by such ionizable concentration-enhancing polymers may be achieved by simply combining the ionizable polymer with a pre-formed dispersion of the acid-sensitive drug and a neutralized acidic polymer in a fashion that does alter the neutral characteristic of the pre-formed dispersion.

Alternatively, the second concentration-enhancing polymer may be a neutral concentration-enhancing polymer. A preferred class of neutral concentration-enhancing polymers consists of neutral cellulosic polymers which contain non-ionizable substituents which are either ether-linked or ester-linked. A preferred class of neutral cellulosic polymers are those with at least one ester- and/or ether-linked substituent in which the polymer has a degree of substitution of at least 0.1 for each substituent. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate. However, when ester-linked non-ionizable groups are included, the polymer may need to include a sufficient amount of a hydrophilic substituent so that the polymer has at least some water solubility at any physiologically relevant pH of from 1 to 8.

Exemplary neutral (i.e., non-ionizable) cellulosic polymers that may be used include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

Another class of neutral polymers is non-cellulosic neutral polymers. Exemplary polymers include: vinyl polymers and copolymers having substituents of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers.

A preferred class of neutral non-cellulosic polymers are comprised of vinyl copolymers of a hydrophilic, hydroxyl-containing repeat unit and a hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

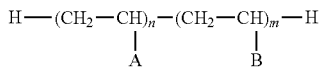

where A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units, "A," may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus, exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent, "B," may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—CH$_2$—CH$_2$—CH$_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100 * \left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3.

A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer, polyvinylalcohol is not amphiphilic, and is almost entirely water insoluble. Preferred vinylacetate/vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

While specific polymers are discussed as being suitable for use in the compositions of the present invention, blends of such polymers may also be suitable. Thus the term "polymer" is intended to include blends of polymers in addition to a single species of polymer.

Excipients and Dosage Forms

Although the key ingredients in the compositions of the present invention are simply the drug and concentration-enhancing polymer(s), the inclusion of other excipients in the composition may be useful. These excipients may be utilized with the drug and polymer composition in order to formulate the composition into tablets, capsules, suppositories, suspensions, powders for suspension, creams, transdermal patches, depots, and the like. The dispersion of drug and polymer can be added to other dosage form ingredients in essentially any manner that does not substantially alter the drug. The excipients may be either physically mixed with the dispersion and/or included within the dispersion. However, acidic excipients should not be added to the dispersion unless either neutralized prior to addition or they are added in an amount that may be neutralized by any base or buffer present in the composition.

One very useful class of excipients is surfactants. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic). Of course, where the drug is acid-sensitive, care should be taken when acidic pH modifiers are added to the dispersion to avoid rendering the dispersion acidic, as discussed above.

Other conventional formulation excipients may be employed in the compositions of this invention, including those excipients well-known in the art (e.g., as described in *Remington's Pharmaceutical Sciences* ($16^{th}$ ed. 1980). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suppositories, suspensions, powders for suspension, creams, transdermal patches, depots, and the like.

Examples of other matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch glycolate, sodium carboxymethyl cellulose, calcium carboxymethyl cellulose, croscarmellose sodium, crospovidone (polyvinylpolypyrrolidone), methyl cellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenatetd vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

The compositions of the present invention may be delivered by a wide variety of routes, including, but not limited to, oral, nasal, rectal, vaginal, subcutaneous, intravenous and pulmonary. Generally, the oral route is preferred.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

A preferred additive to such formulations is additional concentration-enhancing polymer which may act as a thickener or suspending agent as well as to enhance the concentration of drug in the environment of use and may also act to prevent or retard precipitation or crystallization of drug from solution. Such preferred additives are hydroxyethyl cellulose, hydroxypropyl cellulose, and hydroxypropyl methyl cellulose. In particular, the salts of carboxylic acid functional polymers such as cellulose acetate phthalate, hydroxypropyl methyl cellulose acetate succinate, and carboxymethyl cellulose are useful in this regard. Such polymers may be added in their salt forms or the salt form may be formed in situ during reconstitution by adding a base such as trisodium phosphate and the acid form of such polymers.

In some cases, the overall dosage form or particles, granules or beads that make up the dosage form may have superior performance if coated with an enteric polymer to prevent or retard dissolution until the dosage form leaves the stomach. Exemplary enteric coating materials include hydroxypropyl methyl cellulose acetate succinate, hydroxypropyl methyl cellulose phthalate, cellulose acetate phthalate, cellulose acetate trimellitate, carboxylic acid-functionalized polymethacrylates, and carboxylic acid-functionalized polyacrylates. When the drug is acid-sensitive, care should be taken to avoid acidification of the drug dispersion during coating or during storage. In some cases, it may be necessary to add an intervening layer of a non-acidic material to avoid direct contact between the enteric coating polymer and the acid-sensitive drug.

Compositions of this invention may be administered in a controlled release dosage form. In one such dosage form, the composition of the drug and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the dispersion of drug and polymer. The aqueous-swollen matrix gradually erodes, swells, disintegrates or dissolves in the environment of use, thereby controlling the release of the dispersion to the environment of use. Examples of such dosage forms are disclosed more fully in commonly assigned pending U.S. patent application Ser. No. 09/495,059 filed Jan. 31, 2000 which claimed the benefit of priority of provisional patent application Ser. No. 60/119,400 filed Feb. 10, 1999, the relevant disclosure of which is herein incorporated by reference.

Alternatively, the compositions of the present invention may be administered by or incorporated into a non-erodible matrix device.

Alternatively, the compositions of the invention may be delivered using a coated osmotic controlled release dosage form. This dosage form has two components: (a) the core which contains an osmotic agent and the composition of drug and neutralized acidic polymer; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port. Examples of such dosage forms are disclosed more fully in commonly assigned pending U.S. patent application Ser. No. 09/495,061 filed Jan. 31, 2000 which claimed the benefit of priority of provisional Patent Application Ser. No. 60/119,406 filed Feb. 10, 1999, the relevant disclosure of which is herein incorporated by reference.

Alternatively, the compositions may be delivered via a coated hydrogel controlled release form having at least two components: (a) a core comprising the composition of the drug and polymer of the present invention and a hydrogel, and (b) a coating through which the composition has passage when the dosage form is exposed to a use environment. Examples of such dosage forms are more fully disclosed in commonly assigned European Patent EP0378404, the relevant disclosure of which is herein incorporated by reference.

Alternatively, the drug mixture of the invention may be delivered via a coated hydrogel controlled release dosage form having at least three components: (a) a composition containing drug and neutralized acidic polymer, (b) a water-swellable composition wherein the water-swellable composition is in a separate region within a core formed by the drug-containing composition and the water-swellable composition, and (c) a coating around the core that is water-permeable, water-insoluble, and has at least one delivery port therethrough. In use, the core imbibes water through the coating, swelling the water-swellable composition and increasing the pressure within the core, and fluidizing the drug-containing composition. Because the coating remains intact, the dispersion-containing composition is extruded out of the delivery port into an environment of use. Examples of such dosage forms are more fully disclosed in commonly assigned pending patent application Ser. No. 09/745,095 filed Dec. 20, 2000, which claimed priority to Provisional Application Ser. No. 60/171,968 filed Dec. 23, 1999, the relevant disclosure of which is herein incorporated by reference.

Alternatively, the compositions may be administered as multiparticulates. Multiparticulates generally refer to dosage forms that comprise a multiplicity of particles that may range in size from about 10 µm to about 2 mm, more typically about 100 µm to 1 mm in diameter. Such multiparticulates may be packaged, for example, in a capsule such as a gelatin capsule or a capsule formed from an aqueous-soluble polymer such as HPMCAS, HPMC or starch or they may be dosed as a suspension or slurry in a liquid.

Such multiparticulates may be made by any known process, such as wet- and dry-granulation processes, extrusion/spheronization, roller-compaction, or by spray-coating seed cores. For example, in wet- and dry-granulation processes, the composition of drug and concentration-enhancing polymer is prepared as described above. This composition is then granulated to form multiparticulates of the desired size. Other excipients, such as a binder (e.g., microcrystalline cellulose), may be blended with the composition to aid in processing and forming the multiparticulates. In the case of wet granulation, a binder such as microcrystalline cellulose may be included in the granulation fluid to aid in forming a suitable multiparticulate.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

Compositions of the present invention may be used to treat any condition which is subject to treatment by administering a drug.

Other features and embodiments of the invention will become apparent from the following examples which are given for illustration of the invention rather than for limiting its intended scope.

EXAMPLES

Examples 1-3

These examples disclose dispersions of a drug and a neutralized acidic polymer. For Examples 1-3, a dispersion of the acid-sensitive drug quinoxaline-2-carboxylic acid[4(R)-carbamoyl-1(S)-3-fluorobenzyl)-2(S),7-dihydroxy-7-methyl-octyl]amide (Drug 1) and the neutralized acidic enteric polymer hydroxypropyl methyl cellulose acetate succinate (HPMCAS) was made by first preparing a solution containing drug, polymer and a base. For Example 1, the solution consisted of 1.25 wt % Drug 1, 0.513 wt % sodium acetate, and 3.75 wt % HPMCAS-HF (HF grade of HPMCAS from Shin Etsu, Tokyo, Japan) in methanol/water (9/1). For Example 2, the solution consisted of 1.25 wt % Drug 1, 0.32 wt % sodium bicarbonate, and 3.75 wt % HPMCAS-HF in methanol/water (9/1). For Example 3, the solution consisted of 1.25 wt % Drug 1, 1.42 wt % sodium borate, and 3.75 wt % HPMCAS-HF in methanol/water (9/1). For control C1, the solution consisted of 1.25 wt % Drug 1 and 3.75 wt % HPMCAS-HF, with no added base.

For Examples 1-3, and Control C1, the solutions were spray-dried by pumping the solution into a "mini" spray-dryer apparatus via a Cole Parmer 74900 series rate-controlling syringe pump at a rate of 1.3 mL/min. The drug/polymer solution was atomized through a Spraying Systems Co. two-fluid nozzle, Module No. SU1A using a heated stream of nitrogen (100° C.). The spray solution was sprayed into an 11-cm diameter stainless steel chamber. The resulting solid amorphous dispersions containing 25 wt % Drug 1 were collected on filter paper, dried under vacuum, and stored in a dessicator. Table 1 summarizes the spray-drying variables.

TABLE 1

| Ex. | Drug Mass (mg) | Excipient | Excipient Mass (mg) | Polymer | Polymer Mass (mg) | Solvent | Solvent Mass (g) |
|---|---|---|---|---|---|---|---|
| 1 | 125 | NaOAc | 51.4 | HPMCAS-HF | 375 | MeOH/water 9/1 | 10 |
| 2 | 125 | NaHCO$_3$ | 32 | HPMCAS-HF | 375 | MeOH/water 9/1 | 10 |
| 3 | 125 | NaBorate | 142 | HPMCAS-HF | 375 | MeOH/water 9/1 | 10 |
| C1 | 50 | none | 0 | HPMCAS-HF | 150 | MeOH | 4 |

Example 4

Stability of the acid-sensitive drug in the dispersions of Examples 1-3 was determined by measuring the drug purity before and after storage for Examples 1-3 and control C1. Dispersions were stored under elevated temperature and humidity conditions to increase the rate of chemical and physical changes occurring in the materials in order to simulate a longer storage interval in a typical storage environment. Drug purity was determined using HPLC. A Kromasil C$_4$ HPLC column was used with a mobile phase of 45 vol % of 0.2 vol % H$_3$PO$_4$, and 55 vol % acetonitrile. UV detection was measured at 245 nm. Drug 1 potency was the percent of the total HPLC peak area corresponding to the amount of drug originally present in the dispersion prior to storage. Results of potency analysis of dispersions of Drug 1 and neutralized HPMCAS after storage for five days at 40° C./75% RH are shown in Table 2.

TABLE 2

| Ex. | Aqueous-Soluble Polymer/Base | Drug 1 Conc. In the Dispersion (wt %) | Potency Day 5 at 40° C./75% RH (%) | Degree of Degradation at Day 5 | Relative Degree of Improvement |
|---|---|---|---|---|---|
| 1 | HPMCAS/NaOAc | 23 | 90.6 | 9.4 | 4.3 |
| 2 | HPMCAS/NaHCO$_3$ | 24 | 95.4 | 4.6 | 8.7 |
| 3 | HPMCAS/NaBorate | 20 | 92.7 | 7.3 | 5.5 |
| C1 | HPMCAS-HF | 25 | 60 | 40 | — |

Stabilities of the dispersions with neutralized acidic polymers were significantly improved in comparison to the stability of the dispersion with unneutralized HPMCAS. A degree of degradation for each dispersion was calculated by comparing the calculated amount of drug initially present in the dispersion with the drug potency measured at Day 5. The relative degree of improvement for each dispersion compared with the control C1 was 4.3 for Example 1, 8.7 for Example 2, and 5.5 for Example 3.

Examples 5-6

These examples disclose dispersions of Drug 1 and an acidic polymer with different degrees of neutralization. Amorphous solid dispersions of Drug 1 and HPMCAS were made by first mixing Drug 1 in a solvent together with HPMCAS-MF and sodium hydroxide to form a solution. For Example 5, the solution comprised 0.29 wt % Drug 1, 0.89 wt % HPMCAS-MF, 0.038 wt % NaOH, and 98.782 wt % water/acetonitrile (9/1). (MF grade of HPMCAS available from Shin Etsu, Tokyo, Japan) The percentage of acidic groups on the polymer that were neutralized was approximately 99%. For Example 6, the solution comprised 0.31 wt % Drug 1, 0.94 wt % HPMCAS-MF, 0.019 wt % NaOH, and 98.731 wt % water/acetonitrile (9/1). The percentage of acidic groups on the polymer that were neutralized was approximately 50%. For Control C2, the solution comprised 0.33 wt % Drug 1 and 1.00 wt % HPMCAS-MF in 98.67 wt % water/acetonitrile (9/1). The solutions of Examples 5 and 6, and Control C2, were lyophilized to remove the solvent (samples were flash-frozen in liquid nitrogen, and the solvent was removed under vacuum from the solid state). After the solvent was removed, the resulting solid dispersions of Examples 5 and 6, and Control C2, contained 25 wt % Drug 1.

Example 7

In this example the chemical stability of the dispersions of Examples 5 and 6 and Control C2 was assessed. The dispersions were stored for 3.8 days at 40° C. and 75% relative humidity, then analyzed for Drug 1 potency by HPLC using the method described in Example 3. Results are shown in Table 3, as are the results for Control C2.

TABLE 3

| Ex. No. | Polymer | Drug 1 Conc. in the Dispersion (wt %) | Poten. Before Stor. (%) | Potency After 3.8 Days @ 40° C./75% RH | Degree of Degradation @3.8 Days | Relat. Degree of Improvement |
|---|---|---|---|---|---|---|
| 5 (99% neutralized) | HPMCAS-MF/Na+ | 25 | 98.18 | 96.08 | 2.10 | 20 |
| 6 (50% neutralized) | HPMCAS-MF/Na+ | 25 | 98.17 | 89.34 | 8.83 | 5 |

TABLE 3-continued

| Ex. No. | Polymer | Drug 1 Conc. in the Dispersion (wt %) | Poten. Before Stor. (%) | Potency After 3.8 Days @ 40° C./ 75% RH | Degree of Degradation @3.8 Days | Relat. Degree of Improvement |
|---|---|---|---|---|---|---|
| C2 | HPMCAS-MF | 25 | 97.42 | 55.12 | 42.30 | — |

As the data show, the dispersions of Examples 5 and 6 formed with neutralized HPMCAS are chemically stable when compared with Control C2, showing a relative degree of improvement of 20 for Example 5, and 5 for Example 6. The improvement is greater for Example 5, which has a higher percentage of acidic groups neutralized on the polymer.

Example 8

This example discloses a dispersion of a second drug, 5-chloro-1H-indole-2-carboxylic acid[(1S)-benzyl-3-((3R,4S)-dihydroxypyrrolidin-1-yl)-(2R)-hydroxy-3-oxypropyl] amide ("Drug 2"), and a neutralized acidic polymer. A slurry containing 1.5 wt % cellulose acetate phthalate (CAP) (available from Eastman Chemical Co., Kingsport, Tenn.) in water was stirred and $NaHCO_3$ was added until the polymer dissolved and the pH was 7.3 (approximately 100% of the polymer acidic groups neutralized). The water was removed from the neutralized polymer by heating the solution under vacuum. Amorphous solid dispersions of Drug 2 and neutralized CAP were made by first mixing Drug 2 in a solvent together with neutralized CAP to form a solution. For Example 8, the solution comprised 0.8 wt % Drug 2 and 2.4 wt % neutralized CAP in 96.7 wt % acetone/water (7/1). For Control C3, the solution comprised 0.96 wt % Crug 2 and 2.88 wt % CAP in 96.16 wt % acetone. Each of these solutions was spray-dried by pumping the solution into a "mini" spray-dryer apparatus as described for Examples 1-3. After drying, the dispersions of Example 8 and Control C3 contained 25 wt % Drug 2.

Example 9

The dispersion of Example 8 and Control C3 were tested to show that the neutralized dispersion provided concentration-enhancement of the drug in solution. For this test, 14.4 mg of the dispersion was added to a microcentrifuge tube for a total Drug 2 concentration of approximately 2000 µg/mL if all of the drug were to dissolve completely. The tube was placed in a 37° C. temperature-controlled chamber, and 1.8 mL PBS as pH 6.5 and 290 mOsm/kg was added. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, and 1200 minutes.

For comparison, a Control C4 consisting of 3.6 mg of crystalline Drug 2 was added to PBS for a total concentration of 2000 µg/mL. The results are shown in Table 4.

TABLE 4

| Example | Time (min) | Drug 2 Concentration (µg/mL) | AUC (µg/mL) |
|---|---|---|---|
| 8 | 0 | 0 | 0 |
|   | 4 | 1405 | 2,800 |
|   | 10 | 1986 | 13,000 |
|   | 20 | 2069 | 33,300 |
|   | 40 | 2079 | 74,700 |
|   | 90 | 2087 | 178,900 |
|   | 1200 | 358 | 1,535,900 |
| C3 | 0 | 0 | 0 |
|   | 4 | 1939 | 3,900 |
|   | 10 | 1859 | 15,300 |
|   | 20 | 1880 | 34,000 |
|   | 40 | 1899 | 71,800 |
|   | 90 | 1875 | 166,100 |
|   | 1200 | 334 | 1,392,100 |
| C4 Crystalline Drug 2 | 0 | 0 | 0 |
|   | 4 | 131 | 300 |
|   | 10 | 114 | 1,000 |
|   | 20 | 124 | 2,200 |
|   | 40 | 107 | 4,500 |
|   | 90 | 126 | 10,300 |
|   | 1200 | 72 | 120,200 |

These data were used to determine the values of $C_{max90}$ and $AUC_{90}$. The results are shown in Table 5. As can be seen from the data, the dispersion of Drug 2 in neutralized polymer (Example 8) provided greater concentration-enhancement than a dispersion using acidic polymer without neutralization (C3). In addition, the $C_{max90}$ for the test composition (Example 8) was 16-fold that of the crystalline control (C4), and an $AUC_{90}$ was 17-fold that of the control.

TABLE 5

| Example | Drug 2 Concentration (µg/mL) | AUC (µg/mL) |
|---|---|---|
| 8 | 2087 | 178,900 |
| C3 | 1939 | 166,100 |
| C4 Crystalline Drug 2 | 131 | 10,300 |

Example 10

This example discloses a dispersion of Drug 2 and the neutralized acidic polymer hydroxypropylmethyl cellulose phthalate (HPMCP). For Example 10, the dispersion was made by first forming a solution consisting of 0.55 wt % Drug 2, 1.64 wt % HPMCP (HP-55 grade available from Shin Etsu, Tokyo, Japan), and 0.51 wt % lysine in 86.4 wt % methanol and 10.9 wt % water. The acidic groups on the HPMCP polymer were neutralized in situ by combining with the basic groups of lysine. The solution was spray-dried by pumping the solution into a "mini" spray-dryer apparatus via a Cole Parmer 74900 series rate-controlling syringe pump at a rate of 0.8 mL/min. The drug/polymer solution was atomized through a Spraying Systems Co. two-fluid nozzle, Module No. SU1A using a heated stream of nitrogen (100° C.). The spray solution was sprayed into an 11-cm diameter stainless steel chamber. The resulting solid amorphous dispersion was collected on filter paper, dried under vacuum, and stored in a dessicator. After drying, the dispersion of Example 10 contained 20 wt % Drug 2.

Example 11

The dispersion of Example 10 was tested to show that the neutralized dispersion provided concentration-enhancement of the drug in solution. For this test, 14.4 mg of the dispersion was added to a microcentrifuge tube for a total Drug 2 concentration of approximately 2000 µg/mL if all of the drug were to dissolve completely. The dissolution test was performed as described in Example 9. The results are shown in Table 6. Control C4 (consisting of 3.6 mg of crystalline Drug 2) is shown again for comparison.

TABLE 6

| Example | Time (min) | Drug 2 Concentration (µg/mL) | AUC (min * µg/mL) |
|---|---|---|---|
| 10 | 0 | 0 | 0 |
|  | 4 | 888 | 1,800 |
|  | 10 | 880 | 7,100 |
|  | 20 | 804 | 15,500 |
|  | 40 | 782 | 31,400 |
|  | 90 | 734 | 69,300 |
|  | 1200 | 165 | 568,200 |
| C4 | 0 | 0 | 0 |
| Crystalline | 4 | 131 | 300 |
| Drug 2 | 10 | 114 | 1,000 |
|  | 20 | 124 | 2,200 |
|  | 40 | 107 | 4,500 |
|  | 90 | 126 | 10,300 |
|  | 1200 | 72 | 120,200 |

These date were used to determine the values of $C_{max90}$ and $AUC_{90}$. The results are summarized in Table 7. The $C_{max90}$ for the test composition was 6.8-fold that of the crystalline control (C4), and an $AUC_{90}$ was 6.7-fold that of the control.

TABLE 7

| Example | $C_{max90}$ (µg/mL) | $AUC_{90}$ (min * µg/mL) |
|---|---|---|
| 10 | 888 | 69,300 |
| C4 crystalline Drug 2 | 131 | 10,300 |

Examples 12-14

This example demonstrated that the free-base form of the drug can be used to neutralize the acidic polymer. For Examples 12-14, dispersions were made of the free-base form of ziprazidone ("Drug 3A"), and different neutralized acidic polymers by first forming a solution of the drug and the polymer in a solvent. For Example 12, the solution consisted of 0.35 wt % Drug 3A, and 1.05 wt % of the acidic polymer carboxy methyl ethyl cellulose (CMEC) (available from Freund Industrial Co. Ltd, Tokyo Japan), in 43.36 wt % tetrahydrofuran and 55.24 wt % methanol. For Example 13, the solution consisted of 0.29 wt % Drug A, and 0.88 wt % CAP (acidic polymer), in 52.35 wt % tetrahydrofuran and 46.48 wt % methanol. For Example 14, the solution consisted of 0.29 wt % Drug 3A, and 0.88 wt % HPMCAS-HG (acidic polymer), in 52.35 wt % tetrahydrofuran and 46.48 wt % methanol. (The HG grade of HPMCAS is available for Shin Etsu, Tokyo, Japan.) The acidic groups on the polymers were neutralized in situ by combining with the basic groups of Drug 3A. The solutions were spray-dried by pumping each solution into a "mini" spray-dryer apparatus via a Cole Parmer 74900 series rate-controlling syringe pump at a rate of 1.0 mL/min. The drug/polymer solution was atomized through a Spraying Systems Co. two-fluid nozzle, Module No. SU1A using a heated stream of nitrogen (100° C.). The spray solution was sprayed into an 11-cm diameter stainless steel chamber. The resulting solid amorphous dispersion was collected on filter paper, dried under vacuum, and stored in a dessicator. After drying, the dispersions of Examples 12, 13, and 14 all contained 25 wt % Drug 3A. Controls C5, C6, and C7 consisted of dispersions of CMEC, CAP, and HPMCAS spray dried as described above, but with the hydrochloride salt of Drug 3 ("Drug 3B"). The drug in the hydrochloride salt form did not have the basic groups available to neutralize the acidic dispersion polymers. Control C8 consisted of crystalline Drug 3A alone.

Example 15

The dispersions of Examples 12-14 were tested to show that neutralized dispersions provided concentration-enhancement of the drug in solution. For these tests, 1.44 mg of each dispersion was added to a microcentrifuge tube containing PBS with 0.5 wt % sodium taurocholic acid and 1-palmitoyl-2-oleyl-sn-glycero-3-phosphocholine ("NaTC/POPC," with a 4/1 weight ratio), for a total Drug 3 concentration of approximately 200 µg/mL if all of the drug were to dissolve completely. For Controls C5, C6, and C7 (with Drug 3B), 1.57 mg of each dispersion was added to PBS containing 0.5 wt % NaTC/POPC to yield approximately 200 µg/mL of active Drug 3. Control C8 consisted of 0.36 mg of crystalline Drug 3A. The dissolution tests were performed as described in Example 9. The results are shown in Table 8.

TABLE 8

| Example | Time (min) | Drug 3 Concentration (µg/mL) | AUC (min * µg/mL) |
|---|---|---|---|
| 12 | 0 | 0 | 0 |
|  | 4 | 203 | 400 |
|  | 10 | 38 | 1,100 |
|  | 20 | 22 | 1,400 |
|  | 40 | 18 | 1,800 |
|  | 90 | 16 | 2,700 |
|  | 1200 | 14 | 19,300 |
| 13 | 0 | 0 | 0 |
|  | 4 | 88 | 200 |
|  | 10 | 83 | 700 |
|  | 20 | 31 | 1,300 |
|  | 40 | 14 | 1,700 |
|  | 90 | 14 | 2,400 |
|  | 1200 | 23 | 22,900 |
| 14 | 0 | 0 | 0 |
|  | 4 | 115 | 200 |
|  | 10 | 89 | 800 |
|  | 20 | 70 | 1,600 |
|  | 40 | 61 | 2,900 |
|  | 90 | 50 | 5,700 |
|  | 1200 | 23 | 46,200 |
| C5 | 0 | 0 | 0 |

TABLE 8-continued

| Example | Time (min) | Drug 3 Concentration (µg/mL) | AUC (min * µg/mL) |
|---|---|---|---|
| Drug 3B | 4 | 196 | 400 |
|  | 10 | 29 | 1,100 |
|  | 20 | 16 | 1,300 |
|  | 40 | 12 | 1,600 |
|  | 90 | 10 | 2,100 |
|  | 1200 | 7 | 11,600 |
| C6 |  0 | 0 | 0 |
| Drug 3B | 4 | 87 | 200 |
|  | 10 | 83 | 700 |
|  | 20 | 9 | 1,100 |
|  | 40 | 5 | 1,300 |
|  | 90 | 4 | 1,500 |
|  | 1200 | 4 | 5,900 |
| C7 | 0 | 0 | 0 |
| Drug 3B | 4 | 32 | 100 |
|  | 10 | 36 | 300 |
|  | 20 | 45 | 700 |
|  | 40 | 53 | 1,700 |
|  | 90 | 53 | 4,300 |
|  | 180 | 29 | 8,000 |
|  | 1200 | 24 | 47,000 |
| C8 | 0 | 0 | 0 |
| Crystalline Drug 3A | 4 | 1 | 0 |
|  | 10 | 1 | 0 |
|  | 20 | 1 | 0 |
|  | 40 | 2 | 0 |
|  | 90 | 1 | 100 |
|  | 1200 | 2 | 1,800 |

These data were used to determine the values of $C_{max90}$ and $AUC_{90}$. The results are shown in Table 9. As can be seen from the data, dispersions of drug in neutralized polymers provided greater concentration-enhancement than the dispersions using acidic polymers without neutralization, and greater concentration-enhancement that crystalline drug alone. The $AUC_{90}$ for the test compositions were 1.29-fold, 1.60-fold, and 1.33-fold that of each respective control using the same polymer without neutralization. The $C_{max90}$ for the dispersions of the invention ranged from 44- to 102-fold that of the crystalline control, and $AUC_{90}$ ranged from 24- to 57-fold that of the crystalline control.

TABLE 9

| Example | $C_{max90}$ (µg/mL) | AUC (min * µg/mL) |
|---|---|---|
| 12 | 203 | 2700 |
| C5 | 196 | 2100 |
| 13 | 88 | 2400 |
| C6 | 87 | 1500 |
| 14 | 115 | 5700 |
| C7 | 53 | 4300 |
| C8 Crystalline Drug 3A | 2 | 100 |

Example 16

This example discloses a dispersion of Drug 2 and a neutralized acidic polymer. First, an acidic polymer (HPMCP) was spray-dried with a basic salt (Ca(OH)$_2$), and the neutralized polymer was isolated in powdered form. A solution was prepared consisting of 0.649 wt % HPMCP, and 0.054 wt % Ca(OH)$_2$, 50.622 wt % methanol, 9.735 wt % acetone, and 38.94 wt % water. The solution was spray-dried by pumping the solution into a "mini" spray-dryer apparatus at 1.0 mL/min, with the nitrogen drying gas heated to 120° C. The resulting neutralized polymer (HPMCP-Ca) was collected on filter paper and dried under vacuum.

To form the dispersion of Example 16, a solution was made consisting of 0.23 wt % Drug 2, 0.69 wt % HPMCP-Ca (neutralized polymer), 36.94 wt % water, and 62.14 wt % methanol. The solution was spray-dried by pumping the solution into a "mini" spray-dryer apparatus at a rate of 0.8 mL/min. The nitrogen drying gas was heated to 100° C. The resulting solid amorphous dispersion was collected on filter paper, dried under vacuum, and stored in a dessicator. After drying, the dispersion of Example 16 contained 25 wt % Drug 2.

Example 17

The dispersion of Example 16 was tested to show that the neutralized dispersion provided concentration-enhancement of the drug in solution. For this test, 14.4 mg of the dispersion was added to a microcentrifuge tube for a total Drug 2 concentration of approximately 2000 µg/mL if all of the drug were to dissolve completely. The dissolution test was performed as described in Example 9. The results are shown in Table 10. Control C4 (consisting of 3.6 mg of crystalline Drug 2) is shown again for comparison.

TABLE 10

| Example | Time (min) | Drug 2 Concentration (µg/mL) | AUC (min * µg/mL) |
|---|---|---|---|
| 16 | 0 | 0 | 0 |
|  | 4 | 930 | 1,900 |
|  | 10 | 950 | 7,500 |
|  | 20 | 981 | 17,200 |
|  | 40 | 1014 | 37,100 |
|  | 90 | 978 | 86,900 |
|  | 1200 | 221 | 752,400 |
| C4 Crystalline Drug 2 | 0 | 0 | 0 |
|  | 4 | 131 | 300 |
|  | 10 | 114 | 1,000 |
|  | 20 | 124 | 2,200 |
|  | 40 | 107 | 4,500 |
|  | 90 | 126 | 10,300 |
|  | 1200 | 72 | 120,200 |

These data were used to determine the values of $C_{max90}$ and $AUC_{90}$. The results are shown in Table 11. The $C_{max90}$ for the test composition was 7.7-fold that of the crystalline control (C4), and the $AUC_{90}$ was 8.4-fold that of the control.

TABLE 11

| Example | $C_{max90}$ (µg/mL) | $AUC_{90}$ (min * µg/mL) |
|---|---|---|
| 16 | 1014 | 86,900 |
| C4 Crystalline Drug 2 | 131 | 10,300 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A process for forming a pharmaceutical composition, comprising
   (a) dissolving the following components in a common solvent to form a solution:

(1) a low-solubility acid-sensitive drug;
(2) an acidic polymer; and
(3) sufficient base to neutralize said acidic polymer to form a neutralized acidic polymer having a degree of neutralization of at least 0.9;

(b) atomizing said solution in the presence of a drying gas to form droplets ranging in size from 1 to 500 microns; and (c) removing said solvent so as to form solid particles of a solid amorphous dispersion comprising said drug and said neutralized acidic polymer.

2. The process of claim 1 wherein said base and said acidic polymer are dissolved in said solvent prior to said drug being dissolved in said solvent.

3. The process of claim 1 wherein said base is selected from the group consisting of sodium hydroxide, potassium hydroxide, calcium hydroxide, magnesium hydroxide, aluminum hydroxide, ammonia, ammonium hydroxide, ammonium acetate, sodium acetate, potassium acetate, calcium acetate, magnesium acetate, sodium citrate, trisodium phosphate, disodium phosphate, ethylene diamine, monoethanol amine, diethanol amine, triethanolamine, potassium citrate, sodium carbonate, sodium bicarbonate, sodium acetate, amine-functional polyacrylates, and sodium polyacrylic acid.

4. The process of claim 1 wherein said acidic polymer is enteric.

5. The process of claim 1 wherein said acidic polymer is selected from the group consisting of hydroxypropyl methyl cellulose acetate succinate, cellulose acetate phthalate, cellulose acetate trimellitate, hydroxypropyl methyl cellulose phthalate, and carboxymethyl ethyl cellulose.

6. The process of claim 1 wherein said low-solubility drug has a solubility in aqueous solution in the absence of said neutralized enteric acidic polymer of less than 1 mg/ml at any pH of from about 1 to about 8.

7. The process of claim 6 wherein said drug has an aqueous solubility of less than 0.1 mg/ml.

8. The process of claim 1 wherein said drug has a dose-to-aqueous-solubility ratio of at least 10 ml.

9. The process of claim 1 wherein said solvent is removed by spray-drying.

10. The process of claim 1 wherein said solid amorphous dispersion is substantially homogeneous.

11. The process of claim 1 wherein said solid amorphous dispersion has a single glass transition temperature.

12. The process of claim 1 wherein at least 90% of said drug is amorphous.

13. The process of claim 1 wherein said solvent comprises an organic compound selected from the group consisting of methanol, ethanol, n-propanol, iso-propanol, butanol, acetone, methyl ethyl ketone, methyl iso-butyl ketone, ethyl acetate, propylacetate, acetonitrile, methylene chloride, toluene, and 1,1,1-trichloroethane, and mixtures thereof.

14. The process of claim 13 wherein said solvent further comprises water.

15. The process of claim 1 wherein said solid particles are less than 100 microns in diameter.

\* \* \* \* \*